US007780961B2

(12) United States Patent
Steidler

(10) Patent No.: US 7,780,961 B2
(45) Date of Patent: Aug. 24, 2010

(54) **SELF-CONTAINING *LACTOCOCCUS* STRAIN**

(75) Inventor: Lothar Steidler, Bandon (IE)

(73) Assignee: Actogenix N.V., Zwijnaarde (BE)

( * ) Notice: Subject to any disclaimer, the term of this patent is extended or adjusted under 35 U.S.C. 154(b) by 451 days.

(21) Appl. No.: 10/687,996

(22) Filed: Oct. 17, 2003

(65) Prior Publication Data

US 2005/0101005 A1 May 12, 2005

Related U.S. Application Data

(63) Continuation of application No. PCT/EP02/04942, filed on May 3, 2002.

(30) Foreign Application Priority Data

May 3, 2001 (EP) ................................ 01201631
Dec. 7, 2001 (EP) ................................ 01204785

(51) Int. Cl.
*A61K 48/00* (2006.01)
*C12N 1/21* (2006.01)

(52) U.S. Cl. ................................ 424/93.2; 435/252.3

(58) Field of Classification Search ................ 435/193, 435/252.3, 320.1; 536/23.2
See application file for complete search history.

(56) References Cited

U.S. PATENT DOCUMENTS

| | | | |
|---|---|---|---|
| 4,100,495 A | 7/1978 | Luvison et al. | |
| 4,190,495 A | 2/1980 | Curtiss, III | |
| 4,888,170 A * | 12/1989 | Curtiss, III | 424/200.1 |
| 5,032,510 A | 7/1991 | Kovacevic et al. | |
| 5,149,532 A | 9/1992 | Brunell | |
| 5,240,705 A | 8/1993 | Jacobs | |
| 5,330,753 A | 7/1994 | Mekalanos et al. | |
| 5,364,774 A | 11/1994 | Muir et al. | |
| 5,401,642 A | 3/1995 | Fiers et al. | |
| 5,401,658 A | 3/1995 | Fiers et al. | |
| 5,417,986 A | 5/1995 | Reid et al. | |
| 5,455,034 A | 10/1995 | Nagaraja et al. | |
| 5,504,005 A | 4/1996 | Bloom et al. | |
| 5,547,664 A | 8/1996 | Charles et al. | |
| 5,559,007 A | 9/1996 | Suri et al. | |
| 5,591,632 A | 1/1997 | O'Donnell et al. | |
| 5,733,540 A | 3/1998 | Lee | |
| 5,824,538 A | 10/1998 | Branstrom et al. | |
| 5,837,409 A | 11/1998 | Bertrand et al. | |
| 6,100,388 A | 8/2000 | Casas et al. | |
| 6,130,082 A | 10/2000 | Majarian et al. | |
| 6,190,662 B1 | 2/2001 | Steidler et al. | |
| 6,190,669 B1 | 2/2001 | Noriega et al. | |
| 6,221,648 B1 | 4/2001 | Le Page et al. | |
| 6,261,561 B1 | 7/2001 | Stewart, Jr. et al. | |
| 6,262,119 B1 | 7/2001 | Ferrante et al. | |
| 6,605,286 B2 | 8/2003 | Steidler | |
| 6,610,300 B1 | 8/2003 | Segers et al. | |
| 6,685,943 B1 | 2/2004 | Hook et al. | |
| 6,746,671 B2 * | 6/2004 | Steidler et al. | 424/93.2 |
| 7,358,067 B2 | 4/2008 | Vrang et al. | |
| 2001/0006642 A1 | 7/2001 | Steidler et al. | |
| 2002/0019043 A1 | 2/2002 | Steidler et al. | |
| 2003/0202991 A1 | 10/2003 | Steidler et al. | |
| 2003/0203472 A1 | 10/2003 | Portnoy et al. | |
| 2004/0043003 A1 | 3/2004 | Chen et al. | |

FOREIGN PATENT DOCUMENTS

| | | |
|---|---|---|
| DE | 42 31 764 A1 | 3/1994 |
| EP | 0 176 320 | 4/1986 |
| EP | 0 406 003 A1 | 1/1991 |
| EP | 0 449 770 | 10/1991 |
| EP | 0 450 176 | 10/1991 |
| WO | WO 88/06626 | 9/1988 |
| WO | WO 91/06654 | 5/1991 |
| WO | WO 93/17117 | 9/1993 |
| WO | WO 95/03418 | 2/1995 |
| WO | WO 95/10614 | 4/1995 |
| WO | WO 95/10621 | 4/1995 |
| WO | WO 96/11277 | 4/1996 |
| WO | WO 96/32487 A1 | 10/1996 |
| WO | WO 96/40947 | 12/1996 |
| WO | WO 97/14806 | 4/1997 |
| WO | WO 98/31786 | 7/1998 |
| WO | WO 99/58652 | 11/1999 |
| WO | WO 00/01799 | 1/2000 |
| WO | WO 00/23471 | 4/2000 |
| WO | WO 02/090551 A2 | 11/2002 |
| WO | WO 03/096979 A | 11/2003 |
| WO | WO 2004/045392 A | 6/2004 |
| WO | WO 2004/046346 | 6/2004 |
| WO | WO 2007/063075 A | 6/2007 |
| WO | WO 2008/090223 A2 | 7/2008 |

OTHER PUBLICATIONS

Steidler et al (Jul. 2003) Nature Biotechnology, vol. 21, No. 7, pp. 785-789.*
Ross et al. (1990) App. Environ. Microbiology, vol. 56, pp. 2156-2163.*
ATCC Catalog Search performed online on Nov. 17, 2009 at www.atcc.org/ATCCAdvanceCatalogSearch/tabid/112/default.aspx.*
Ross, et al., Thymidylate Synthase Gene from *Lactococcus lactis* as a Genetic Marker: an Alternative to Antibiotic Resistance Genes, Applied and Environmental Microbiology, Jul. 1990, pp. 2164-2169, vol. 56, No. 7.
Schotte et al., Secretion of biologically active murine interleukin-10 by *Lactococcus lactis*, Enzyme and Microbial Technology, 2000, pp. 761-765, vol. 27.

(Continued)

*Primary Examiner*—Rebecca E. Prouty
(74) *Attorney, Agent, or Firm*—TraskBritt

(57) ABSTRACT

The invention relates to a recombinant *Lactococcus* strain, with environmentally limited growth and viability. More particularly, it relates to a recombinant *Lactococcus* that can only survive in a medium, where well-defined medium compounds are present. A preferred embodiment is a *Lactococcus* that may only survive in a host organism, where such medium compounds are present, but cannot survive outside the host organism in the absence of such medium compounds.

24 Claims, 9 Drawing Sheets

OTHER PUBLICATIONS

Steidler et al., Treatment of Murine Colitis by *Lactococcus lactis* Secreting Interleukin-10, Science, Aug. 25, 2000, pp. 135-155, vol. 289.
Taylor et al., Molecular Characterization of the Cell Cycle-regulated Thymidylate Synthase Gene of *Saccharomyces cerevisiae*, The Journal of Biological Chemistry, Apr. 15, 1987, pp. 5298-5307, vol. 262, No. 11.
PCT International Search Report, PCT/EP02/04942, dated Jan. 13, 2003, 2 pages.
PCT International Preliminary Examination Report, PCT/EP02/04942, dated Sep. 16, 2003, 5 pages.
Leong-Morgenthaler et al.. Lactose Metabolism in *Lactobacillus bulgaricus*: Analysis of the Primary Structure and Expression of the Genes Involved, Journal of Bacteriology. Mar. 1991, pp. 1951.57, vol. 173. No. 6.
Curtiss Tables III, IV and V, from U.S. Patent 4,888.170.
Cytokines Final Brochure for Cytokine Therapies, The Food and Drug Administration and the New York Academy of Sciences, held on Mar. 26-27, 2009.
Designing bacteria and white cells to deliver drugs to the gut, The Lancet, Sep. 20. 2003, www.thelancet.com, vol. 362, p. 964, J. Bradbury.
Eizaguirre et al., Abstract, Effect of Growth Hormone, Epidermal Growth Factor, and Insulin and Bacterial Translocation in Experimental Short Bowel Syndrome, Journal of Pediatric Surgery, 2000, pp. 692-695, vol. 35, No. 5.
Elliott et al., Bacterial colonization and healing of gastric ulcers: the effects of epidermal growth factor. Am. J. Physiol. Gastrointest. Liver Physiol., 2000, pp. G105-G112, vol. 278.
Farrell et al.. FEMS Microbiology Letters, 1995, 130:81-85.
U.S. Appl. No. 60/353,923, filed Jan. 31, 2002, Chen.
U.S. Appl. No. 60/353,964, filed Jan. 31, 2002, Chen.
U.S. Appl. No. 60/353,885, filed Jan. 31, 2002, Chen.
U.S. Appl. No. 60/401,465, filed Aug. 5, 2002, Chen.
Anderson, Human gene therapy, 1998, Nature, vol. 392.
Arslanoglu et al., 1998. Biotechnology Letters. pp. 917-921, vol. 20.
Bamba et al., Gastroentorol J., 1993, pp. 511-517, vol. 28, No. 4.
Barbara et al., interleukin 10 gene transfer prevents experimental colitis in rats, 2000, Gut, pp. 344-349, vol. 46.
Bellini et al., Production processes of recombinant IL-1beta from *Bacillus subtilis*: comparison between intracellular and exocellular expression. 1991, Journal of Biotechnology, pp. 177-192, vol. 18.
Bermudez-Humaran et al., J. Medical Microbiology, 2004. 53:427-433.
Bijlsma et al., TRENDS in Microbiology, 2003. 11/8:359-366.
Billman-Jacobe, Current Opinion in Biotechnology, 1996, 7:500-504.
Blast, Basic Local Alignment Search Tool, visited Jul. 7, 2009, <http://blast.ncbi.nlm.nih.gov/Blast.cgi. Alignment of unknown sequence to NCBI chromosome sequences.
Bojovic et al., Applied & Environ. Microbiol., 57/2:385-388 (1991).
Brett et al., Eur. J. Immunol., 23:1608-1614 (1993).
Chen et al., FEMS Microbiology Letters, 2003. 229:111-117.
Claverys et al., Gene, 1995, 164:123-128.
Curtiss Tables III, IV and V, from U.S. Patent 4,888,170, issued Dec. 19, 1989.
Cytokines Final Brochure for Cytokine Therapies, The Food and Drug Administration and The New York Academy of Sciences, held on Mar. 26-27, 2009.
Darji et al., J. Biotechnology, 1995, 43:205-212.
Designing bacteria and white cells to deliver drugs to the gut, The Lancet, Sep. 20, 2003, www.thelancet.com, vol. 362, p. 964, J. Bradbury.
Edwards et al., Infection & Immunity, 60/6:2514-2521 (1992).
Eizaguirre et al., Abstract, Effect of Growth Hormone, Epidermal Growth Factor, and Insulin and Bacterial Translocation in Experimental Short Bowel Syndrome, Journal of Pediatric Surgery, 2000, pp. 692-695, vol. 35, No. 5.
Elliott et al.. Bacterial colonization and healing of gastric ulcers: the effects of epidermal growth factor. Am. J. Physiol. Gastrointest. Liver Physiol., 2000, pp. G105-G112, vol. 278.
English translation of the Japanese Office Action dated Apr. 7, 2009.
Figler et al., Archives Biochemistry and Biophysics, 2000, 376/1:34-46.
Fischetti et al., Current Opinion in Biotechnology, Oct. 1993, 4/5:603-610.
Fu et al., "Development of a chromosome-plasmid balanced lethal system for *Lactobacillus acidophilus* with thyA gene as selective marker," Microbiol. Immunol., 2000, pp. 551-556, vol. 44, No. 7, Abst. only.
Gasson, Abstract, "In vivo genetic systems in lactic acid bacteria," FEMS Microbiol., 1990, Rev. 87:43-60.
Gotz, J. Applied Bacteriology Symposium Supplement, 1990, 49S-53S.
Gutierrez et al., Appl. Microbial. Biotechnol., 2006, 72/1:41-51.
Hansson et al., J. Bacteriology, Jul. 1992, 174/13:4239-4245.
Hardin et al., Gut, 1999, pp. 26-32, vol. 44.
Hazebrouck et al., Applied and Environmental Microbiology, Dec. 2006, 72/12:7460-7467.
Heath et al., Abstract, Cytokines as immunological adjuvants. Vaccine, 1992, pp. 427-434, vol. 10, No. 7.
Hegedus et al., Gene, 1998, 207:241-249.
Herfarth et al., Interleukin 10 suppresses experimental chronic, granulomatous inflammation induced by bacterial cell wall polymers, 1996, GUT, pp. 836-845, vol. 39, Abstr. only.
Holmes et al., Infection & Immunity, 66/10:4633-4639 (1998).
Huibregtse et al., Abstract, Induction of Antigen-specific Oral Tolerance by Genetically Modified *Lactococcus lactis* Delivering DQ8-specific Immunodominant Gliadin Epitopes to Gluten-sensitized Class II Transgenic Mice, Clinical Immunology, Jan. 1, 2007, pp. S53-S54, vol. 123.
Iwaki et al., Infection Immunity, 58/9:2929-2934 (1990).
Janssen et al., Microbial Pathogenesis, 1995, 19:193-201.
Jeong et al., Food Microbiology, 2006, 23:82-89.
Kingman, Trial Tests If Modified Bacteria Can Deliver to Gut Mucosa, Jun. 15, 2003, online, BioWorld Online.
Kitchener, Prisons without bars, Nature Reviews, Genetics. Aug. 2003, p. 577, vol. 4.
Koivula et al., Isolation and Characterization of *Lactococcus lactis* subsp. lactis Promoters, Applied and Environmental Microbiology, Feb. 1991, pp. 333-340. vol. 57, No. 2.
Kong et al., Secretion of Human Interleukin 2 by Recombinant *Mycobacterium bovis* BCG, Infection and Immunity, Mar. 1995, pp. 799-803, vol. 63. No. 3.
Korelitz et al., Immunosuppressive therapy of inflammatory bowel disease: A historical perspective, The Gastroenterologist 5 (2) : 141-152. (1995).
Kruisselbrink et al., Recombinant *Lactobacillus* Plantarum Inhibits Ouse Dust Mite-Specific T-Cell Responses, Clinical and Experimental Immunology, Oct. 1, 2001, pp. 2-08, vol. 126, No. 1.
Kuby, Cytokine receptors, 1994, Immunology. pp. 304-306, W.H. Freeman & Comp. (eds).
Kurahayashi et al., Effects of EGF administration in the intestinal adaptation in the rat after massive intestinal resection, Diagnostics and New Medicaments, 1991, pp. 1691-1701, vol. 28, No. 9.
Leach et al., the role of IL-10 in inflammatory bowel disease: "Of mice and men," 1999, Toxicologic Pathology, pp. 123-133.
Leenhouts et al., Applied and Environmental Microbiology, Dec. 1998, 64/12:4736-4742.
Leenhouts et al., Applied and Environmental Microbiology. Sep. 1991, 57/9:2568-2575.
Leenhouts et al., J. Bacteriology. Aug. 1991, 173-15:4794-4798.
Leong et al.. Selective Induction of Immune Responses by Cytokines Coexpressed in Recombinant Fowlpox Virus, Journal of Virology, Dec. 1994. pp. 8125-8130, vol. 68, No. 12.
Liu et al., J. Applied Microbiology, 2005, 98:127-135.
Maassen et al., Abstract, Reduced experimental autoimmune *Encephalomyelitis* after intranasal and oral administration of recombinant *Lactobacilli* expressing myelin antigens, Vaccine, Dec. 1, 2003, pp. 4685-4693, vol. 21, No. 32.
Mayer et al.. Abstract, Therapeutic potential of oral tolerance, Nature Reviews Immunology, Jun. 2004. pp. 407-419, vol. 4, No. 6.

McCluskie et al., Route and method of delivery of DNA vaccine influence immune responses in mice and non-human primates, 1999, Molecular Medicine, pp. 287-300, vol. 5.
Merriam-Webster's Collegiate Dictionary, Tenth Edition, Springfield, Massachusetts, USA, 2001, p. 922.
Motamedi et al., Gene, 1995, 160:25-31.
Norton et al., FEMS Immunology and Medical Microbiology, 1996, 14:167-177.
Norton et al., FEMS Microbiology Letters, 1994, 120/3:249-256.
Norton et al., Progress in the Development of *Lactococcus lactis* as a Recombinant Mucosal Vaccine Delivery System, Folia Microbiologica, Jan. 1, 1995, pp. 225-230, vol. 40, No. 3.
Norton et al., Vaccine, 1997, 15(6/7):616-619.
Nottebrock et al., Thymidine Concentrations in Serum and Urine of Different Animal Species and Man, Biochemical Pharmacology, 1977, pp. 2175-2179, vol. 26, Pergamon Press. Great Britain.
Oggioni et al., Gene, 1996, 169:85-90.
Oggioni et al., Vaccine, 1995, 13/8:775-779.
Paccez et al., Vaccine, 2007, 24:4671-4680.
Page et al., Innovations in oral gene delivery: challenges and potentials, 2001, DDT, pp. 92-101, vol. 6.
Papadakis et al., Role of cytokine in the pathogenesis of inflammatory bowel disease, 2000, Annu. Rev. Med., vol. 51, pp. 289-298.
Platteeuw et al., Applied and Environmental Microbiology, 1996, 62/3:1008-1013.
Pouwels et al., International J. Food Microbiology, 1998, 41:155-167.
Pouwels et al., J. Biotechnology, 1996, 44:183-192.
Pozzi et al., Abstract, Research in Microbiology, 1990, 141/6:659-670.
Pozzi et al., Abstract, Research in Microbiology, 1992, 143/5:449-457.
Pozzi et al., Infection and Immunity, May 1992, 60/5:1902-1907.
Ramasany et al., Vaccine, 2006, 24:3900-08.
Rao et al., Eur. J. Phannacol., 1996, pp. 209-212, vol. 303, No. 3.
Rapoport, Current Opinion in Biotechnology, 1:21-27 (1990).
Reviriego et al., International Dairy Journal, 2007, 17-574-577.
Robinson et al., Nature Biotechnology. 1997, 15:653-57.
Rodriguez et al., International J. Food Microbiology, 2003, 80:101-116.
Salzet, Michel, "Leech Thrombin Inhibitors," Current Pharmaceutical Design, 2002, pp. 493-503, vol. 8.
Samuelson et al., J. Bacteriology, Mar. 1995, 177/6:1470-1476.
Sasaki et al., "thyA as a Selection Marker in Construction of Food-Grade Host-Vector and Integration Systems for *Streptococcus Thermophilus*," Applied and Environmental Microbiology, Mar. 2004, pp. 1858-1864, vol. 70, No. 3..
Scott et al., Abstract, FEMS Microbiology Ecology, Aug. 1998, 26/3:219-230.
Sham et al., Abstract, Epidermal Growth Factor Improves Nutritional Outcome in a Rat Model of Short Bowel Syndrome, Journal of Pediatric Surgery, 2002, pp. 765-769, vol. 37, No. 5.
Sibakov et al., Applied & Environ. Microbiol., 57/2:341-348 (1991).
Slos et al., FEMS Microbiology Letters, 1998, 169:29-36.
Steidler et al., Secretion of Biologically Active Murine Interleukin-2by *Lactococcus lactis* subsp. lactis, Appl. Environ, Microbiol., 1995, 61:1627-1629.
Steidler et al., J. Bacteriol. 175/23:7639-7643 (1993).
Steidler et al., Mucosal Delivery of Murine Interleukin-2 (IL-2) and IL-6 by recombinant Strains of *Lactococcus lactis* Coexpressing Antigen and Cytokine, Infection and Immunity, 1998, pp. 3183-3189 vol. 66, No. 7:.
Steidler et al., NATO ASI Series vol. H98, pp. 63-79 (1996).
Steidler et al., Therapeutic drug delivery by genetically modified *Lactococcus lactis*, Annals of the New York Academy of Sciences, 2006, pp. 176-186, Abstr. only.
Stern, et al., Abstract, Microscopy Research and Technique, 2000, pp. 138-148, vol. 51.
Targan et al., Clarifying the causes of Croh's, 1995, Nature Medicine, pp. 1241-1243, vol. 1.
Thompson et al., Plasmid, 2001, 46:188-201.
Van De Guchte et al., Applied and Environmental Microbiology, Jan. 1989, 55/1:224-228.
Van De Guchte et al., Heterologous Gene Expression in *Lactococcus lactis* subsp. lactis: Synthesis, Secretion, and Processing of the *Bacillus subtilis* Neutral Protease, Applied and Environmental Microbiology, Sep. 1990, p. 2606-2611, vol. 56, No. 9.
Van Mallaert et al., Med. Fac. Landbouww, Rijksuniv. Gent., 1989, 54(4b):1477-1485.
Verma et al., Gene therapy—promises: problems and prospects, 1997, Nature, pp. 239-242, vol. 389.
Waterfield et al., Gene. 1995, 165:9-15.
Wells et al., Applied & Environ. Microbiol., 59/11:3954-3959 (1993).
Wells et al., International Dairy Journal, 1995, 5:1071-1079.
Wells et al., Lactic acid bacteria as vaccine delivery vehicles, Antonie van Leeuwenhoek 70:317-330 (1996).
Wells et al., Molecular Microbiol. 8/6:1155-1162 (1993).
Wiedermann, Abstract, Prophylaxis and therapy of allergy by mucosal tolerance induction with recombinant allergens or allergen constructs, Current Drug Targets, Inflammation and Allergy, Oct. 1, 2005, pp. 577-83, vol. 4. No. 5, Bentham Science Publishers.
Williams et al., Plasmid, 2002, 47:241-245.
Willis, Bacterial drug delivery, Newsinbrief, online (after Jun. 15, 2003).
Notice of Allowance for U.S. Appl. No. 11/018,188 dated Apr. 8, 2009.
Office Action for U.S. Appl. No. 11/127,921 dated Mar. 10, 2009.

* cited by examiner

Figure 7A:
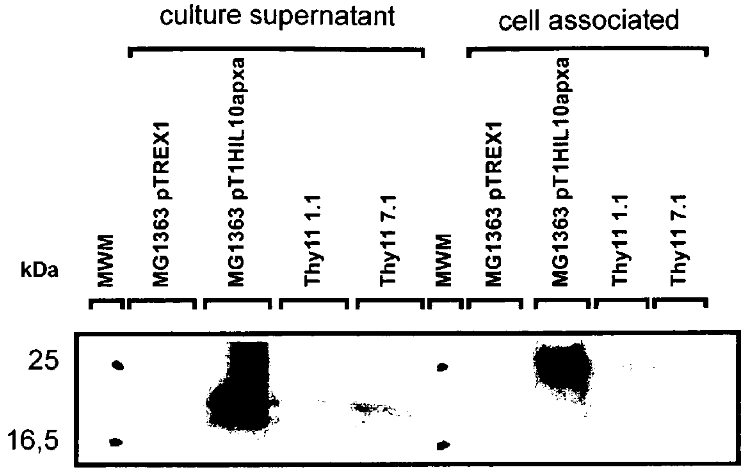
Figure 7B:
| | hIL10PxA | | pTREX1 | | Thy11 1.1 | | Thy11 7.1 | |
|---|---|---|---|---|---|---|---|---|
| | sample 1 | sample 2 | sample 3 | sample 4 | sample 5 | sample 6 | sample 7 | sample 8 |
| concentration (ng/ml) | 131,34 | 123,01 | 0 | 0 | 2,55 | 1,8 | 2,8 | 2,72 |
| std (ng/ml) | 0 | 15,27 | 0 | 0 | 1,05 | 0 | 0,95 | 0,53 |
| **average (ng/ml)** | | 127,18 | | 0,00 | | 2,18 | | 2,76 |
| std (ng/ml) | | 5,89 | | | | 0,53 | | 0,06 |
Figure 8A:
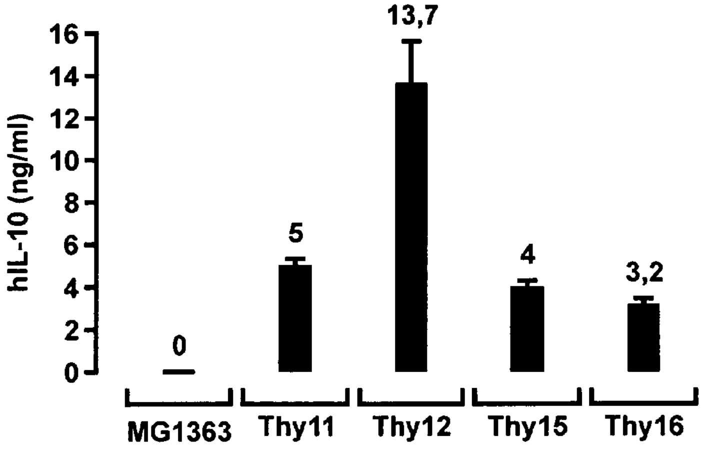
Figure 8B:
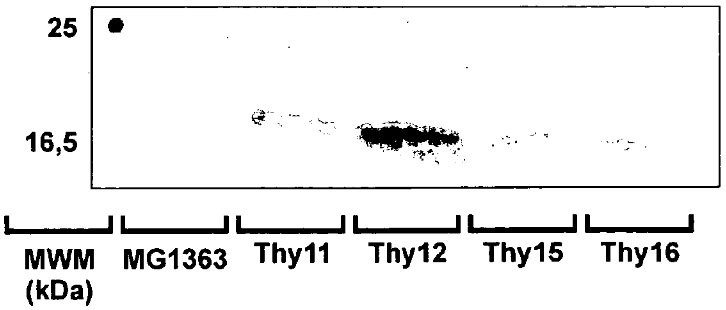

SELF-CONTAINING *LACTOCOCCUS* STRAIN

CROSS-REFERENCE TO RELATED APPLICATION

This application is a continuation of PCT International Patent Application No. PCT/EP02/04942, filed on May 3, 2002, designating the United States of America, and published, in English, as PCT International Publication No. WO 02/090551 A2 on Nov. 14, 2002, the contents of the entirety of which are incorporated herein by this reference.

TECHNICAL FIELD

The invention relates to a recombinant *Lactococcus* strain, with environmentally limited growth and viability. More particularly, it relates to a recombinant *Lactococcus* that can only survive in a medium, where well-defined medium compounds are present. A preferred embodiment is a *Lactococcus* that may only survive in a host organism, where the medium compounds are present, but cannot survive outside the host organism in an absence of the medium compounds. Moreover, the *Lactococcus* can be transformed with prophylactic and/or therapeutic molecules and can, as such, be used to treat diseases such as inflammatory bowel diseases.

BACKGROUND

Lactic acid bacteria have long been used in a wide variety of industrial fermentation processes. They have generally-regarded-as-safe ("GRAS") status, making them potentially useful organisms for the production of commercially important proteins. Indeed, several heterologous proteins, such as Interleukin-2, have been successfully produced in *Lactococcus* spp (Steidler et al., 1995). It is, however, undesirable that such genetically modified microorganisms survive and spread into the environment.

To avoid unintentional release of genetically modified microorganisms, special guidelines for safe handling and technical requirements for physical containment are used. Although this may be useful in industrial fermentations, the physical containment is generally considered as insufficient, and additional biological containment measures are taken to reduce the possibility of survival of the genetically modified microorganism in the environment.

Biological containment is extremely important in cases where physical containment is difficult or even inapplicable. This is, amongst others, the case in applications where genetically modified microorganisms are used as live vaccines or as a vehicle for delivery of therapeutic compounds. Such applications have been described, for example, in PCT. International Publication Number WO 97/14806, which discloses the delivery of biologically active peptides, such as cytokines, to a subject by recombinant noninvasive or nonpathogenic bacteria. Further, PCT International Publication Number WO 96/11277 describes the delivery of therapeutic compounds to an animal or human by administering a recombinant bacterium encoding a therapeutic protein. Steidler et al. (2000) describe the treatment of colitis by administration of a recombinant *Lactococcus lactis* secreting Interleukin-10. Such a delivery may indeed be extremely useful to treat a disease in an affected human or animal, but the recombinant bacterium may act as a harmful and pathogenic microorganism when it enters a nonaffected subject, and an efficient biological containment that avoids such unintentional spreading of the microorganism is needed.

Biological containment systems for host organisms may be passive and based on a strict requirement of the host for a specific growth factor or a nutrient that is not present or is present in low concentrations in the outside environment.

Alternatively, it may be active and, based on so-called suicidal genetic elements in the host, wherein the host is killed in the outside environment by a cell-killing function, encoded by a gene that is under the control of a promoter only being expressed under specific environmental conditions.

Passive biological containment systems are well known in microorganisms such as *Escherichia coli* or *Saccharomyces cerevisiae*. Such *E. coli* strains are disclosed, for example, in U.S. Pat. No. 4,190,495. Also, PCT International Publication Number WO 95/10621 discloses lactic acid bacterial suppressor mutants and their use as means of containment in lactic acid bacteria, but in that case, the containment is on the plasmid level, rather than on the level of the host strain and it stabilizes the plasmid in the host strain, but does not provide containment for the genetically modified host strain itself.

Active suicidal systems have been described by several authors. Such systems consist of two elements: a lethal gene and a control sequence that switches on the expression of the lethal gene under nonpermissive conditions. For example, PCT International Publication Number WO 95/10614 discloses the use of a cytoplasmatically active truncated and/or mutated *Staphylococcus aureus* nuclease as a lethal gene. PCT International Publication Number WO 96/40947 discloses a recombinant bacterial system with environmentally limited viability, based on the expression of either an essential gene, expressed when the cell is in the permissive environment and not expressed or temporarily expressed when the cell is in the nonpermissive environment, and/or a lethal gene, wherein expression of the gene is lethal to the cell and the lethal gene is expressed when the cell is in the nonpermissive environment but not when the cell is in the permissive environment. PCT International Publication Number WO 99/58652 describes a biological containment system based on the relE cytotoxin. However, most systems have been elaborated for *Escherichia coli* (Tedkin et al., 1995; Knudsen et al., 1995; Schweder et al., 1995) or for *Pseudomonas* (Kaplan et al., 1999; Molino et al., 1998). Although several of the containment systems theoretically can by applied to lactic acid bacteria, no specific biological containment system for *Lactococcus* has been described that allows the usage of a self-containing and transformed *Lactococcus* to deliver prophylactic and/or therapeutic molecules in order to prevent and/or treat diseases.

DISCLOSURE OF THE INVENTION

The invention includes a suitable biological containment system for *Lactococcus*. A first aspect of the invention is an isolated strain of *Lactococcus* sp. comprising a defective thymidylate synthase gene.

Another aspect of the invention is the use of a strain according to the invention as a host strain for transformation, wherein the transforming plasmid does not comprise an intact thymidylate synthase gene.

Still another aspect of the invention is a transformed strain of *Lactococcus* sp. according to the invention, comprising a plasmid that does not comprise an intact thymidylate synthase gene. Another aspect of the invention relates to a transformed strain of *Lactococcus* sp. comprising a gene or expression unit encoding a prophylactic and/or therapeutic molecule such as Interleukin-10. Consequently, the present invention also relates to the usage of a transformed strain of *Lactococcus* sp. to deliver prophylactic and/or therapeutic molecules and, as such, to treat diseases. Methods to deliver the molecules and methods to treat diseases such as inflammatory bowel diseases are explained in detail in PCT International Publication Numbers WO 97/14806 and WO 00/23471 to Steidler et al. and in Steidler et al. (Science 2000, 289:1352), the contents of all of which are incorporated herein by this reference.

Another aspect of the invention is a medical preparation comprising a transformed strain of *Lactococcus* sp., according to the invention.

The invention further demonstrates that the transformed strains surprisingly pass the gut at the same speed as the control strains, showing that their loss of viability indeed is not different from that of the control strains. However, once the strain is secreted in the environment, for example, in the feces, it is not able to survive any longer.

The transforming plasmid can be any plasmid, as long as it does not complement the thyA mutation. It may be a self-replicating plasmid that preferably carries one or more genes of interest and one or more resistance markers, or it may be an integrative plasmid. In the latter case, the integrative plasmid itself may be used to create the mutation by causing integration at the thyA site, whereby the thyA gene is inactivated.

BRIEF DESCRIPTION OF THE FIGURES

FIG. 3A shows an agarose gel of the products of the indicated PCR reactions. FIG. 3B shows the positions at which primers attach in the thyA (1), upstream (2) or downstream (3) PCR's. Oligonucleotide primers used:

(1): ATgACTTACgCAgATCAAgTTTTT (SEQ ID NO:8 of the accompanying SEQUENCE LISTING, which is incorporated herein by this reference and TTAAATTgCTAAATCAAATTTCAATTg. (SEQ ID NO:9)

(2): TCTgATTgAgTACCTTgACC (SEQ ID NO:10) and gCAATCATAATTggTTTTATTg (SEQ ID NO:11)

(3): CTTACATgACTATgAAAATCCg (SEQ ID NO:12) and cTTTTTTATTATTAgggAAAgCA (SEQ ID NO:13).

Figure 4A:
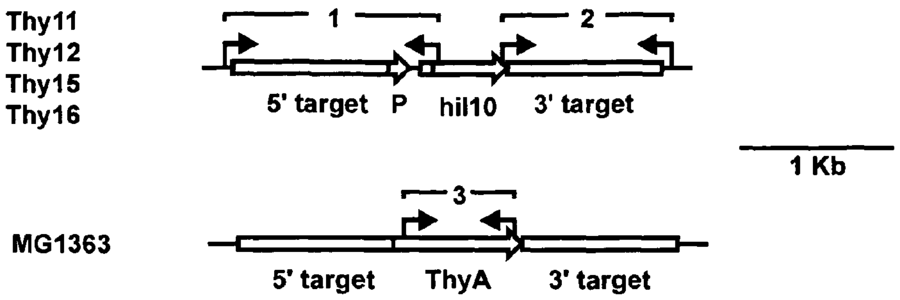
Figure 4B:
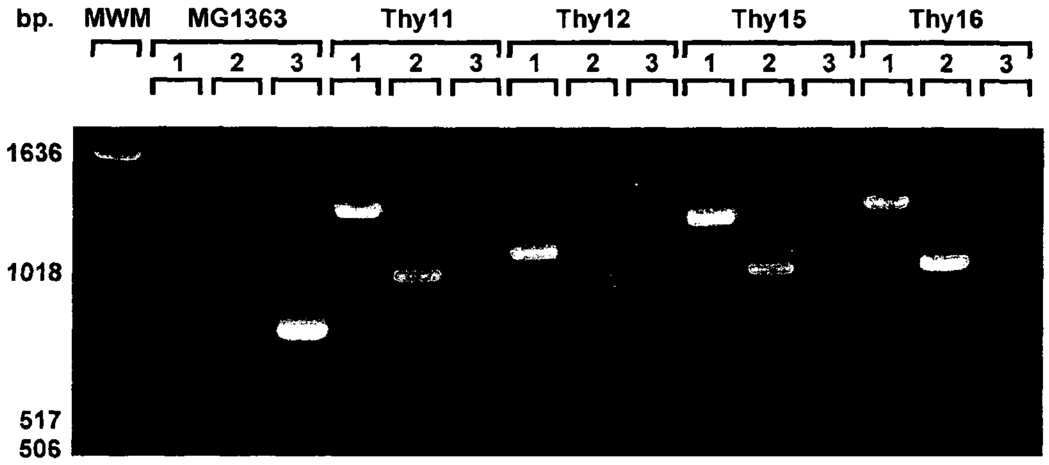

FIGS. 4A and 4B: PCR identification of Thy11, Thy12, Thy15 and Thy16. Standard PCR reactions were performed by using three-day old colonies of the indicated strains as a source of DNA template. FIG. 4A shows the positions at which primers attach in the upstream (1), downstream (2) or thyA (3), PCRs. Oligonucleotide primers used:

```
(1): ATgACTTACgCAgATCAAgTTTTT     (SEQ ID NO: 8)
and

     TTAAATTgCTAAATCAAATTTCAATTg (SEQ ID NO: 9)

(2): TCTgATTgAgTACCTTgACC        (SEQ ID NO: 10)
and

     gCAATCATAATTggTTTTATTg      (SEQ ID NO: 11)

(3): CTTACATgACTATgAAAATCCg      (SEQ ID NO: 12)
and

     cTTTTTTATTATTAgggAAAgCA.    (SEQ ID NO: 13)
```

FIG. 4B shows an agarose gel of the products of the indicated PCR reactions.

Figure 5A:
Figure 5B:
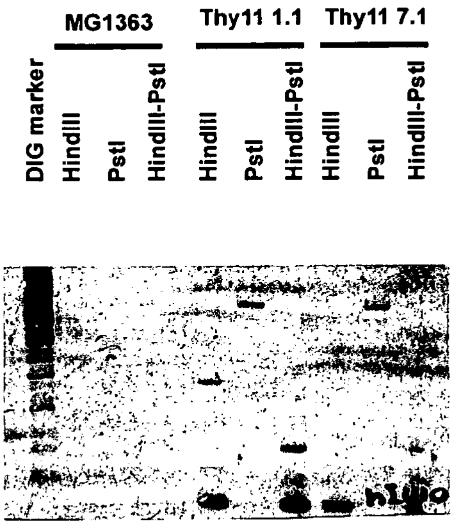

FIGS. 5A and 5B: Southern blot analysis of the indicated strains. Chromosomal DNA was extracted and digested with the indicated restriction enzymes. Following agarose gel electrophoresis, the DNA was transferred to a membrane and the chromosome structure around the thyA locus was revealed by use of DIG-labeled thyA or hIL-10 DNA fragments (FIG. 5A). FIG. 5B shows a schematic overview of the predicted structure of the thyA locus in both MG1363 and Thy11.

Figure 6A:
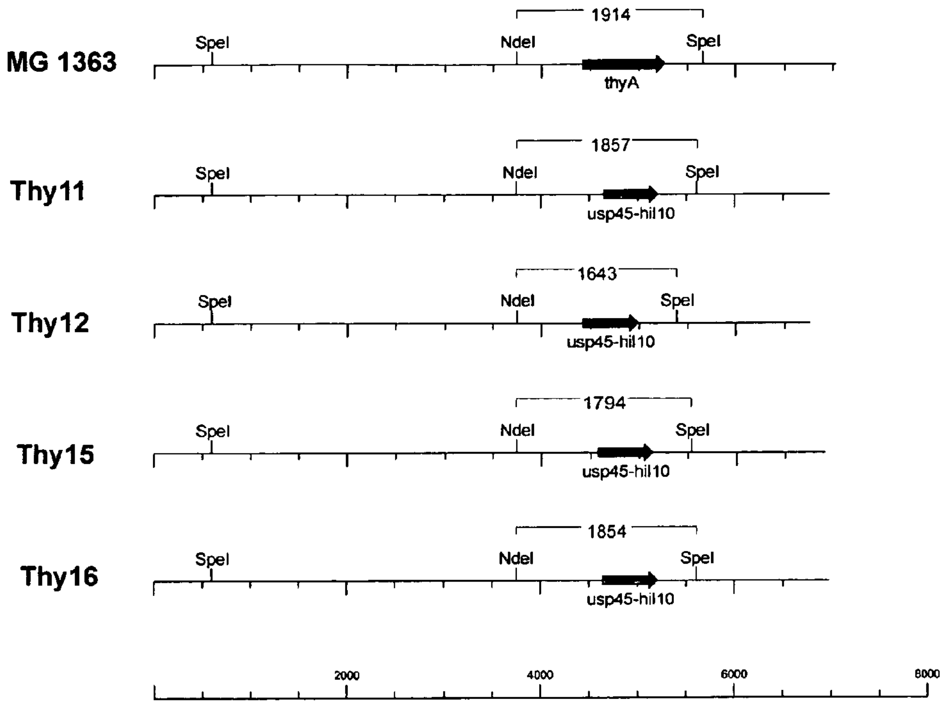
Figure 6B:
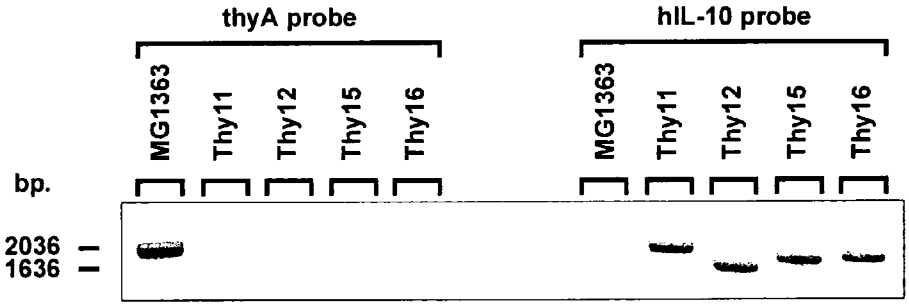

FIG. 6A shows a schematic overview of part of the predicted structure of the *L. lactis* chromosome at the thyA locus in MG1363, Thy11, Thy12, Thy15 and Thy16. Numbers indicate base pairs. FIG. 6B illustrates a Southern blot analysis of the indicated strains. Chromosomal DNA was extracted and digested with NdeI and SpeI restriction enzymes. Following agarose gel electrophoresis, the DNA was transferred to a membrane and the chromosome structure around the thyA locus was revealed by use of DIG-labeled thyA or hIL-10 DNA fragments.

FIGS. 7A and 7B: Production of hIL-10. FIG. 7A shows a western blot revealed with anti-hIL-10 antiserum of culture supernatant and cell-associated proteins of the indicated strains. FIG. 7B shows quantification (by ELISA) of hIL-10 present in the culture supernatant.

FIGS. 8A and 8B: Production of hIL-10. FIG. 8A shows quantification (by ELISA) of hIL-10 present in the culture supernatant of the indicated strains. FIG. 8B shows a western blot revealed with anti-hIL-10 antiserum of culture supernatant proteins of the indicated strains.

Figure 9:
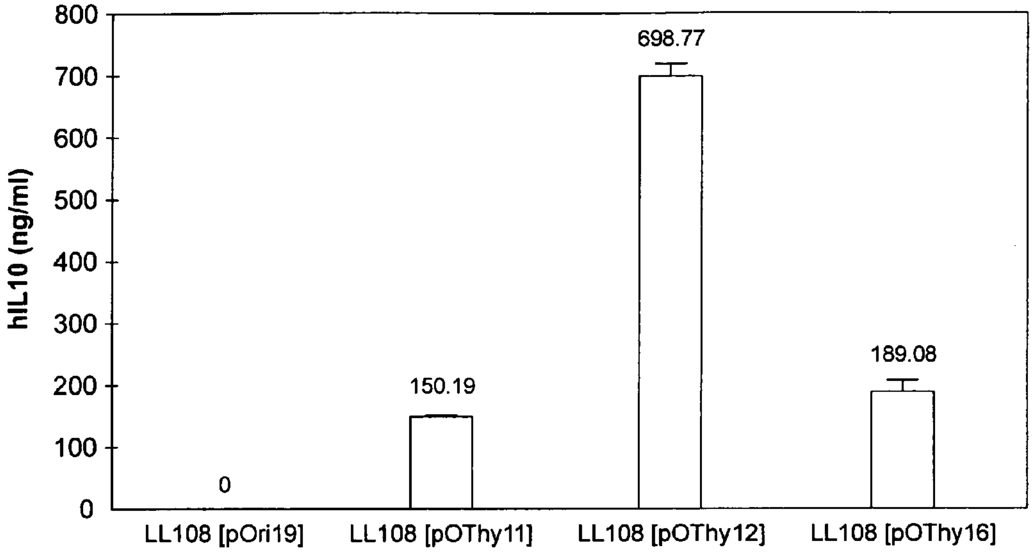

FIG. 9: Production of hIL-10 by the *L. lactis* strains LL108 carrying pOThy11, pOThy12, or pOThy16. Quantification (by ELISA) of hIL-10 present in the culture supernatant of the indicated strains is shown. The N-terminal protein sequence of the recombinant hIL-10 was determined by Edman degradation and was shown to be identical to the structure as predicted for the mature, recombinant hIL-10. The protein showed full biological activity.

Figure 10A:
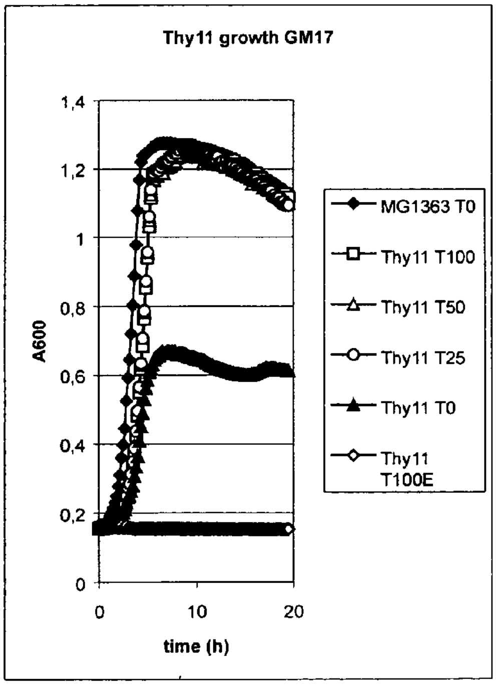
Figure 10B:
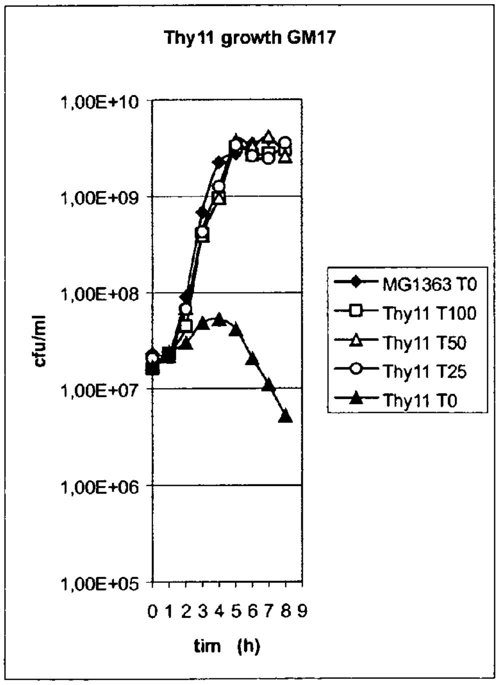

FIGS. 10A and 10B: Growth rate of the indicated strains in GM17 containing 100 μg/ml (T100), 50 μg/ml (T50), 25 μg/ml (T25), or no (T0) extra thymidine and possibly supplemented with 5 μg/ml of erythromycin (E). Saturated overnight cultures (prepared in T50) were diluted 1:100 in the indicated culture media. FIG. 10A shows the kinetics of absorbance accumulation. FIG. 10B shows the kinetics of the number of colony-forming units (cfu) per ml of culture.

Figure 11:
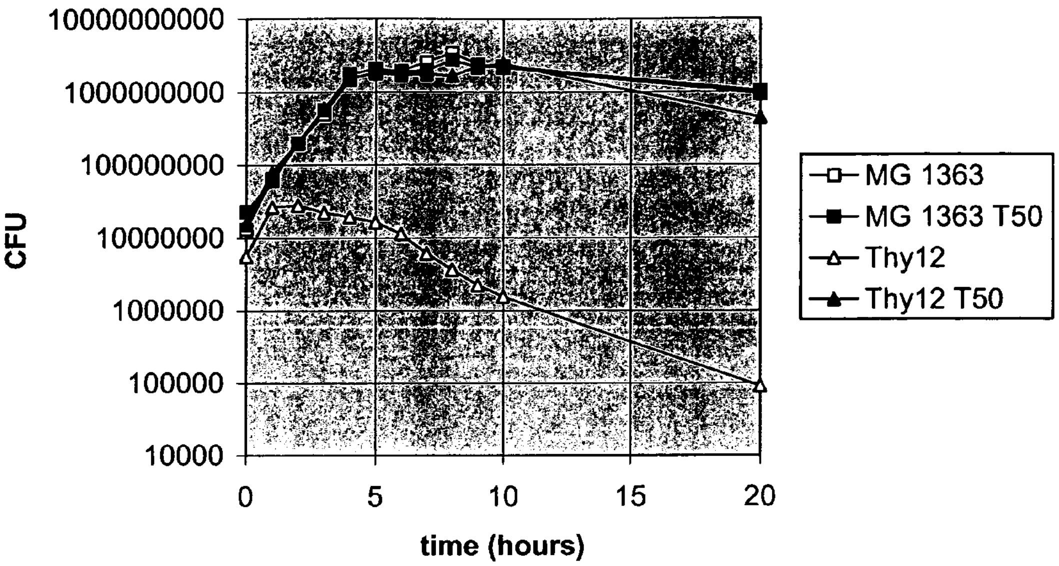

FIG. 11: Growth rate of MG1363 and Thy12 in thymidine-free medium (TFM). TFM was prepared by growing *L. lactis* Thy12 bacteria in GM17, removing the bacteria by subsequent centrifugation and filtration on a 0.22 μm pore size filter, adjusting the pH to 7.0 and autoclaving. MG1363 and Thy12 bacteria were collected from an overnight culture in GM17 or GM17+50 μg/ml of thymidine, respectively, and washed in M9 buffer (6 g/l $Na_2HPO_4$, 3 g/l $KH_2PO_4$, 1 g/l $NH_4Cl$, 0.5 g/l NaCl in water). The suspensions of both were either diluted in TFM or TFM supplemented with 50 μg/ml of thymidine (T50). CFU counts were determined at different time points: t=0, 1, 2, 3, 4, 5, 6, 7, 8, 9, 10 and 20 hours. This shows that Thy12 viability is severely impaired in the absence of thymidine.

Figure 12:
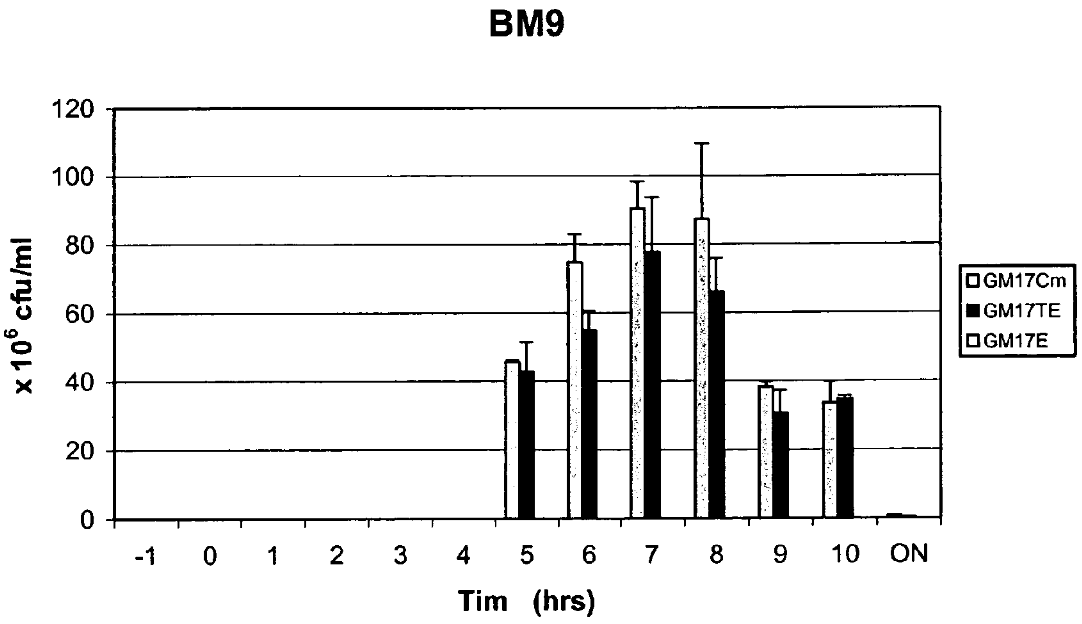

FIG. 12: Intestinal passage and viability: *L. lactis* MG1363 was transformed with the plasmid pLET2N, which carries a chloramphenicol (Cm) resistance marker. *L. lactis* Thy12 was transformed with the plasmid pT1NX, which carries an erythromycin (Em) resistance marker. Of both strains, $10^9$ bacteria were resuspended in BM9 (6 g/l $Na_2HPO_4$, 3 g/l $KH_2PO_4$, 1 g/l $NH_4Cl$, 0.5 g/l NaCl in 25 mM $NaHCO_3$+25 mM $Na_2CO_3$), mixed and inoculated in three mice at t=0 h. Feces were collected at the time intervals −1 to 0, 0 to 1, 1 to 2, 2 to 3, 3 to 4, 4 to 5, 5 to 6, 6 to 7, 7 to 8, 8 to 9, 9 to 10 and 10 to overnight. All samples were resuspended in isotonic buffer and appropriate dilutions were plated on GM 17 (M17 medium, Difco, St. Louis, Mo., supplemented with 0.5% glucose) plates containing either Cm, Em or Em+50 μg/ml thymidine. Colony-forming units for the different plates are represented in the graph.

DETAILED DESCRIPTION OF THE INVENTION

As previously identified, the invention includes a suitable biological containment system for *Lactococcus*. In one aspect, the invention is an isolated strain of *Lactococcus* sp. comprising a defective thymidylate synthase gene. Preferably, the defective thymidylate synthase gene is inactivated by gene disruption. Even more preferably, the *Lactococcus* sp. is *Lactococcus lactis*. A special embodiment is a *Lactococcus* sp. strain, preferably *Lactococcus lactis*, more preferably a *Lactococcus lactis* MG1363 derivative, wherein the thymidylate synthase gene has been disrupted and replaced by an Interleukin-10 expression unit. The Interleukin-10 expression unit is preferably, but not limited to, a human Interleukin-10 expression unit or gene encoding for human Interleukin-10.

The *Lactococcus lactis* subsp. *lactis* thymidylate synthase gene (thyA) has been cloned by Ross et al. (1990a). Its sequence is comprised in SEQ ID NO:3 and SEQ ID NO:5. European Patent Application Publication Number 0406003 discloses a vector devoid of antibiotic resistance and bearing a thymidylate synthase gene as a selection marker; the same vector has been described by Ross et al. (1990b). However, this vector could not be used in a *Lactococcus lactis* strain due to the lack of a suitable thyA mutant that has never been described. The present invention discloses how to construct such a mutant by gene disruption using homologous recombination in *Lactococcus*. In a preferred embodiment, the thyA gene is disrupted by a functional human Interleukin-10 expression cassette. However, it is clear that any construct can be used for gene disruption, as long as it results in an inactivation of the thyA gene or in an inactive thymidylate synthase. As a nonlimiting example, the homologous recombination may result in a deletion of the gene, in one or more amino acid substitutions that lead to an inactive form of the thymidylate synthase, or in a frame shift mutation resulting in a truncated form of the protein.

Such a *Lactococcus* sp. thyA mutant is very useful as a host strain for transformation in situations where more severe containment than purely physical containment is needed. Indeed, thyA mutants cannot survive in an environment without or with only a limited concentration of thymidine and/or thymine. When such a strain is transformed with a plasmid that does not comprise an intact thyA gene and cannot complement the mutation, the transformed strain will become suicidal in a thymidine/thymine-poor environment. Such a strain can be used in a fermentor as an additional protection for the physical containment. Moreover, the present invention discloses that such a strain is especially useful in cases where the strain is used as a delivery vehicle in an animal body. Indeed, when such a transformed strain is given, for example, orally to an animal—including humans—it survives in the gut, provided that a sufficiently high concentration of thymidine/thymine is present, and produces homologous and/or heterologous proteins, such as human Interleukin-10, that may be beneficial for the animal.

The invention further demonstrates that the transformed strains surprisingly pass the gut at the same speed as the control strains, showing that their loss of viability indeed is not different from that of the control strains. However, once the strain is secreted in the environment, for example, in the feces, it is not able to survive any longer.

The transforming plasmid can be any plasmid, as long as it does not complement the thyA mutation. It may be a self-replicating plasmid that preferably carries one or more genes of interest and one or more resistance markers, or it may be an integrative plasmid. In the latter case, the integrative plasmid itself may be used to create the mutation by causing integration at the thyA site, whereby the thyA gene is inactivated. Preferably, the active thyA gene is replaced by double homologous recombination by a cassette comprising the gene or genes of interest, flanked by targeting sequences that target the insertion to the thyA target site. It is of extreme importance that these sequences are sufficiently long and sufficiently homologous to integrate the sequence into the target site. Preferably, the targeting sequences include at least 100 contiguous nucleotides of SEQ ID NO:1 at one side of the gene of interest and at least 100 contiguous nucleotides of SEQ ID NO:2 at the other side. More preferably, the targeting sequences consist of at least 500 contiguous nucleotides of SEQ ID NO:1 at one side of the gene of interest and at least 500 contiguous nucleotides of SEQ ID NO:2 at the other side. Most preferably, the targeting sequences consist of SEQ ID NO:1 at one side of the gene of interest and SEQ ID NO:2 at the other side, or the targeting sequences consist of at least 100 nucleotides that are at least 80% identical, preferably 90% identical to a region of SEQ ID NO:1 at one side of the gene of interest and at least 100 nucleotides that are at least 80% identical, preferably 90% identical to a region of SEQ ID NO:2 at the other side of the gene of interest. Preferably, the targeting sequences consist of at least 500 nucleotides that are at least 80% identical, preferably 90% identical to a region of SEQ ID NO:1 at one side of the gene of interest and at least 500 nucleotides that are at least 80% identical, preferably 90% identical to a region of SEQ ID NO:2 at the other side of the gene of interest. Most preferably, the targeting sequences consist of at least 1000 nucleotides that are at least 80% identical, preferably 90% identical to a region of SEQ ID NO:1 at one side of the gene of interest and at least 1000 nucleotides that are at least 80% identical, preferably 90% identical to a region of SEQ ID NO:2 at the other side of the gene of interest. The percentage identity is measured with BLAST, according to Altschul et al. (1997). A preferred example of a sequence homologous to SEQ ID NO:1 is given in SEQ ID NO:7. For the purpose of the invention, SEQ ID NO:1 and SEQ ID NO:7 are interchangeable.

Transformation methods of *Lactococcus* are known to the person skilled in the art and include, but are not limited to, protoplast transformation and electroporation.

A transformed *Lactococcus* sp. strain according to the invention is useful for the delivery of prophylactic and/or therapeutic molecules and can be used in a pharmaceutical composition. The delivery of such molecules has been disclosed, as a nonlimiting example, in PCT International Publication Numbers WO 97/14806 and WO 98/31786. Prophylactic and/or therapeutic molecules include, but are not limited to, polypeptides such as insulin, growth hormone, prolactin, calcitonin, group 1 cytokines, group 2 cytokines and group 3 cytokines and polysaccharides such as polysaccharide antigens from pathogenic bacteria. A preferred embodiment is the use of a *Lactococcus* sp. strain according to the invention to deliver human Interleukin-10. This strain can be used in the manufacture of a medicament to treat Crohn's disease as indicated herein.

The invention is further explained with the use of the following illustrative examples.

EXAMPLES

From *L. lactis* MG1363 (Gasson, 1983) regions flanking the sequence according to Ross et al. (1990a) have been cloned.

The knowledge of these sequences is of critical importance for the genetic engineering of any *Lactococcus* strain in a way as described below, as the strategy will employ double homologous recombination in the areas of 1000 bp at the 5' end (SEQ ID NO:1) and 1000 bp at the 3' end (SEQ ID NO:2) of thyA, the "thyA target." These sequences are not available from any public source to date. These flanking DNA fragments have been cloned and their sequence has been identified. The sequence of the whole locus is shown in SEQ ID NO:3; a mutant version of this sequence is shown in SEQ ID NO:5. Both the 5' and 3' sequences are different from the sequence at GenBank AE006385 describing the *L. lactis* IL1403 sequence. (Bolotin, in press) or at AF336368 describing the *L. lactis* subsp. *lactis* CHCC373 sequence. From the literature, it is apparent that homologous recombination by use of the published sequences adjacent to thyA (Ross et al., 1990a) (86 bp at the 5' end and 31 bp at the 3' end) is virtually impossible due to the shortness of the sequences. Indeed, Biswas et al. (1993) describe a logarithmically decreasing correlation between the length of the homologous sequences and the frequency of integration. The sequences of *L. lactis* Thy 11, Thy 12, Thy 15 and Thy 16 at the thyA locus as determined in the present invention are given by SEQ ID NOS:19, 20, 21, 22 respectively.

The thyA replacement is performed by making suitable replacements in a plasmid-borne version of the thyA target, as described below. The carrier plasmid is a derivative of pORI19 (Law et al., 1995), a replication-defective plasmid, which only transfers the erythromycin resistance to a given strain when a first homologous recombination, at either the 5' 1000 bp or at the 3' 1000 bp of the thyA target. A second homologous recombination at the 3' 1000 bp or at the 5' 1000 bp of the thyA target yields the desired strain.

The thyA gene is replaced by a synthetic gene encoding a protein which has the *L. lactis* Usp45 secretion leader (van Asseldonk et al., 1990) fused to a protein of an identical amino-acid sequence when: (a) the mature part of human-Interleukin 10 (hIL-10) or (b) the mature part of hIL-10 in which proline at position 2 has been replaced with alanine or (c) the mature part of hIL-10 in which the first two amino acids have been deleted; (a), (b) and (c) are called hIL-10 analogs, the fusion products are called Usp45-hIL-10.

The thyA gene is replaced by an expression unit comprising the lactococcal P1 promoter (Waterfield et al., 1995), the *E. coli* bacteriophageT7 expression signals, putative RNA stabilizing sequence and modified gene10 ribosomal binding site (Wells and Schofield, 1996).

At the 5' end, the insertion is performed in such way that the ATG of thyA is fused to the P1-T7Usp45-hIL-10 expression unit.

5' agataggaaaatttcatgacttacgcagatcaagttttt...thyA wild-type (SEQ ID NO: 27)

gattaagtcatcttacctctt...P1-T7-usp45-hIL10 (SEQ ID NO: 14)

5' agataggaaaatttcatggattaagtcatcttacctctt...thyA$^-$, P1-T7-usp45-hIL10 (SEQ ID NO: 15)

Alternatively, at the 5' end, the insertion is performed in such a way that the thyA ATG is not included:

5' agataggaaaatttcacttacgcagatcaagttttt...thyA wild-type (SEQ ID NO: 28)

gattaagtcatcttacctctt...P1-T7-usp45-hIL10 (SEQ ID NO: 14)

5' agataggaaaatttcgattaagtcatcttacctctt...thYA$^-$,P1-T7-usp45-hIL10 (SEQ ID NO: 16)

Alternatively, at the 5' end, the insertion is performed in such a way that the thyA promoter (Ross, 1990 a) is not included:

5' tctgagaggttattttgggaaatactattgaaccatatcgaggtgtgtggtataatgaagggaattaaaaa gataggaaaatttcatg...thyA wild-type (SEQ ID NO: 29)

gattaagtcatcttacctctt...P1-T7-usp45-hIL10 (SEQ ID NO: 29)

5' tctgagaggttattttgggaaatactagattaagtcatcttacctctt...thyA$^-$,P1-T7-usp45-hIL10 (SEQ ID NO: 14)

At the 3' end, an ACTAGT SpeI restriction site was engineered immediately adjacent to the TAA stop codon of the usp45-hIL-10 sequence. This was ligated in a TCTAGA XbaI restriction site, which was engineered immediately following the thyA stop codon aaaatccgtaactaactagt 3'...usp45-hIL10 (SEQ ID NO: 30)

gatttagcaatttaaattaaattaatctataagtt 3'...thyA-wild-type (SEQ ID NO: 31)

tctagaattaatctataagttactga 3'...engineered thyA target (SEQ ID NO: 32)

aaaatccgtaactaactaga attaatctataagttactga 3'...thyA$^-$,usp45-hIL10 (SEQ ID NO: 18)

Figure 1:
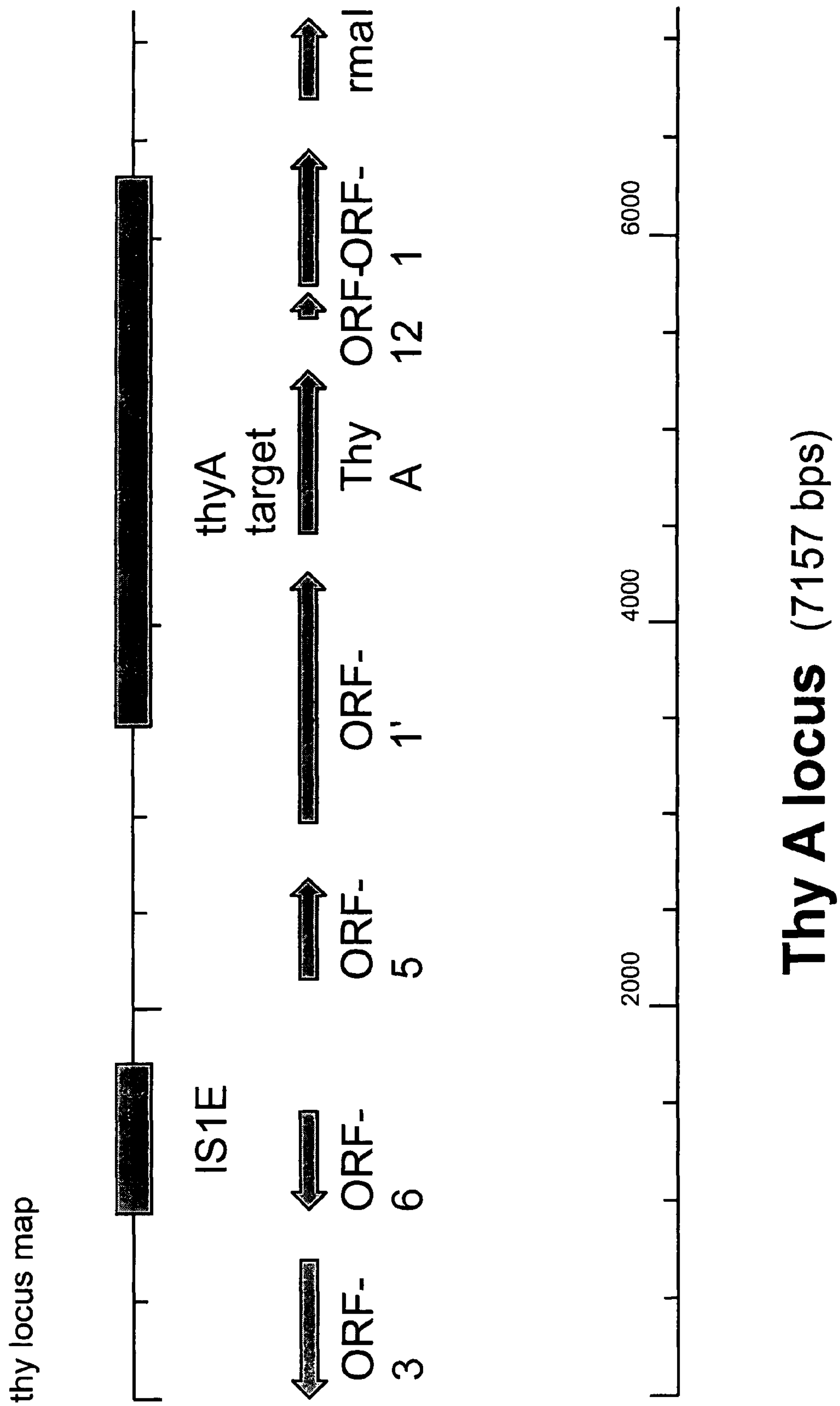
FIG. 1: Map of the MG1363 thyA locus.
Figure 2:
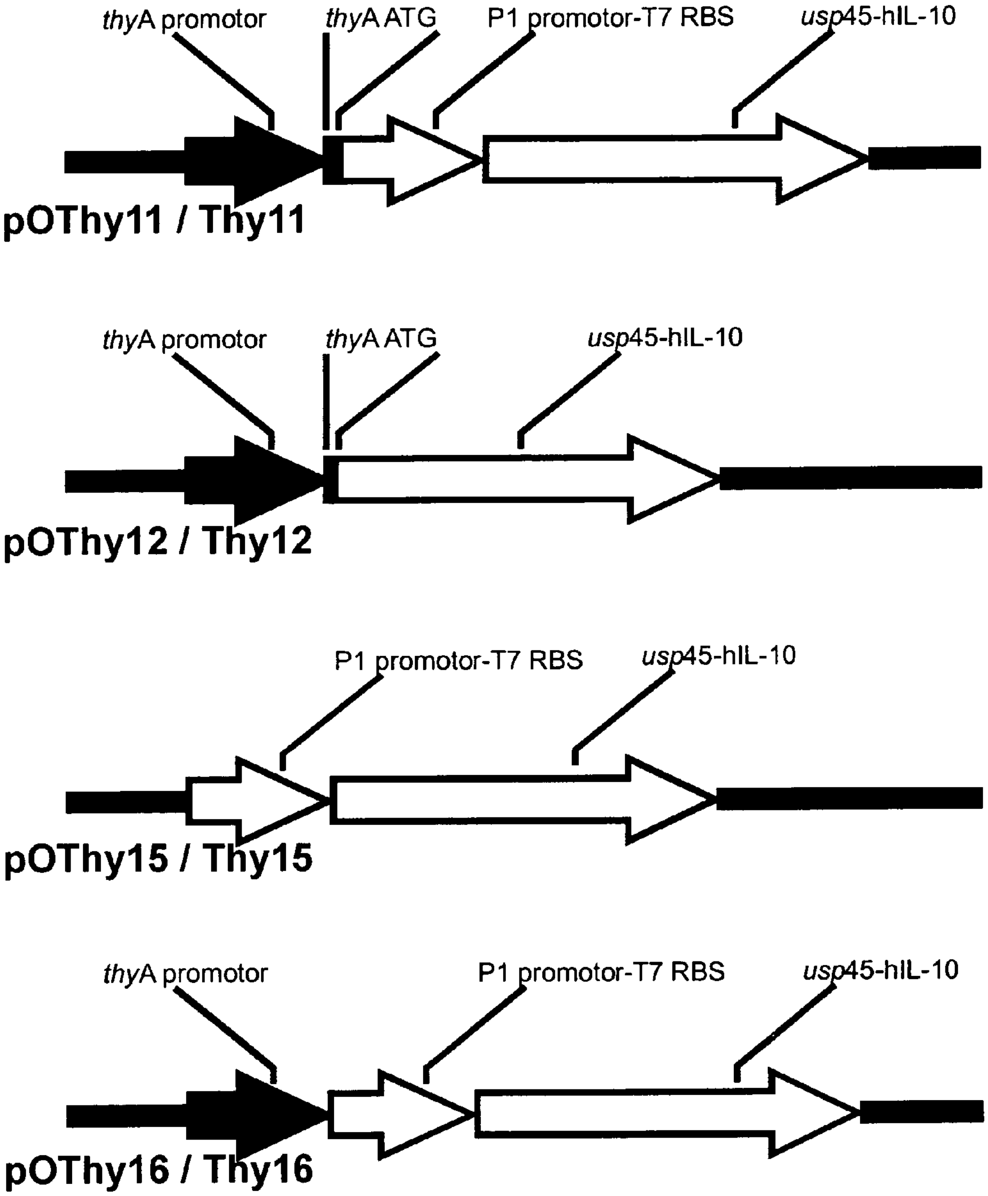
FIG. 2: Schematic representation of the different expression modules as present on pOThy plasmids ands genomic integrants of hIL-10. Black parts represent original *L. lactis* MG1363 genetic information; white parts represent recombinant genetic information.
Figure 3A:
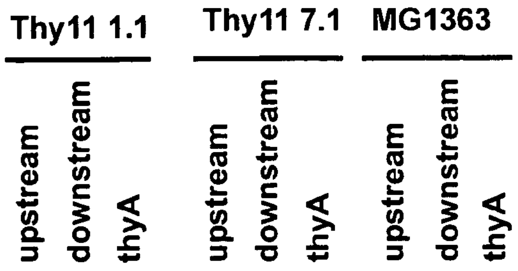
FIGS. 3A and 3B: PCR identification of Thy11 (Thy11 1.1 and Thy11 7.1 represent individually obtained, identical clones). Standard PCR reactions were performed by using aliquots of saturated cultures of the indicated strains as a source of a DNA template.
Figure 3B:
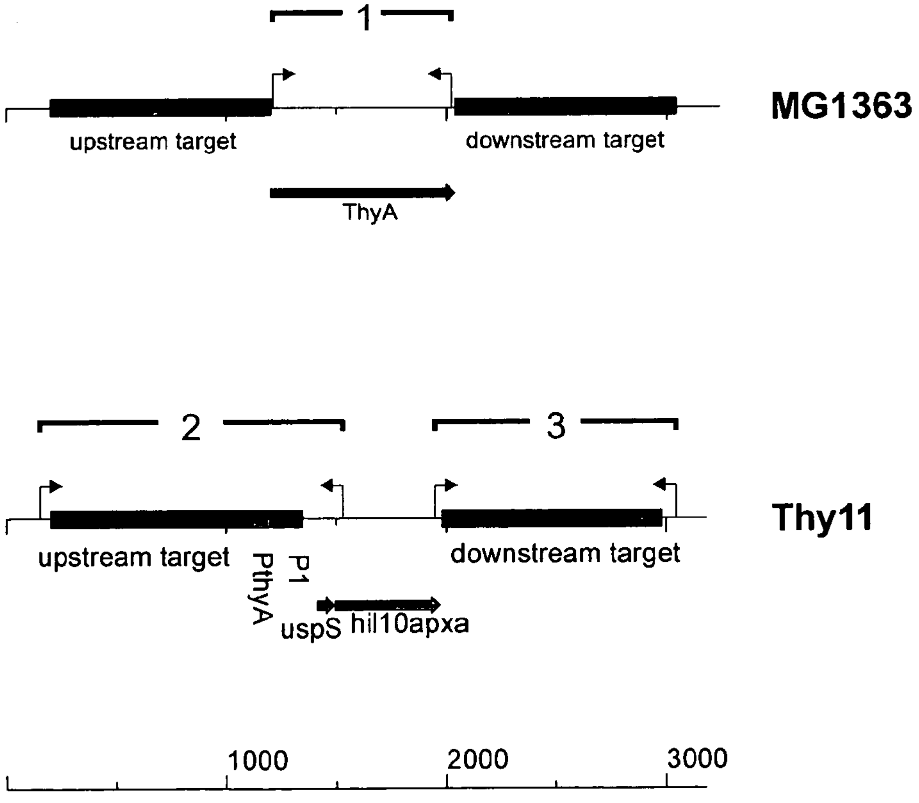

These constructs are depicted in FIG. 2. The sequences of pOThy11, pOThy12 pOThy15 and pOThy16 are given by SEQ ID NOs: 23, 24, 25, and 26 respectively. The resulting strains are thyA deficient, a mutant not yet described for *L. lactis*. It is strictly dependent upon the addition of thymine or thymidine for growth.

The map of the deletion, as well as the PCR analysis of all the isolates/mutants of the present invention, is shown in FIGS. 3A-4B. The presence of the thymidylate synthase and the Interleukin 10 (IL-10) gene in the wild-type strain and in the independent isolates/mutant was analyzed by Southern analysis as shown in FIGS. 5A-6B. The region around the inserted hIL-10 gene was isolated by PCR and the DNA sequence was verified. The structure is identical to the predicted sequence.

Human Interleukin-10 (hIL-10) production in the mutants was checked by western blot analysis and compared with the parental strain, transformed with pTREX1 as negative control, and the parental strain, transformed with the IL10-producing plasmid pT1HIL10apxa as a positive control (FIG. 7A). The concentration in the culture supernatant was quantified using ELISA. As shown in FIG. 7B, both isolates of the mutant produce a comparable, significant amount of hIL-10, be it far less than the strain, transformed with the nonintegrative plasmid pT1HIL10apxa. FIGS. 8A and 8B further demonstrate that all mutants produce a significant amount of hIL-10.

FIG. 9 shows the production of hIL-10 by the *L. lactis* strains LL108 carrying pOThy11, pOThy12, or pOThy16. Quantification (by ELISA) of hIL-10 present in the culture supernatant of the indicated strains is shown. The N-terminal protein sequence of the recombinant hIL-10 was determined by Edman degradation and was shown to be identical to the structure as predicted for the mature, recombinant hIL-10. The protein showed full biological activity. LL108 is an *L. lactis* strain carrying a genomic integration of the repA gene, required for replication of pORI19 derived plasmids such as pOThy11, pOThy12, pOThy15 or pOThy16. This strain was kindly donated by Dr. Jan Kok, University of Groningen, The Netherlands. The plasmids pOThy11, pOThy12, pOThy15 and pOThy16 carry the synthetic human IL-10 gene in different promoter configurations (see FIG. 2), flanked by approximately 1 kB of genomic DNA derived from the thyA locus, upstream and downstream from thyA. These plasmids were used for the construction of the genomic integration as described.

The effect of the thymidylate synthase deletion on the growth in thymidine less and thymidine-supplemented media was tested; the results are summarized in FIGS. 10 and 11. An absence of thymidine in the medium strongly limits the growth of the mutant and even results in a decrease of colony-forming units after four hours of cultivation. The addition of thymidine to the medium results in an identical growth curve and amount of colony-forming units, compared to the wild-type strain, indicating that the mutant does not affect the growth or viability in thymidine-supplemented medium. FIG. 11 clearly demonstrates that Thy12 viability is severely impaired in the absence of thymidine.

FIG. 12 finally shows that *L. lactis* Thy12 passes through the intestine of the mice at the same speed as MG1363. Loss of viability does not appear to differ between Thy12 and MG1363. Thy12 appears fully dependent on thymidine for growth, indicating that no Thy12 bacteria had taken up a foreign thyA gene.

REFERENCES

Altschul, S. F., Madden, T. L., Schaffer, A. A., Zhang, J., Zhang, Z., Miller, W. and Lipman D. J. (1997). Gapped BLAST and PSI-BLAST: a new generation of protein database search programs. *Nucleic Acids Res.* 25, 3389-3402.

Biswas, I., Gruss, A., Ehrlich, S. D. et al. (1993) High-efficiency gene inactivation and replacement system for gram-positive bacteria. *J. Bacteriol.* 175, 3628-3635.

Gasson, M. J. (1983). Plasmid complements of *Streptococcus lactis* NCDO 712 and other lactic streptococci after protoplast-induced curing. *J Bacteriol.* 154, 1-9.

Kaplan, D. L., Mello, C., Sano, T., Cantor, C. and Smith, C. (1999). Streptavidin-based containment system for genetically engineered microorganisms. *Biomol. Eng.* 31, 135-140.

Knudsen, S., Saadbye, P., Hansen, L. H., Collier, A., Jacobsen, B. L., Schlundt, J. And Karlstrom, O. H. (1995). Development and testing of improved suicide functions for biological containment of bacteria. *Appl. Environ. Microbiol.* 61, 985-991.

Law, J., Buist, G., Haandrikman, A. et al. (1995). A system to generate chromosomal mutations in *Lactococcus lactis* which allows fast analysis of targeted genes. *J Bacteriol.* 177, 7011-7018.

Molina, L., Ramos, C., Ronchel, M. C., Molin, S. and Ramos, J. L. (1998). Construction of an efficient biologically contained *Pseudomonas putida* strain and its survival in outdoor assays. *Appl. Environ. Microbiol.* 64, 2072-2078.

Ross, P., O'Gara, F. and Condon, S. (1990a). Cloning and characterization of the thymidylate synthase gene from *Lactococcus lactis* subsp. *Lactis. Appl. Environ. Microbiol.* 56, 2156-2163.

Ross, P., O'Gara, F. and Condon, S. (1990b). Thymidylate synthase gene from *Lactococcus lactis* as a genetic marker: an alternative to antibiotic resistance. *Appl. Environ. Microbiol* 56, 2164-2169.

Schweder, T., Hofinann, K. And Hecker, M. (1995). *Escherichia coli* K12 relA strains as safe hosts for expression of recombinant DNA. *Appl. Environ. Microbiol.* 42, 718-723.

Steidler, L., Hans, W., Schotte, L., Neirynck, S., Obermeier, F., Falk, W., Fiers, W. and Remaut, E. (2000). Treatment of murine colitis by *Lactococcus lactis* secreting Interleukin-10. *Science* 289, 1352-1355.

Steidler, L., Wells, J. M., Raeymaekers, A., Vandekerckhove, J., Fiers, W. And Remaut, E. (1995). Secretion of biologically active murine Interleukin-2 by *Lactococcus lactis* subsp. *Lactis. Appl. Environ. Microbiol.* 61, 1627-1629.

Tedin, K. Witte, A., Reisinger, G., Lubitz, W. and Basi, U. (1995). Evaluation of the *E. coli* ribosomal rrnB P1 promoter and phage derived lysis genes for the use in biological containment system: a concept study. *J. Biotechnol.* 39, 137-148.

van Asseldonk, M., Rutten, G., Oteman, M. et al. (1990). Cloning of usp45, a gene encoding a secreted protein from *Lactococcus lactis* subsp. *lactis* MG1363. *Gene* 95, 155-160.

Waterfield, N. R., Le Page, R. W., Wilson, P. W. et al. (1995) The isolation of lactococcal promoters and their use in investigating bacterial luciferase synthesis in *Lactococcus lactis. Gene* 165, 9-15.

Wells, J. M. and Schofield, K. M. (1996) Cloning and expression vectors for Lactococci. *Nato ASI series* H98, 37-62.

What is claimed is:

1. An isolated thymidylate synthase (thyA) mutant of a parent strain of *Lactococcus* species, said thyA mutant comprising:

an inactive *Lactococcus* thymidylate synthase gene; and a gene encoding a heterologous therapeutic molecule;

wherein said parent strain comprises SEQ ID NO: 3 and or SEQ ID NO: 5, wherein the thyA mutant expresses the heterologous therapeutic molecule.

2. The isolated thymidylate synthase (thyA) mutant of a parent strain of *Lactococcus* species of claim 1, wherein said (thyA) mutant is transformed with a transforming plasmid, wherein said transforming plasmid does not encode an active thymidylate synthase.

3. The isolated thymidylate synthase (thyA) mutant of a parent strain of *Lactococcus* species of claim 2, wherein the transforming plasmid comprises the gene encoding a heterologous therapeutic molecule.

4. The isolated thymidylate synthase (thyA) mutant of a parent strain of *Lactococcus* species of any one of claims 2, 3, or 1, wherein the *Lactococcus* species is *Lactococcus lactis*.

5. The isolated thymidylate synthase (thyA) mutant of a parent strain of *Lactococcus* species of any one of claim 2, 3, or 1, wherein the gene encoding a heterologous therapeutic molecule encodes Interleukin-10.

6. The isolated thymidylate synthase (thyA) mutant of a parent strain of *Lactococcus* species of any one of claims 2, 3, or 1, wherein the gene encoding a heterologous therapeutic molecule encodes Interleukin-10 and wherein the *Lactococcus* species is *Lactococcus* lactis.

7. An isolated thymidylate synthase (thyA) mutant of a parent strain of *Lactococcus* species, the thyA mutant comprising:

an inactive *Lactococcus* thymidylate synthase gene and a gene encoding a heterologous therapeutic molecule, wherein the inactive *Lactococcus* thymidylate synthase gene has been inactivated by gene disruption;

wherein the parent strain of *Lactococcus* species comprises:

SEQ ID NO: 3 or SEQ ID NO: 5, and wherein the thyA mutant expresses the heterologous therapeutic molecule.

8. An isolated thymidylate synthase (thyA) mutant of a parent strain of *Lactococcus* species, wherein the thyA mutant lacks active *Lactococcus* thymidylate synthase gene and comprises a gene encoding a heterologous therapeutic molecule, wherein the thyA mutant expresses the heterologous therapeutic molecule, and wherein the thyA mutant is produced by a process comprising:

providing a parent strain of *Lactococcus* species comprising a thymidylate synthase gene comprising wherein said *Lactococcus* thymidylate synthase gene comprises SEQ ID NO: 3 or SEQ ID NO: 5; and altering by gene disruption the *Lactococcus* thymidylate synthase gene of the parent strain so as to inactivate the thymidylate synthase encoded thereby.

9. The isolated thymidylate synthase (thyA) mutant of a parent strain of *Lactococcus* species according to claim 8, wherein the gene encoding the heterologous therapeutic molecule is integrated within, or replaces at least a part of the thymidylate synthase gene of said parent strain.

10. The isolated thymidylate synthase (thyA) mutant of a parent strain of *Lactococcus* species according to claim 8, wherein said (thyA) mutant is transformed with a transforming plasmid, wherein said transforming plasmid does not encode an active thymidylate synthase.

11. The isolated thymidylate synthase (thyA) mutant of a parent strain of *Lactococcus* species according to claim 10, wherein the transforming plasmid comprises the gene encoding a heterologous therapeutic molecule.

12. The isolated thymidylate synthase (thyA) mutant of a parent strain of *Lactococcus* species according to any of claims 8, 9, 10 or 11, wherein the *Lactococcus* species is *Lactococcus* lactis.

13. The isolated thymidylate synthase (thyA) mutant of a parent strain of *Lactococcus* species according to any of claims 8, 9, 10, or 11, wherein the gene encoding a heterologous therapeutic molecule encodes Interleukin-10.

14. The isolated thymidylate synthase (thyA) mutant of a parent strain of *Lactococcus* species according to any of claims 8, 9, 10, or 11, wherein the gene encoding a heterologous therapeutic molecule encodes Interleukin-10 and wherein the *Lactococcus* species is *Lactococcus* lactis.

15. A composition comprising:

the isolated thymidylate synthase (thyA) mutant of claim 1.

16. The composition of claim 15, wherein said (thyA) mutant is transformed with a transforming plasmid, wherein said transforming plasmid does not encode an active thymidylate synthase.

17. The composition of claim 16, wherein the transforming plasmid comprises the gene encoding a heterologous therapeutic molecule.

18. The composition of any of claim 15, 17, or 16, wherein the gene encoding a heterologous therapeutic molecule encodes Interleukin-10.

19. The composition of any of claim 15, 17, or 16, wherein said *Lactococcus* species is *Lactococcus* lactis.

20. The composition of any of claim 15, 17, or 16, wherein the gene encoding a heterologous therapeutic molecule encodes Interleukin-10 and wherein said *Lactococcus* species is *Lactococcus* lactis.

21. A method for delivering a heterologous therapeutic molecule to a subject, said method comprising administering the transformed strain of *Lactococcus* species of any of claims 1, 7, and 8 to the subject.

22. A method for delivering a heterologous molecule to a human subject, the method comprising administering the *Lactococcus* species of any of claims 1, 7, and 8 to the human subject.

23. A method of treating inflammatory bowel disease in a subject, said method comprising:

administering to the subject a transformed strain of *Lactococcus* species of any of claims 1, 7, and 8.

24. The method of claim 23, wherein the gene encoding a heterologous therapeutic molecule encodes Interleukin-10.

* * * * *

UNITED STATES PATENT AND TRADEMARK OFFICE

CERTIFICATE OF CORRECTION

PATENT NO. : 7,780,961 B2
APPLICATION NO. : 10/687996
DATED : August 24, 2010
INVENTOR(S) : Lothar Steidler It is certified that error appears in the above-identified patent and that said Letters Patent is hereby corrected as shown below:

On the title page:
In ITEM (56) References Cited
OTHER PUBLICATIONS
Page 2, 1st column, 3rd line of the 5th entry (line 16), change "1951.57," to --1951-57,--

In the claims:

CLAIM 1, COLUMN 81, LINE 17, change "3 and or" to --3 or--

CLAIM 8, COLUMN 81, LINES 58,59 change "comprising wherein said *Lactococcus* thymidylate synthase gene comprises" to --comprising--

Signed and Sealed this
Sixteenth Day of April, 2013

Teresa Stanek Rea
*Acting Director of the United States Patent and Trademark Office*

SEQUENCE LISTING

<160> NUMBER OF SEQ ID NOS: 32

<210> SEQ ID NO 1
<211> LENGTH: 1000
<212> TYPE: DNA
<213> ORGANISM: Lactococcus lactis

<400> SEQUENCE: 1

```
tatatacaat tgagcaaaag aaatttagtt attaaattac cagctggagt tcctccaatg      60
gttgtagatt cactaagtcc agcaattatt tcaatggtga ttttctgttt gatgttcggg     120
attcgtgtgg gattctctta tacgccattc catgatattt tcaatttctc aacacaacta     180
attcaagcac cgttgactgg tgctgtggca aatccatggg ttcttatggg catctttacc     240
tttggtaatt tcttatggtt ctttggtatc caccctaatt taattggggg aattttaaat     300
ccattgttat taacaatgtc atatgctaat attgatgcct atgctgccgg aaaacctgta     360
ccatacttac aaatgatgat tgtgtttgct gtgggtgcga acgcatgggg cggaagtgga     420
aatacttatg ggttagttat ttcaatgttt acggcaaaat ctgaacgcta taaacaatta     480
ttaaaattag gtgcaattcc tagtattttc aatatcagtg aaccattact ttttggtctt     540
ccaatgatgt taaatcctct tttctttatt cctttggttt tccaaccagc aattttagga     600
actgtagcat tgggcttggc aaagatatta tatattacaa atctgaatcc aatgacggca     660
cttcttcctt ggacgacacc agcacctgtg agaatggcca tttcaggtgg acttccattt     720
ttgattattt ttgcaatctg tttagtcttg aatgttctta tttactaccc attctttaag     780
gtggcgtata ataaagcttt agaagaagaa aaagcagctg ttgaattaga gggttcagaa     840
actgcctgat ggatattttt tataaatctg gtttgaacaa attatattga catctctttt     900
tctatcctga taattctgag aggttatttt gggaaatact attgaaccat atcgaggtgt     960
gtggtataat gaagggaatt aaaaaagata ggaaaatttc                          1000
```

<210> SEQ ID NO 2
<211> LENGTH: 1000
<212> TYPE: DNA
<213> ORGANISM: Lactococcus lactis

<400> SEQUENCE: 2

```
taaattaatc tataagttac tgacaaaact gtcagtaact ttttttgtgg gaaaaatgta      60
tttttatgac cgtaaagaat ctgtcagtag aagtctgaaa ttcgtttaaa aatcgactag     120
aataggcttt aacgacaaga tgttttaaag agtacgctct aaatgtattt ttgtattttt     180
gtttgattac gaagtttaaa tttaattgac aaatgtttta aaatgagtat aataggactt     240
gtaaccgatt ttatttttat aaaggagaaa gaaagatgaa caaactttta cttggaacag     300
cctttatagg ggctagctta ctgattggtg ggggtgctca tgcagatcaa atgtttatcg     360
tttgtataat cataatactg gtgagcactc tatacaacta gtgggacacc aaaagaatgc     420
taatgtaagt gcgggttgga cttatgaagg tgtcggttgg atcgcaccaa caacaagttc     480
aagcccagtt taccgtgtgt acaatccaaa tgcattatta cacaaaaagc aagtatgaag     540
cccaaagttt agtaaataag ggttggaaat gggataataa cggaaaggcg gtcttctatt     600
ctggaggttc tcaagccgta tatgtcgctt ataatcccaa tgcacaatct ggcgctcaca     660
attacacgga aagtagcttt gagcaaaata gcttattgaa tactggttgg aaatatgggg     720
cagtagcttg gtacgggatt ggagtaaaaa acgaaatgtt aaacattgct caaattgtta     780
```

-continued

```
gtggtaattt ttctagtatt gttggaactt ggaaagatac ttctggaaat atgcttgaaa    840

ttaatgcaat gggaaatctt actttaatat ggaaaggggc aaagaatcaa acctttgaac    900

ttggcgcagg tcaacaattt aatggaactg cagatattgc cttaaaaaat ggagagattt    960

cccctggtag tccacttaac atttttgttg taccaacaga                         1000
```

<210> SEQ ID NO 3
<211> LENGTH: 7157
<212> TYPE: DNA
<213> ORGANISM: Lactococcus lactis
<220> FEATURE:
<221> NAME/KEY: CDS
<222> LOCATION: (4473)..(5312)
<223> OTHER INFORMATION:
<220> FEATURE:
<221> NAME/KEY: misc_feature
<222> LOCATION: (2)..(2)
<223> OTHER INFORMATION: 'n' may be any base
<220> FEATURE:
<221> NAME/KEY: misc_feature
<222> LOCATION: (5)..(5)
<223> OTHER INFORMATION: 'n' may be any base
<220> FEATURE:
<221> NAME/KEY: misc_feature
<222> LOCATION: (6612)..(6612)
<223> OTHER INFORMATION: 'n' may be any base
<220> FEATURE:
<221> NAME/KEY: misc_feature
<222> LOCATION: (7099)..(7099)
<223> OTHER INFORMATION: 'n' may be any base
<220> FEATURE:
<221> NAME/KEY: misc_feature
<222> LOCATION: (7110)..(7110)
<223> OTHER INFORMATION: 'n' may be any base
<220> FEATURE:
<221> NAME/KEY: misc_feature
<222> LOCATION: (7117)..(7141)
<223> OTHER INFORMATION: 'n' may be any base
<220> FEATURE:
<221> NAME/KEY: misc_feature
<222> LOCATION: (7143)..(7147)
<223> OTHER INFORMATION: 'n' may be any base
<220> FEATURE:
<221> NAME/KEY: misc_feature
<222> LOCATION: (7149)..(7156)
<223> OTHER INFORMATION: 'n' may be any base

<400> SEQUENCE: 3

```
gnagnggttt tcccagtccg acgttgtaaa acgacggcca gtgaattcat taacagcctt     60

ttgagcagct agctcattat tttgaaataa atcataaatt tctttcccac tatctgattt    120

atgattgcta gcatatttgt tgtataatcg aacgagtcca ttttgaacag atccatatag    180

attgagtgaa ctataaaata catctatatc atagttgagt ttgttcacaa tcatgagacc    240

aaattctcca gcatttcgtg tagaaccacg ataaagctgt ttatttagca aaatggcacc    300

tccgacacct gtacctaaag tcatgcaaat aaaattttgg ctttcttgtc cattccctag    360

ccaaagttca gctagacctg cacaattggc atcattttca acataaaccg gaagatttaa    420

atgtttttgt agttctgtcc ccaatggata gccataaaga tcagttagag ctcctgccag    480

taataatgtt ccctttttgt cagaagttcc gggaacactt acaccaattg cagatactga    540

atgatgagct tttaactgat gaatatttgt gagcaagcta tccataattt tttcttttt    600

taatggggtt ggaacttgta aatgttgtat gatcgttcca tcactagtta caagaccaaa    660

ttttataaat gtaccaccga tatcaattcc tattgaataa tgcatctttt attacctctt    720

tctctaattt gttttagtat agcaaaatca aaaaattaat tatggtatgc attatagata    780

tgttgtataa ttttcacaaa aacggagaaa actatgaaaa caatagaaca gctcatgata    840
```

-continued

```
gattcagcag atttaatgtc agattttatt caattgacaa tttttatatt ccgcaaggag    900
gattttcaac ttttttatag gagtgatgaa gaagagcaag ctttttcaag gtaatgactc    960
caacttattg atagtgtttt atgttcagat aatgcccgat gactttgtca tgcagctcca   1020
ccgattttga gaacgacagc gacttccgtc ccagccgtgc caggtgctgc ctcagattca   1080
ggttatgccg ctcaattcgc tgcgtatatc gcttgctgat tacgtgcagc tttcccttca   1140
ggcgggattc atacagcggc cagccatccg tcatccatat caccacgtca aagggtgaca   1200
gcaggctcat aagacgcccc agcgtcgcca tagtgcgttc accgaatacg tgcgcaacaa   1260
ccgtcttccg gagactgtca tacgcgtaaa acagccagcg ctggcgcgat ttagccccga   1320
catagcccca ctgttcgtcc atttccgcgc agacgatgac gtcactgccc ggctgtatgc   1380
gcgaggttac cgactgcggc ctgagttttt taagtgacgt aaaatcgtgt tgaggccaac   1440
gcccataatg cgggctgttg cccggcatcc aacgccattc atggccatat caatgatttt   1500
ctggtgcgta ccgggttgag aagcggtgta agtgaactgc agttgccatg ttttacggca   1560
gtgagagcag agatagcgct gatgtccggc ggtgcttttg ccgttacgca ccaccccgtc   1620
agtagctgaa caggagggac agctgataga aacagaagcc actggagcac ctcaaaaaca   1680
ccatcataca ctaaatcagt aagttggcag catcaccctt tttcaaaaga aatcatcgct   1740
catttatctc agttgccctt gaaggaagag gtgaatttat tttatatgcc taagataaaa   1800
ggatatatta cttatttttc tgtatttggt aaagaggagt atcttctact tatttttaaa   1860
ggacaagaaa aacttgcaaa taatcctttc cccgttgaag taaaacaatt attaaaaagt   1920
ggtattttac tctatcaaat gatttttcaa gaaaaattag attatgaaga attatttgag   1980
aaaaatcagc atattatttc tccattgctt gctgctaaac caattgaatg gaatgattcc   2040
aatacgtgag gaaagtaaat tcccataaaa catatctttt tgaaaaatat ttgggggaat   2100
gtgttattcg tggagatgtt gcagagttaa aaaaagcttt ttcaaattat atgaataaag   2160
gaactgctgg aaaattatct aataattcaa tgcgacataa gaaaaacatt ttgatttcag   2220
tcatcactat gactactcgt tcggctatac agggaggatt acctgaagaa gaagcttttt   2280
tgatgagtga tttatatatt caagagcttg aagaattaac ggaattagaa gaaattagaa   2340
cgcttgccta taatgtgatg atcgattttg cagataaagt gaaacagcat cgatattgtc   2400
aggtttctta taaaatatta tcttgtcaaa agtatattgt taatcattta tacgaaaaac   2460
taagtgtgag tgaaattgca gaagagctac acatgaatat ttcttattta tcttcacaat   2520
tcaaaaaaga gacagggcaa acaattacaa actttattca ggagaagcga atagaagaag   2580
ctagagaatt aatccttttc tcagactatc ctttttcaag aatttatacc ttgttggttt   2640
tactgccaaa gtcattttat aaaaatattt aaaaaatata ctggaataac tcccaaaaag   2700
tttcaagatc agtatattta tcatgcctct acatcaatat atgattgaaa ttaaaaaaag   2760
acctagaatt tcaaaattga taaaatacat acctaaaata ttaattctgt actattacgg   2820
gtggagtatc tactgtataa tgagggtata aattatggaa gaagggagta aaactaaatt   2880
tattgatggt tttacgaatt aattaggata tttttttaa aaaccaaaga aaacgcttac    2940
aaacgttaaa ggagtgaatc taaagatgga caaatttgaa aaatggctaa ataagacctt   3000
gatgccactt gcctcaaaaa tgaataaaaa tcatttcatt tcggcattaa gtgaagcatt   3060
tatgagatgt atgcccttaa cattagggat tgcattattg acaattatag gatactttcc   3120
agttcctgcc tgggtagatt tcttaaactc tattggactg gctcagcatt tttcagcagt   3180
tattggtgca gttaccagtg cgctagcaat ttatgtaact tataattttg cttattctta   3240
```

-continued

```
tgtaaatcgt catgaatata atggccatac ggccggttta ttatcaatcg caagtttgtt   3300

aatgctaatg ccacaaatta ttactgtccc tgtagtaaaa aacattccaa ccgaatttcc   3360

gaaatccgcg gtagttgaca gtgtgtcaaa tgttgaagca tttcaaacgg tatacacggg   3420

tagcacagga ttaattgtag caatcataat tggttttatt gtttcattag tctatataca   3480

attgagcaaa agaaatttag ttattaaatt accagctgga gttcctccaa tggttgtaga   3540

ttcactaagt ccagcaatta tttcaatggt gattttctgt ttgatgttcg ggattcgtgt   3600

gggattctct tatacgccat tccatgatat tttcaatttc tcaacacaac taattcaagc   3660

accgttgact ggtgctgtgg caaatccatg ggttcttatg ggcatcttta cctttggtaa   3720

tttcttatgg ttctttggta tccaccctaa tttaattggg ggaattttaa atccattgtt   3780

attaacaatg tcatatgcta atattgatgc ctatgctgcc ggaaaacctg taccatactt   3840

acaaatgatg attgtgtttg ctgtgggtgc gaacgcatgg ggcggaagtg gaaatactta   3900

tgggttagtt atttcaatgt ttacggcaaa atctgaacgc tataaacaat tattaaaatt   3960

aggtgcaatt cctagtattt tcaatatcag tgaaccatta ctttttggtc ttccaatgat   4020

gttaaatcct cttttcttta ttcctttggt tttccaacca gcaattttag gaactgtagc   4080

attgggcttg gcaaagatat tatatattac aaatctgaat ccaatgacgg cacttcttcc   4140

ttggacgaca ccagcacctg tgagaatggc catttcaggt ggacttccat tttgattat   4200

ttttgcaatc tgtttagtct tgaatgttct tatttactac ccattcttta aggtggcgta   4260

taataaagct ttagaagaag aaaaagcagc tgttgaatta gagggttcag aaactgcctg   4320

atggatattt tttataaatc tggtttgaac aaattatatt gacatctctt tttctatcct   4380

gataattctg agaggttatt ttgggaaata ctattgaacc atatcgaggt gtgtggtata   4440

atgaagggaa ttaaaaaaga taggaaaatt tc atg act tac gca gat caa gtt     4493
                                    Met Thr Tyr Ala Asp Gln Val
                                    1               5

ttt aaa caa aat atc caa aat atc cta gat aat ggt gtt ttt tca gaa     4541
Phe Lys Gln Asn Ile Gln Asn Ile Leu Asp Asn Gly Val Phe Ser Glu
        10                  15                  20

aat gca aga cca aag tat aag gat ggt caa atg gcg aat agc aaa tat     4589
Asn Ala Arg Pro Lys Tyr Lys Asp Gly Gln Met Ala Asn Ser Lys Tyr
    25                  30                  35

gtc act ggt tca ttc gtt act tat gat ttg caa aag ggg gag ttt cca     4637
Val Thr Gly Ser Phe Val Thr Tyr Asp Leu Gln Lys Gly Glu Phe Pro
40                  45                  50                  55

att acc act ttg cgt cca att cca atc aaa tct gct att aaa gaa ttg     4685
Ile Thr Thr Leu Arg Pro Ile Pro Ile Lys Ser Ala Ile Lys Glu Leu
                60                  65                  70

atg tgg ata tac caa gac caa aca agt gaa ctt tct gtt ctc gaa gag     4733
Met Trp Ile Tyr Gln Asp Gln Thr Ser Glu Leu Ser Val Leu Glu Glu
            75                  80                  85

aag tat gga gtc aaa tac tgg gga gaa tgg gga att ggt gat ggt acg     4781
Lys Tyr Gly Val Lys Tyr Trp Gly Glu Trp Gly Ile Gly Asp Gly Thr
        90                  95                  100

att ggg caa cgt tat ggt gca aca gtc aaa aaa tat aat atc att ggt     4829
Ile Gly Gln Arg Tyr Gly Ala Thr Val Lys Lys Tyr Asn Ile Ile Gly
    105                 110                 115

aaa tta tta gaa ggc ttg gcc aaa aat cca tgg aat cgt cgt aat atc     4877
Lys Leu Leu Glu Gly Leu Ala Lys Asn Pro Trp Asn Arg Arg Asn Ile
120                 125                 130                 135

atc aac ctt tgg cag tat gaa gat ttt gag gaa aca gaa ggt ctt tta     4925
Ile Asn Leu Trp Gln Tyr Glu Asp Phe Glu Glu Thr Glu Gly Leu Leu
                140                 145                 150
```

-continued

```
cca tgt gct ttc caa acg atg ttt gat gtc cgt cga gaa aaa gat ggt     4973
Pro Cys Ala Phe Gln Thr Met Phe Asp Val Arg Arg Glu Lys Asp Gly
            155                 160                 165

cag att tat ttg gat gcc aca ctg att caa cgt tca aac gat atg ctt     5021
Gln Ile Tyr Leu Asp Ala Thr Leu Ile Gln Arg Ser Asn Asp Met Leu
        170                 175                 180

gta gcc cac cat atc aat gcg atg caa tat gtt gct ttg caa atg atg     5069
Val Ala His His Ile Asn Ala Met Gln Tyr Val Ala Leu Gln Met Met
    185                 190                 195

att gca aaa cat ttt tct tgg aaa gtt ggg aaa ttc ttt tat ttt gta     5117
Ile Ala Lys His Phe Ser Trp Lys Val Gly Lys Phe Phe Tyr Phe Val
200                 205                 210                 215

aat aat tta cat att tat gat aat cag ttt gag cag gca aat gaa tta     5165
Asn Asn Leu His Ile Tyr Asp Asn Gln Phe Glu Gln Ala Asn Glu Leu
                220                 225                 230

atg aag cga aca gct tct gaa aaa gaa cct cgt ttg gtc ctt aat gtt     5213
Met Lys Arg Thr Ala Ser Glu Lys Glu Pro Arg Leu Val Leu Asn Val
            235                 240                 245

cct gat ggt aca aac ttt ttc gat att aaa cct gaa gat ttt gaa ctt     5261
Pro Asp Gly Thr Asn Phe Phe Asp Ile Lys Pro Glu Asp Phe Glu Leu
        250                 255                 260

gtg gac tat gag cca gta aaa cct caa ttg aaa ttt gat tta gca att     5309
Val Asp Tyr Glu Pro Val Lys Pro Gln Leu Lys Phe Asp Leu Ala Ile
    265                 270                 275

taa attaatctat aagttactga caaaactgtc agtaactttt tttgtgggaa          5362

aaatgtattt ttatgaccgt aaagaatctg tcagtagaag tctgaaattc gtttaaaaat   5422

cgactagaat aggctttaac gacaagatgt tttaaagagt acgctctaaa tgtatttttg   5482

tatttttgtt tgattacgaa gtttaaattt aattgacaaa tgttttaaaa tgagtataat   5542

aggacttgta accgatttta tttttataaa ggagaaagaa agatgaacaa acttttactt   5602

ggaacagcct ttataggggc tagcttactg attggtgggg gtgctcatgc agatcaaatg   5662

tttatcgttt gtataatcat aatactggtg agcactctat acaactagtg ggacaccaaa   5722

agaatgctaa tgtaagtgcg ggttggactt atgaaggtgt cggttggatc gcaccaacaa   5782

caagttcaag cccagtttac cgtgtgtaca atccaaatgc attattacac aaaaagcaag   5842

tatgaagccc aaagtttagt aaataagggt tggaaatggg ataataacgg aaaggcggtc   5902

ttctattctg gaggttctca agccgtatat gtcgcttata atcccaatgc acaatctggc   5962

gctcacaatt acacggaaag tagctttgag caaaatagct tattgaatac tggttggaaa   6022

tatggggcag tagcttggta cgggattgga gtaaaaaacg aaatgttaaa cattgctcaa   6082

attgttagtg gtaatttttc tagtattgtt ggaacttgga aagatacttc tggaaatatg   6142

cttgaaatta atgcaatggg aaatcttact ttaatatgga aaggggcaaa gaatcaaacc   6202

tttgaacttg gcgcaggtca acaatttaat ggaactgcag atattgcctt aaaaaatgga   6262

gagatttccc ctggtagtcc acttaacatt tttgttgtac caacagaagt tgctttccct   6322

aataataaaa aagtagacga ttcaactggg caacaacgaa tttttgtgaa ttattctggt   6382

acaagccctc aaatggcgaa tagtatggca gcggtggctt tttttagagt tattccatga   6442

ttatattaaa gttagaattg aataaaatgt attattaaaa agataatatt atatcacgac   6502

aaggcgacat ctatcaactt taccactggt atggaagtga ccattattac atcaggaaac   6562

gctaaaacgg ttgtttttac acccgtaaaa taaataataa aataatgtgn aattactgac   6622

agcattttgt cagtaatttt ttttatcaaa atcacacaaa aatgttcgtt gacgaacaaa   6682

aaaaactatg ttataataat tcgtatgcga actaaaaaag aagcgattgg ccgactttta   6742
```

-continued

```
aaagtagcca gcaaccaaat gtctcgagaa tttgataatt ttgcagctca acttgatttg   6802

acaggtcagc aaatgtcaat tttagatttt cttggaaatc aaagcgaaga aggttcagga   6862

aaagaaatta gtcagacgat gattgaatta gaatttaata tccgacgttc aacaacgacg   6922

gaaattttac agcgcatgga aaagcggctt ttaattaatc gaagaacaag cctgaccgat   6982

gcccgccaaa aatcagttga attaactgaa gaagggaaaa gatatttacc tgaaatcagg   7042

gcttatatcc aagcacataa taaaaaagct tggcgtaatc atggtcatag ctgtttncct   7102

ggttaggngg gccannnnnn nnnnnnnnnn nnncnnnnnc nnnnncnnnn cnnnc        7157
```

<210> SEQ ID NO 4
<211> LENGTH: 279
<212> TYPE: PRT
<213> ORGANISM: Lactococcus lactis
<220> FEATURE:
<221> NAME/KEY: misc_feature
<222> LOCATION: (2)..(2)
<223> OTHER INFORMATION: 'n' may be any base
<220> FEATURE:
<221> NAME/KEY: misc_feature
<222> LOCATION: (5)..(5)
<223> OTHER INFORMATION: 'n' may be any base
<220> FEATURE:
<221> NAME/KEY: misc_feature
<222> LOCATION: (6612)..(6612)
<223> OTHER INFORMATION: 'n' may be any base
<220> FEATURE:
<221> NAME/KEY: misc_feature
<222> LOCATION: (7099)..(7099)
<223> OTHER INFORMATION: 'n' may be any base
<220> FEATURE:
<221> NAME/KEY: misc_feature
<222> LOCATION: (7110)..(7110)
<223> OTHER INFORMATION: 'n' may be any base
<220> FEATURE:
<221> NAME/KEY: misc_feature
<222> LOCATION: (7117)..(7141)
<223> OTHER INFORMATION: 'n' may be any base
<220> FEATURE:
<221> NAME/KEY: misc_feature
<222> LOCATION: (7143)..(7147)
<223> OTHER INFORMATION: 'n' may be any base
<220> FEATURE:
<221> NAME/KEY: misc_feature
<222> LOCATION: (7149)..(7156)
<223> OTHER INFORMATION: 'n' may be any base

<400> SEQUENCE: 4

```
Met Thr Tyr Ala Asp Gln Val Phe Lys Gln Asn Ile Gln Asn Ile Leu
1               5                   10                  15

Asp Asn Gly Val Phe Ser Glu Asn Ala Arg Pro Lys Tyr Lys Asp Gly
            20                  25                  30

Gln Met Ala Asn Ser Lys Tyr Val Thr Gly Ser Phe Val Thr Tyr Asp
        35                  40                  45

Leu Gln Lys Gly Glu Phe Pro Ile Thr Thr Leu Arg Pro Ile Pro Ile
    50                  55                  60

Lys Ser Ala Ile Lys Glu Leu Met Trp Ile Tyr Gln Asp Gln Thr Ser
65                  70                  75                  80

Glu Leu Ser Val Leu Glu Glu Lys Tyr Gly Val Lys Tyr Trp Gly Glu
                85                  90                  95

Trp Gly Ile Gly Asp Gly Thr Ile Gly Gln Arg Tyr Gly Ala Thr Val
            100                 105                 110

Lys Lys Tyr Asn Ile Ile Gly Lys Leu Leu Glu Gly Leu Ala Lys Asn
        115                 120                 125
```

-continued

```
Pro Trp Asn Arg Arg Asn Ile Ile Asn Leu Trp Gln Tyr Glu Asp Phe
    130                 135                 140

Glu Glu Thr Glu Gly Leu Leu Pro Cys Ala Phe Gln Thr Met Phe Asp
145                 150                 155                 160

Val Arg Arg Glu Lys Asp Gly Gln Ile Tyr Leu Asp Ala Thr Leu Ile
                165                 170                 175

Gln Arg Ser Asn Asp Met Leu Val Ala His His Ile Asn Ala Met Gln
            180                 185                 190

Tyr Val Ala Leu Gln Met Met Ile Ala Lys His Phe Ser Trp Lys Val
        195                 200                 205

Gly Lys Phe Phe Tyr Phe Val Asn Asn Leu His Ile Tyr Asp Asn Gln
    210                 215                 220

Phe Glu Gln Ala Asn Glu Leu Met Lys Arg Thr Ala Ser Glu Lys Glu
225                 230                 235                 240

Pro Arg Leu Val Leu Asn Val Pro Asp Gly Thr Asn Phe Phe Asp Ile
                245                 250                 255

Lys Pro Glu Asp Phe Glu Leu Val Asp Tyr Glu Pro Val Lys Pro Gln
            260                 265                 270

Leu Lys Phe Asp Leu Ala Ile
        275


<210> SEQ ID NO 5
<211> LENGTH: 7094
<212> TYPE: DNA
<213> ORGANISM: Lactococcus lactis
<220> FEATURE:
<221> NAME/KEY: CDS
<222> LOCATION: (4469)..(5305)
<223> OTHER INFORMATION:

<400> SEQUENCE: 5

ggttttccca gtccgacgtt gtaaaacgac ggccagtgaa ttcattaaca gccttttgag      60

cagctagctc attattttga aataaatcat aaatttcttt cccactatct gatttatgat     120

tgctagcata tttgttgtat aatcgaacga gtccattttg aacagatcca tatagattga     180

gtgaactata aaatacatct atatcatagt tgagtttgtt cacaatcatg agaccaaatt     240

ctccagcatt tcgtgtagaa ccacgataaa gctgtttatt tagcaaaatg gcacctccga     300

cacctgtacc taaagtcatg caaataaaat tttggctttc ttgtccattc cctagccaaa     360

gttcagctag acctgcacaa ttggcatcat tttcaacata aaccggaaga tttaaatgtt     420

tttgtagttc tgtccccaat ggatagccat aaagatcagt tagagctcct gccagtaata     480

atgttccctt tttgtcagaa gttccgggaa cacttacacc aattgcagat actgaatgat     540

gagcttttaa ctgatgaata tttgtgagca agctatccat aattttttct ttttttaatg     600

gggttggaac ttgtaaatgt tgtatgatcg ttccatcact agttacaaga ccaaatttta     660

taaatgtacc accgatatca attcctattg aataatgcat cttttattac ctctttctct     720

aatttgtttt agtatagcaa aatcaaaaaa ttaattatgg tatgcattat agatatgttg     780

tataattttc acaaaaacgg agaaaactat gaaaacaata gaacagctca tgatagattc     840

agcagattta atgtcagatt ttattcaatt gacaattttt atattccgca aggaggattt     900

tcaacttttt tataggagtg atgaagaaga gcaagctttt tcaaggtaat gactccaact     960

tattgatagt gttttatgtt cagataatgc ccgatgactt tgtcatgcag ctccaccgat    1020

tttgagaacg acagcgactt ccgtcccagc cgtgccaggt gctgcctcag attcaggtta    1080

tgccgctcaa ttcgctgcgt atatcgcttg ctgattacgt gcagctttcc cttcaggcgg    1140
```

-continued

```
gattcataca gcggccagcc atccgtcatc catatcacca cgtcaaaggg tgacagcagg   1200
ctcataagac gccccagcgt cgccatagtg cgttcaccga atacgtgcgc aacaaccgtc   1260
ttccggagac tgtcatacgc gtaaaacagc cagcgctggc gcgatttagc cccgacatag   1320
ccccactgtt cgtccatttc cgcgcagacg atgacgtcac tgcccggctg tatgcgcgag   1380
gttaccgact gcggcctgag ttttttaagt gacgtaaaat cgtgttgagg ccaacgccca   1440
taatgcgggc tgttgcccgg catccaacgc cattcatggc catatcaatg attttctggt   1500
gcgtaccggg ttgagaagcg gtgtaagtga actgcagttg ccatgtttta cggcagtgag   1560
agcagagata gcgctgatgt ccggcggtgc ttttgccgtt acgcaccacc ccgtcagtag   1620
ctgaacagga gggacagctg atagaaacag aagccactgg agcacctcaa aaacaccatc   1680
atacactaaa tcagtaagtt ggcagcatca cccttttca aaagaaatca tcgctcattt   1740
atctcagttg cccttgaagg aagaggtgaa tttattttat atgcctaaga taaaaggata   1800
tattacttat ttttctgtat ttggtaaaga ggagtatctt ctacttattt ttaaaggaca   1860
agaaaaactt gcaaataatc ctttccccgt tgaagtaaaa caattattaa aaagtggtat   1920
tttactctat caaatgattt ttcaagaaaa attagattat gaagaattat ttgagaaaaa   1980
tcagcatatt atttctccat tgcttgctgc taaaccaatt gaatggaatg attccaatac   2040
gtgaggaaag taaattccca taaaacatat ctttttgaaa aatatttggg ggaatgtgtt   2100
attcgtggag atgttgcaga gttaaaaaaa gctttttcaa attatatgaa taaaggaact   2160
gctggaaaat tatctaataa ttcaatgcga cataagaaaa acattttgat ttcagtcatc   2220
actatgacta ctcgttcggc tatacaggga ggattacctg aagaagaagc tttttttgatg   2280
agtgatttat atattcaaga gcttgaagaa ttaacggaat tagaagaaat tagaacgctt   2340
gcctataatg tgatgatcga ttttgcagat aaagtgaaac agcatcgata ttgtcaggtt   2400
tcttataaaa tattatcttg tcaaaagtat attgttaatc atttatacga aaaactaagt   2460
gtgagtgaaa ttgcagaaga gctacacatg aatatttctt atttatcttc acaattcaaa   2520
aaagagacag ggcaaacaat tacaaacttt attcaggaga agcgaataga agaagctaga   2580
gaattaatcc ttttctcaga ctatcctttt tcaagaattt ataccttgtt ggttttactg   2640
ccaaagtcat tttataaaaa tatttaaaaa atatactgga ataactccca aaaagtttca   2700
agatcagtat atttatcatg cctctacatc aatatatgat tgaaattaaa aaaagaccta   2760
gaatttcaaa attgataaaa tacataccta aaatattaat tctgtactat tacgggtgga   2820
gtatctactg tataatgagg gtataaatta tggaagaagg gagtaaaact aaatttattg   2880
atggttttac gaattaatta ggatattttt tttaaaaacc aaagaaaacg cttacaaacg   2940
ttaaaggagt gaatctaaag atggacaaat ttgaaaaatg gctaaataag accttgatgc   3000
cacttgcctc aaaaatgaat aaaaatcatt tcatttcggc attaagtgaa gcatttatga   3060
gatgtatgcc cttaacatta gggattgcat tattgacaat tataggatac tttccagttc   3120
ctgcctgggt agatttctta aactctattg gactggctca gcatttttca gcagttattg   3180
gtgcagttac cagtgcgcta gcaatttatg taacttataa ttttgcttat tcttatgtaa   3240
atcgtcatga atataatggc catacggccg gtttattatc aatcgcaagt ttgttaatgc   3300
taatgccaca aattattact gtccctgtag taaaaaacat tccaaccgaa tttccgaaat   3360
ccgcggtagt tgacagtgtg tcaaatgttg aagcatttca aacggtatac acgggtagca   3420
caggattaat tgtagcaatc ataattggtt ttattgtttc attagtctat atacaattga   3480
gcaaaagaaa tttagttatt aaattaccag ctggagttcc tccaatggtt gtagattcac   3540
```

-continued

```
taagtccagc aattatttca atggtgattt tctgtttgat gttcgggatt cgtgtgggat   3600

tctcttatac gccattccat gatattttca atttctcaac acaactaatt caagcaccgt   3660

tgactggtgc tgtggcaaat ccatgggttc ttatgggcat ctttaccttt ggtaatttct   3720

tatggttctt tggtatccac cctaatttaa ttgggggaat tttaaatcca ttgttattaa   3780

caatgtcata tgctaatatt gatgcctatg ctgccggaaa acctgtacca tacttacaaa   3840

tgatgattgt gtttgctgtg ggtgcgaacg catggggcgg aagtggaaat acttatgggt   3900

tagttatttc aatgtttacg gcaaaatctg aacgctataa acaattatta aaattaggtg   3960

caattcctag tattttcaat atcagtgaac cattactttt tggtcttcca atgatgttaa   4020

atcctctttt ctttattcct ttggttttcc aaccagcaat tttaggaact gtagcattgg   4080

gcttggcaaa gatattatat attacaaatc tgaatccaat gacggcactt cttccttgga   4140

cgacaccagc acctgtgaga atggccattt caggtggact tccatttttg attatttttg   4200

caatctgttt agtcttgaat gttcttattt actacccatt ctttaaggtg gcgtataata   4260

aagctttaga agaagaaaaa gcagctgttg aattagaggg ttcagaaact gcctgatgga   4320

tatttttat aaatctggtt tgaacaaatt atattgacat ctctttttct atcctgataa   4380

ttctgagagg ttattttggg aaatactatt gaaccatatc gaggtggtgt ggtataatga   4440

agggaattaa aaaagatagg aaaatttc atg act tac gca gat caa gtt ttt      4492
                                Met Thr Tyr Ala Asp Gln Val Phe
                                1               5

aaa caa aat atc caa aat atc cta gat aat ggt gtt ttt tca gaa aat      4540
Lys Gln Asn Ile Gln Asn Ile Leu Asp Asn Gly Val Phe Ser Glu Asn
    10                  15                  20

gca aga cca aag tat aag gat ggt caa atg gcg aat agc aaa tat gtc      4588
Ala Arg Pro Lys Tyr Lys Asp Gly Gln Met Ala Asn Ser Lys Tyr Val
25                  30                  35                  40

act ggt tca ttc gtt act tat gat ttg caa aag ggg gag ttt cca att      4636
Thr Gly Ser Phe Val Thr Tyr Asp Leu Gln Lys Gly Glu Phe Pro Ile
                45                  50                  55

acc act ttg cgt cca att cca atc aaa tct gct att aaa gaa ttg atg      4684
Thr Thr Leu Arg Pro Ile Pro Ile Lys Ser Ala Ile Lys Glu Leu Met
            60                  65                  70

tgg ata tac caa gac caa aca agt gaa ctt tct gtt ctc gaa gag aag      4732
Trp Ile Tyr Gln Asp Gln Thr Ser Glu Leu Ser Val Leu Glu Glu Lys
        75                  80                  85

tat gga gtc aaa tac tgg gga gaa tgg gga att ggt gat ggt acg att      4780
Tyr Gly Val Lys Tyr Trp Gly Glu Trp Gly Ile Gly Asp Gly Thr Ile
    90                  95                  100

ggg caa cgt tat ggt gca aca gtc aaa aaa tat aat atc att ggt aaa      4828
Gly Gln Arg Tyr Gly Ala Thr Val Lys Lys Tyr Asn Ile Ile Gly Lys
105                 110                 115                 120

tta tta gaa ggc ttg gcc aaa aat cca tgg aat cgt cgt aat atc atc      4876
Leu Leu Glu Gly Leu Ala Lys Asn Pro Trp Asn Arg Arg Asn Ile Ile
                125                 130                 135

aac ctt tgg cag tat gaa gat ttt gag gaa aca gaa ggt ctt tta cca      4924
Asn Leu Trp Gln Tyr Glu Asp Phe Glu Glu Thr Glu Gly Leu Leu Pro
            140                 145                 150

tgt gct ttc caa acg atg ttt gat gtc cgt cga gaa aaa gat ggt cag      4972
Cys Ala Phe Gln Thr Met Phe Asp Val Arg Arg Glu Lys Asp Gly Gln
        155                 160                 165

att tat ttg gat gcc aca ctg att caa cgt tca aac gat atg ctt gta      5020
Ile Tyr Leu Asp Ala Thr Leu Ile Gln Arg Ser Asn Asp Met Leu Val
    170                 175                 180
```

-continued

```
gcc cac cat atc aat gcg atg caa tat gtt gct ttg caa atg atg att     5068
Ala His His Ile Asn Ala Met Gln Tyr Val Ala Leu Gln Met Met Ile
185                 190                 195                 200

gca aaa cat ttt tct tgg aaa gtt ggg aaa ttc ttt tat ttt gta aat     5116
Ala Lys His Phe Ser Trp Lys Val Gly Lys Phe Phe Tyr Phe Val Asn
                205                 210                 215

aat tta cat att tat gat aat cag ttt gag cag gca aat gaa tta atg     5164
Asn Leu His Ile Tyr Asp Asn Gln Phe Glu Gln Ala Asn Glu Leu Met
            220                 225                 230

aag cga aca gct tct gaa aaa gaa cct cgt ttg gtc ctt aat gtt cct     5212
Lys Arg Thr Ala Ser Glu Lys Glu Pro Arg Leu Val Leu Asn Val Pro
        235                 240                 245

gat ggt aca aac ttt ttc gat att aaa cct gaa gat ttt gaa ctt gtg     5260
Asp Gly Thr Asn Phe Phe Asp Ile Lys Pro Glu Asp Phe Glu Leu Val
    250                 255                 260

gac tat gag cca gta aaa cct caa ttg aaa ttt gat tta gca att         5305
Asp Tyr Glu Pro Val Lys Pro Gln Leu Lys Phe Asp Leu Ala Ile
265                 270                 275

taaattaatc tataagttac tgacaaaact gtcagtaact tttttgtgg gaaaaatgta   5365

tttttatgac cgtaaagaat ctgtcagtag aagtctgaaa ttcgtttaaa aatcgactag  5425

aataggcttt aacgacaaga tgttttaaag agtacgctct aaatgtattt ttgtattttt  5485

gtttgattac gaagtttaaa tttaattgac aaatgtttta aaatgagtat aataggactt  5545

gtaaccgatt ttatttttat aaaggagaaa gaaagatgaa caaactttta cttggaacag  5605

cctttatagg ggctagctta ctgattggtg ggggtgctca tgcagatcaa atgtttatcg  5665

tttgtataat cataatactg gtgagcactc tatacaacta gtgggacacc aaaagaatgc  5725

taatgtaagt gcgggttgga cttatgaagg tgtcggttgg atcgcaccaa caacaagttc  5785

aagcccagtt taccgtgtgt acaatccaaa tgcattatta cacaaaaagc aagtatgaag  5845

cccaaagttt agtaaataag ggttggaaat gggataataa cggaaaggcg gtcttctatt  5905

ctggaggttc tcaagccgta tatgtcgctt ataatcccaa tgcacaatct ggcgctcaca  5965

attacacgga aagtagcttt gagcaaaata gcttattgaa tactggttgg aaatatgggg  6025

cagtagcttg gtacgggatt ggagtaaaaa acgaaatgtt aaacattgct caaattgtta  6085

gtggtaattt ttctagtatt gttggaactt ggaaagatac ttctggaaat atgcttgaaa  6145

ttaatgcaat gggaaatctt actttaatat ggaaaggggc aaagaatcaa acctttgaac  6205

ttggcgcagg tcaacaattt aatggaactg cagatattgc cttaaaaaat ggagagattt  6265

cccctggtag tccacttaac atttttgttg taccaacaga agttgctttc cctaataata  6325

aaaaagtaga cgattcaact gggcaacaac gaatttttgt gaattattct ggtacaagcc  6385

ctcaaatggc gaatagtatg gcagcggtgg ctttttttag agttattcca tgattatatt  6445

aaagttagaa ttgaataaaa tgtattatta aaaagataat attatatcac gacaaggcga  6505

catctatcaa ctttaccact ggtatggaag tgaccattat tacatcagga aacgctaaaa  6565

cggttgtttt tacacccgta aaataaataa taaaataatg tgaaattact gacagcattt  6625

tgtcagtaat ttttttatc aaaatcacac aaaaatgttc gttgacgaac aaaaaaaact   6685

atgttataat aattcgtatg cgaactaaaa aagaagcgat tggccgactt ttaaaagtag  6745

ccagcaacca aatgtctcga gaatttgata attttgcagc tcaacttgat ttgacaggtc  6805

agcaaatgtc aattttagat tttcttggaa atcaaagcga agaaggttca ggaaaagaaa  6865

ttagtcagac gatgattgaa ttagaattta atatccgacg ttcaacaacg acggaaattt  6925

tacagcgcat ggaaaagcgg cttttaatta atcgaagaac aagcctgacc gatgcccgcc  6985
```

-continued

```
aaaaatcagt tgaattaact gaagaaggga aaagatattt acctgaaatc agggcttata   7045

tccaagcaca taataaaaaa gcttggcgta atcatggtca tagctgttt               7094


<210> SEQ ID NO 6
<211> LENGTH: 279
<212> TYPE: PRT
<213> ORGANISM: Lactococcus lactis

<400> SEQUENCE: 6

Met Thr Tyr Ala Asp Gln Val Phe Lys Gln Asn Ile Gln Asn Ile Leu
1               5                   10                  15

Asp Asn Gly Val Phe Ser Glu Asn Ala Arg Pro Lys Tyr Lys Asp Gly
            20                  25                  30

Gln Met Ala Asn Ser Lys Tyr Val Thr Gly Ser Phe Val Thr Tyr Asp
        35                  40                  45

Leu Gln Lys Gly Glu Phe Pro Ile Thr Thr Leu Arg Pro Ile Pro Ile
    50                  55                  60

Lys Ser Ala Ile Lys Glu Leu Met Trp Ile Tyr Gln Asp Gln Thr Ser
65                  70                  75                  80

Glu Leu Ser Val Leu Glu Glu Lys Tyr Gly Val Lys Tyr Trp Gly Glu
                85                  90                  95

Trp Gly Ile Gly Asp Gly Thr Ile Gly Gln Arg Tyr Gly Ala Thr Val
            100                 105                 110

Lys Lys Tyr Asn Ile Ile Gly Lys Leu Leu Glu Gly Leu Ala Lys Asn
        115                 120                 125

Pro Trp Asn Arg Arg Asn Ile Ile Asn Leu Trp Gln Tyr Glu Asp Phe
    130                 135                 140

Glu Glu Thr Glu Gly Leu Leu Pro Cys Ala Phe Gln Thr Met Phe Asp
145                 150                 155                 160

Val Arg Arg Glu Lys Asp Gly Gln Ile Tyr Leu Asp Ala Thr Leu Ile
                165                 170                 175

Gln Arg Ser Asn Asp Met Leu Val Ala His His Ile Asn Ala Met Gln
            180                 185                 190

Tyr Val Ala Leu Gln Met Met Ile Ala Lys His Phe Ser Trp Lys Val
        195                 200                 205

Gly Lys Phe Phe Tyr Phe Val Asn Asn Leu His Ile Tyr Asp Asn Gln
    210                 215                 220

Phe Glu Gln Ala Asn Glu Leu Met Lys Arg Thr Ala Ser Glu Lys Glu
225                 230                 235                 240

Pro Arg Leu Val Leu Asn Val Pro Asp Gly Thr Asn Phe Phe Asp Ile
                245                 250                 255

Lys Pro Glu Asp Phe Glu Leu Val Asp Tyr Glu Pro Val Lys Pro Gln
            260                 265                 270

Leu Lys Phe Asp Leu Ala Ile
        275


<210> SEQ ID NO 7
<211> LENGTH: 1000
<212> TYPE: DNA
<213> ORGANISM: Lactococcus lactis

<400> SEQUENCE: 7

atatacaatt gagcaaaaga aatttagtta ttaaattacc agctggagtt cctccaatgg     60

ttgtagattc actaagtcca gcaattattt caatggtgat tttctgtttg atgttcggga    120

ttcgtgtggg attctcttat acgccattcc atgatatttt caatttctca acacaactaa    180
```

-continued

```
ttcaagcacc gttgactggt gctgtggcaa atccatgggt tcttatgggc atctttacct    240

ttggtaattt cttatggttc tttggtatcc accctaattt aattggggga attttaaatc    300

cattgttatt aacaatgtca tatgctaata ttgatgccta tgctgccgga aaacctgtac    360

catacttaca aatgatgatt gtgtttgctg tgggtgcgaa cgcatggggc ggaagtggaa    420

atacttatgg gttagttatt tcaatgttta cggcaaaatc tgaacgctat aaacaattat    480

taaaattagg tgcaattcct agtattttca atatcagtga accattactt tttggtcttc    540

caatgatgtt aaatcctctt ttctttattc ctttggtttt ccaaccagca attttaggaa    600

ctgtagcatt gggcttggca aagatattat atattacaaa tctgaatcca atgacggcac    660

ttcttccttg gacgacacca gcacctgtga gaatggccat ttcaggtgga cttccatttt    720

tgattatttt tgcaatctgt ttagtcttga atgttcttat ttactaccca ttctttaagg    780

tggcgtataa taaagcttta gaagaagaaa aagcagctgt tgaattagag ggttcagaaa    840

ctgcctgatg gatatttttt ataaatctgg tttgaacaaa ttatattgac atctcttttt    900

ctatcctgat aattctgaga ggttattttg ggaaatacta ttgaaccata tcgaggtggt    960

gtggtataat gaagggaatt aaaaaagata ggaaaatttc                          1000


<210> SEQ ID NO 8
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 8

atgacttacg cagatcaagt tttt                                              24


<210> SEQ ID NO 9
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 9

ttaaattgct aaatcaaatt tcaattg                                           27


<210> SEQ ID NO 10
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 10

tctgattgag taccttgacc                                                   20


<210> SEQ ID NO 11
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 11

gcaatcataa ttggttttat tg                                                22
```

-continued

<210> SEQ ID NO 12
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 12
cttacatgac tatgaaaatc cg 22

<210> SEQ ID NO 13
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 13 ctttttatt attagggaaa gca 23

<210> SEQ ID NO 14
<211> LENGTH: 21
<212> TYPE: DNA
<213> ORGANISM: Artificial Sequence
<220> FEATURE:
<223> OTHER INFORMATION: expression unit comprising the lactococcal P1 promoter, the E.col i bacteriophage T7 expression signals, putative RNA stabilising sequence and modified gene10 ribosomal binding site

<400> SEQUENCE: 14
gattaagtca tcttacctct t 21

<210> SEQ ID NO 15
<211> LENGTH: 39
<212> TYPE: DNA
<213> ORGANISM: Artificial Sequence
<220> FEATURE:
<223> OTHER INFORMATION: thyA-, P1-T7-usp45-hIL10

<400> SEQUENCE: 15
agataggaaa atttcatgga ttaagtcatc ttacctctt 39

<210> SEQ ID NO 16
<211> LENGTH: 36
<212> TYPE: DNA
<213> ORGANISM: Artificial Sequence
<220> FEATURE:
<223> OTHER INFORMATION: ATG not included, thyA-, P1-T7-usp45-hIL10

<400> SEQUENCE: 16
agataggaaa atttcgatta agtcatctta cctctt 36

<210> SEQ ID NO 17
<211> LENGTH: 48
<212> TYPE: DNA
<213> ORGANISM: Artificial Sequence
<220> FEATURE:
<223> OTHER INFORMATION: thyA promoter not included, theA-, P1-T7-usp45-hIL10

<400> SEQUENCE: 17
tctgagaggt tattttggga aatactagat taagtcatct tacctctt 48

-continued

<210> SEQ ID NO 18
<211> LENGTH: 40
<212> TYPE: DNA
<213> ORGANISM: Artificial Sequence
<220> FEATURE:
<223> OTHER INFORMATION: thyA-, usp45-hIL10

<400> SEQUENCE: 18
aaaatccgta actaactaga attaatctat aagttactga 40

<210> SEQ ID NO 19
<211> LENGTH: 6967
<212> TYPE: DNA
<213> ORGANISM: Lactococcus lactis
<220> FEATURE:
<221> NAME/KEY: misc_feature
<223> OTHER INFORMATION: Thy11

<400> SEQUENCE: 19
attaacagcc ttttgagcag ctagctcatt attttgaaat aaatcataaa tttctttccc 60
actatctgat ttatgattgc tagcatattt gttgtataat cgaacgagtc cattttgaac 120
agatccatat agattgagtg aactataaaa tacatctata tcatagttga gtttgttcac 180
aatcatgaga ccaaattctc cagcatttcg tgtagaacca cgataaagct gtttatttag 240
caaaatggca cctccgacac ctgtacctaa agtcatgcaa ataaaatttt ggctttcttg 300
tccattccct agccaaagtt cagctagacc tgcacaattg gcatcatttt caacataaac 360
cggaagattt aaatgttttt gtagttctgt ccccaatgga tagccataaa gatcagttag 420
agctcctgcc agtaataatg ttcccttttt gtcagaagtt ccgggaacac ttacaccaat 480
tgcagatact gaatgatgag cttttaactg atgaatattt gtgagcaagc tatccataat 540
tttttctttt tttaatgggg ttggaacttg taaatgttgt atgatcgttc catcactagt 600
tacaagacca aattttataa atgtaccacc gatatcaatt cctattgaat aatgcatctt 660
ttattacctc tttctctaat ttgttttagt atagcaaaat caaaaaatta attatggtat 720
gcattataga tatgttgtat aattttcaca aaaacggaga aaactatgaa aacaatagaa 780
cagctcatga tagattcagc agatttaatg tcagatttta ttcaattgac aatttttata 840
ttccgcaagg aggattttca actttttat aggagtgatg aagaagagca agcttttca 900 aggtaatgac tccaacttat tgatagtgtt ttatgttcag ataatgcccg atgactttgt 960
catgcagctc caccgatttt gagaacgaca gcgacttccg tcccagccgt gccaggtgct 1020
gcctcagatt caggttatgc cgctcaattc gctgcgtata tcgcttgctg attacgtgca 1080
gctttccctt caggcgggat tcatacagcg gccagccatc cgtcatccat atcaccacgt 1140
caaagggtga cagcaggctc ataagacgcc ccagcgtcgc catagtgcgt tcaccgaata 1200
cgtgcgcaac aaccgtcttc cggagactgt catacgcgta aaacagccag cgctggcgcg 1260
atttagcccc gacatagccc cactgttcgt ccatttccgc gcagacgatg acgtcactgc 1320
ccggctgtat gcgcgaggtt accgactgcg gcctgagttt tttaagtgac gtaaaatcgt 1380
gttgaggcca acgcccataa tgcgggctgt tgcccggcat ccaacgccat tcatggccat 1440
atcaatgatt ttctggtgcg taccgggttg agaagcggtg taagtgaact gcagttgcca 1500
tgttttacgg cagtgagagc agagatagcg ctgatgtccg gcggtgcttt tgccgttacg 1560
caccaccccg tcagtagctg aacaggaggg acagctgata gaaacagaag ccactggagc 1620
acctcaaaaa caccatcata cactaaatca gtaagttggc agcatcaccc tttttcaaaa 1680
gaaatcatcg ctcatttatc tcagttgccc ttgaaggaag aggtgaattt attttatatg 1740

-continued

```
cctaagataa aaggatatat tacttatttt tctgtatttg gtaaagagga gtatcttcta   1800
cttattttta aaggacaaga aaaacttgca aataatcctt tccccgttga agtaaaacaa   1860
ttattaaaaa gtggtatttt actctatcaa atgatttttc aagaaaaatt agattatgaa   1920
gaattatttg agaaaaatca gcatattatt tctccattgc ttgctgctaa accaattgaa   1980
tggaatgatt ccaatacgtg aggaaagtaa attcccataa aacatatctt tttgaaaaat   2040
atttggggga atgtgttatt cgtggagatg ttgcagagtt aaaaaaagct ttttcaaatt   2100
atatgaataa aggaactgct ggaaaattat ctaataattc aatgcgacat aagaaaaaca   2160
ttttgatttc agtcatcact atgactactc gttcggctat acagggagga ttacctgaag   2220
aagaagcttt tttgatgagt gatttatata ttcaagagct tgaagaatta acggaattag   2280
aagaaattag aacgcttgcc tataatgtga tgatcgattt tgcagataaa gtgaaacagc   2340
atcgatattg tcaggtttct tataaaatat tatcttgtca aaagtatatt gttaatcatt   2400
tatacgaaaa actaagtgtg agtgaaattg cagaagagct acacatgaat atttcttatt   2460
tatcttcaca attcaaaaaa gagacagggc aaacaattac aaactttatt caggagaagc   2520
gaatagaaga agctagagaa ttaatccttt tctcagacta tccttttttca agaatttata   2580
ccttgttggt tttactgcca aagtcatttt ataaaaatat ttaaaaaata tactggaata   2640
actcccaaaa agtttcaaga tcagtatatt tatcatgcct ctacatcaat atatgattga   2700
aattaaaaaa agacctagaa tttcaaaatt gataaaatac atacctaaaa tattaattct   2760
gtactattac gggtggagta tctactgtat aatgagggta taaattatgg aagaagggag   2820
taaaactaaa tttattgatg gttttacgaa ttaattagga tatttttttt aaaaaccaaa   2880
gaaaacgctt acaaacgtta aaggagtgaa tctaaagatg gacaaatttg aaaaatggct   2940
aaataagacc ttgatgccac ttgcctcaaa aatgaataaa aatcatttca tttcggcatt   3000
aagtgaagca tttatgagat gtatgccctt aacattaggg attgcattat tgacaattat   3060
aggatacttt ccagttcctg cctgggtaga tttcttaaac tctattggac tggctcagca   3120
tttttcagca gttattggtg cagttaccag tgcgctagca atttatgtaa cttataattt   3180
tgcttattct tatgtaaatc gtcatgaata taatggccat acggccggtt tattatcaat   3240
cgcaagtttg ttaatgctaa tgccacaaat tattactgtc cctgtagtaa aaaacattcc   3300
aaccgaattt ccgaaatccg cggtagttga cagtgtgtca aatgttgaag catttcaaac   3360
ggtatacacg ggtagcacag gattaattgt agcaatcata attggtttta ttgtttcatt   3420
agtctatata caattgagca aaagaaattt agttattaaa ttaccagctg gagttcctcc   3480
aatggttgta gattcactaa gtccagcaat tatttcaatg gtgattttct gtttgatgtt   3540
cgggattcgt gtgggattct cttatacgcc attccatgat attttcaatt tctcaacaca   3600
actaattcaa gcaccgttga ctggtgctgt ggcaaatcca tgggttctta tgggcatctt   3660
tacctttggt aatttcttat ggttctttgg tatccaccct aatttaattg gggaatttt   3720
aaatccattg ttattaacaa tgtcatatgc taatattgat gcctatgctg ccggaaaacc   3780
tgtaccatac ttacaaatga tgattgtgtt tgctgtgggt gcgaacgcat ggggcggaag   3840
tggaaatact tatgggttag ttatttcaat gtttacggca aaatctgaac gctataaaca   3900
attattaaaa ttaggtgcaa ttcctagtat tttcaatatc agtgaaccat tactttttgg   3960
tcttccaatg atgttaaatc ctcttttctt tattcctttg gttttccaac cagcaatttt   4020
aggaactgta gcattgggct tggcaaagat attatatatt acaaatctga atccaatgac   4080
ggcacttctt ccttggacga caccagcacc tgtgagaatg gccatttcag gtggacttcc   4140
```

-continued

```
attttttgatt atttttgcaa tctgtttagt cttgaatgtt cttatttact acccattctt   4200
taaggtggcg tataataaag ctttagaaga agaaaaagca gctgttgaat tagagggttc   4260
agaaactgcc tgatggatat tttttataaa tctggtttga acaaattata ttgacatctc   4320
tttttctatc ctgataattc tgagaggtta ttttgggaaa tactattgaa ccatatcgag   4380
gtggtgtggt ataatgaagg gaattaaaaa agataggaaa atttcatgga ttaagtcatc   4440
ttacctcttt tattagtttt ttcttataat ctaatgataa catttttata attaatctat   4500
aaaccatatc cctctttgga atcaaaattt attatctact cctttgtaga tatgttataa   4560
tacaagtatc agatctggga gaccacaacg gtttcccact agaaataatt ttgtttaact   4620
ttagaaagga gatatacgca tgaaaaaaaa gattatctca gctattttaa tgtctacagt   4680
catactttct gctgcagccc cgttgtcagg tgtttacgcc tcagctggtc aaggtactca   4740
atcagaaaac tcatgtactc actttccagg taacttgcca aacatgcttc gtgatttgcg   4800
tgatgctttt tcacgtgtta aaactttttt tcaaatgaaa gatcaacttg ataacttgct   4860
tttgaaagaa tcacttttgg aagattttaa aggttacctt ggttgtcaag ctttgtcaga   4920
aatgatccaa ttttaccttg aagaagttat gccacaagct gaaaaccaag atccagatat   4980
caaagctcac gttaactcat tgggtgaaaa ccttaaaact ttgcgtcttc gtttgcgtcg   5040
ttgtcaccgt tttcttccat gtgaaaacaa atcaaaagct gttgaacaag ttaaaaacgc   5100
ttttaacaaa ttgcaagaaa aaggtatcta caaagctatg tcagaatttg atatctttat   5160
caactacatc gaagcttaca tgactatgaa aatccgtaac taactagaat taatctataa   5220
gttactgaca aaactgtcag taactttttt tgtgggaaaa atgtattttt atgaccgtaa   5280
agaatctgtc agtagaagtc tgaaattcgt ttaaaaatcg actagaatag gctttaacga   5340
caagatgttt taaagagtac gctctaaatg tatttttgta tttttgtttg attacgaagt   5400
ttaaatttaa ttgacaaatg ttttaaaatg agtataatag gacttgtaac cgattttatt   5460
tttataaagg agaaagaaag atgaacaaac ttttacttgg aacagccttt ataggggcta   5520
gcttactgat tggtgggggt gctcatgcag atcaaatgtt tatcgtttgt ataatcataa   5580
tactggtgag cactctatac aactagtggg acaccaaaag aatgctaatg taagtgcggg   5640
ttggacttat gaaggtgtcg gttggatcgc accaacaaca agttcaagcc cagtttaccg   5700
tgtgtacaat ccaaatgcat tattacacaa aaagcaagta tgaagcccaa agtttagtaa   5760
ataagggttg gaaatgggat aataacggaa aggcggtctt ctattctgga ggttctcaag   5820
ccgtatatgt cgcttataat cccaatgcac aatctggcgc tcacaattac acggaaagta   5880
gctttgagca aaatagctta ttgaatactg gttggaaata tggggcagta gcttggtacg   5940
ggattggagt aaaaaacgaa atgttaaaca ttgctcaaat tgttagtggt aatttttcta   6000
gtattgttgg aacttggaaa gatacttctg gaaatatgct tgaaattaat gcaatgggaa   6060
atcttacttt aatatggaaa ggggcaaaga atcaaacctt tgaacttggc gcaggtcaac   6120
aatttaatgg aactgcagat attgccttaa aaaatggaga gatttcccct ggtagtccac   6180
ttaacatttt tgttgtacca acagaagttg ctttccctaa taataaaaaa gtagacgatt   6240
caactgggca acaacgaatt tttgtgaatt attctggtac aagccctcaa atggcgaata   6300
gtatggcagc ggtggctttt tttagagtta ttccatgatt atattaaagt tagaattgaa   6360
taaaatgtat tattaaaaag ataatattat atcacgacaa ggcgacatct atcaacttta   6420
ccactggtat ggaagtgacc attattacat caggaaacgc taaaacggtt gtttttacac   6480
ccgtaaaata aataataaaa taatgtgaaa ttactgacag cattttgtca gtaatttttt   6540
```

-continued

```
ttatcaaaat cacacaaaaa tgttcgttga cgaacaaaaa aaactatgtt ataataattc   6600

gtatgcgaac taaaaaagaa gcgattggcc gacttttaaa agtagccagc aaccaaatgt   6660

ctcgagaatt tgataatttt gcagctcaac ttgatttgac aggtcagcaa atgtcaattt   6720

tagattttct tggaaatcaa agcgaagaag gttcaggaaa agaaattagt cagacgatga   6780

ttgaattaga atttaatatc cgacgttcaa caacgacgga aattttacag cgcatggaaa   6840

agcggctttt aattaatcga agaacaagcc tgaccgatgc ccgccaaaaa tcagttgaat   6900

taactgaaga agggaaaaga tatttacctg aaatcagggc ttatatccaa gcacataata   6960

aaaaagc                                                             6967
```

<210> SEQ ID NO 20
<211> LENGTH: 6753
<212> TYPE: DNA
<213> ORGANISM: Lactococcus lactis
<220> FEATURE:
<221> NAME/KEY: misc_feature
<223> OTHER INFORMATION: Thy12

<400> SEQUENCE: 20

```
attaacagcc ttttgagcag ctagctcatt attttgaaat aaatcataaa tttctttccc     60

actatctgat ttatgattgc tagcatattt gttgtataat cgaacgagtc cattttgaac    120

agatccatat agattgagtg aactataaaa tacatctata tcatagttga gtttgttcac    180

aatcatgaga ccaaattctc cagcatttcg tgtagaacca cgataaagct gtttatttag    240

caaaatggca cctccgacac ctgtacctaa agtcatgcaa ataaaatttt ggctttcttg    300

tccattccct agccaaagtt cagctagacc tgcacaattg gcatcatttt caacataaac    360

cggaagattt aaatgttttt gtagttctgt ccccaatgga tagccataaa gatcagttag    420

agctcctgcc agtaataatg ttcccttttt gtcagaagtt ccgggaacac ttacaccaat    480

tgcagatact gaatgatgag cttttaactg atgaatattt gtgagcaagc tatccataat    540

tttttctttt tttaatgggg ttggaacttg taaatgttgt atgatcgttc catcactagt    600

tacaagacca aattttataa atgtaccacc gatatcaatt cctattgaat aatgcatctt    660

ttattacctc tttctctaat ttgttttagt atagcaaaat caaaaaaatta attatggtat    720

gcattataga tatgttgtat aattttcaca aaaacggaga aaactatgaa aacaatagaa    780

cagctcatga tagattcagc agatttaatg tcagatttta ttcaattgac aatttttata    840

ttccgcaagg aggattttca actttttat aggagtgatg aagaagagca agctttttca     900

aggtaatgac tccaacttat tgatagtgtt ttatgttcag ataatgcccg atgactttgt    960

catgcagctc caccgatttt gagaacgaca gcgacttccg tcccagccgt gccaggtgct   1020

gcctcagatt caggttatgc cgctcaattc gctgcgtata tcgcttgctg attacgtgca   1080

gctttccctt caggcgggat tcatacagcg gccagccatc cgtcatccat atcaccacgt   1140

caaagggtga cagcaggctc ataagacgcc ccagcgtcgc catagtgcgt tcaccgaata   1200

cgtgcgcaac aaccgtcttc cggagactgt catacgcgta aaacagccag cgctggcgcg   1260

atttagcccc gacatagccc cactgttcgt ccatttccgc gcagacgatg acgtcactgc   1320

ccggctgtat gcgcgaggtt accgactgcg gcctgagttt tttaagtgac gtaaaatcgt   1380

gttgaggcca acgcccataa tgcgggctgt tgcccggcat ccaacgccat tcatggccat   1440

atcaatgatt ttctggtgcg taccgggttg agaagcggtg taagtgaact gcagttgcca   1500

tgttttacgg cagtgagagc agagatagcg ctgatgtccg gcggtgcttt tgccgttacg   1560
```

-continued

```
caccaccccg tcagtagctg aacaggaggg acagctgata gaaacagaag ccactggagc   1620
acctcaaaaa caccatcata cactaaatca gtaagttggc agcatcaccc tttttcaaaa   1680
gaaatcatcg ctcatttatc tcagttgccc ttgaaggaag aggtgaattt attttatatg   1740
cctaagataa aaggatatat tacttatttt tctgtatttg gtaaagagga gtatcttcta   1800
cttattttta aaggacaaga aaaacttgca aataatcctt tccccgttga agtaaaacaa   1860
ttattaaaaa gtggtatttt actctatcaa atgatttttc aagaaaaatt agattatgaa   1920
gaattatttg agaaaaatca gcatattatt tctccattgc ttgctgctaa accaattgaa   1980
tggaatgatt ccaatacgtg aggaaagtaa attcccataa aacatatctt tttgaaaaat   2040
atttggggga atgtgttatt cgtggagatg ttgcagagtt aaaaaaagct ttttcaaatt   2100
atatgaataa aggaactgct ggaaaattat ctaataattc aatgcgacat aagaaaaaca   2160
ttttgatttc agtcatcact atgactactc gttcggctat acagggagga ttacctgaag   2220
aagaagcttt tttgatgagt gatttatata ttcaagagct tgaagaatta acggaattag   2280
aagaaattag aacgcttgcc tataatgtga tgatcgattt tgcagataaa gtgaaacagc   2340
atcgatattg tcaggtttct tataaaatat tatcttgtca aaagtatatt gttaatcatt   2400
tatacgaaaa actaagtgtg agtgaaattg cagaagagct acacatgaat atttcttatt   2460
tatcttcaca attcaaaaaa gagacagggc aaacaattac aaactttatt caggagaagc   2520
gaatagaaga agctagagaa ttaatccttt tctcagacta tccttttttca agaatttata   2580
ccttgttggt tttactgcca aagtcatttt ataaaaatat ttaaaaaata tactggaata   2640
actcccaaaa agtttcaaga tcagtatatt tatcatgcct ctacatcaat atatgattga   2700
aattaaaaaa agacctagaa tttcaaaatt gataaaatac atacctaaaa tattaattct   2760
gtactattac gggtggagta tctactgtat aatgagggta taaattatgg aagaagggag   2820
taaaactaaa tttattgatg gttttacgaa ttaattagga tattttttttt aaaaaccaaa   2880
gaaaacgctt acaaacgtta aaggagtgaa tctaaagatg gacaaatttg aaaaatggct   2940
aaataagacc ttgatgccac ttgcctcaaa aatgaataaa aatcatttca tttcggcatt   3000
aagtgaagca tttatgagat gtatgccctt aacattaggg attgcattat tgacaattat   3060
aggatacttt ccagttcctg cctgggtaga tttcttaaac tctattggac tggctcagca   3120
tttttcagca gttattggtg cagttaccag tgcgctagca atttatgtaa cttataattt   3180
tgcttattct tatgtaaatc gtcatgaata taatggccat acggccggtt tattatcaat   3240
cgcaagtttg ttaatgctaa tgccacaaat tattactgtc cctgtagtaa aaaacattcc   3300
aaccgaattt ccgaaatccg cggtagttga cagtgtgtca aatgttgaag catttcaaac   3360
ggtatacacg ggtagcacag gattaattgt agcaatcata attggtttta ttgtttcatt   3420
agtctatata caattgagca aaagaaattt agttattaaa ttaccagctg gagttcctcc   3480
aatggttgta gattcactaa gtccagcaat tatttcaatg gtgattttct gtttgatgtt   3540
cgggattcgt gtgggattct cttatacgcc attccatgat attttcaatt tctcaacaca   3600
actaattcaa gcaccgttga ctggtgctgt ggcaaatcca tgggttctta tgggcatctt   3660
tacctttggt aatttcttat ggttctttgg tatccaccct aatttaattg ggggaatttt   3720
aaatccattg ttattaacaa tgtcatatgc taatattgat gcctatgctg ccggaaaacc   3780
tgtaccatac ttacaaatga tgattgtgtt tgctgtgggt gcgaacgcat ggggcggaag   3840
tggaaatact tatgggttag ttatttcaat gtttacggca aaatctgaac gctataaaca   3900
attattaaaa ttaggtgcaa ttcctagtat tttcaatatc agtgaaccat tacttttttgg   3960
```

-continued

```
tcttccaatg atgttaaatc ctcttttctt tattcctttg gttttccaac cagcaatttt   4020
aggaactgta gcattgggct tggcaaagat attatatatt acaaatctga atccaatgac   4080
ggcacttctt ccttggacga caccagcacc tgtgagaatg gccatttcag gtggacttcc   4140
atttttgatt atttttgcaa tctgtttagt cttgaatgtt cttatttact acccattctt   4200
taaggtggcg tataataaag ctttagaaga agaaaaagca gctgttgaat tagagggttc   4260
agaaactgcc tgatggatat tttttataaa tctggtttga acaaattata ttgacatctc   4320
tttttctatc ctgataattc tgagaggtta ttttgggaaa tactattgaa ccatatcgag   4380
gtggtgtggt ataatgaagg gaattaaaaa agataggaaa atttcatgaa aaaaaagatt   4440
atctcagcta ttttaatgtc tacagtcata ctttctgctg cagccccgtt gtcaggtgtt   4500
tacgcctcag ctggtcaagg tactcaatca gaaaactcat gtactcactt tccaggtaac   4560
ttgccaaaca tgcttcgtga tttgcgtgat gctttttcac gtgttaaaac tttttttcaa   4620
atgaaagatc aacttgataa cttgcttttg aaagaatcac ttttggaaga ttttaaaggt   4680
taccttggtt gtcaagcttt gtcagaaatg atccaatttt accttgaaga agttatgcca   4740
caagctgaaa accaagatcc agatatcaaa gctcacgtta actcattggg tgaaaacctt   4800
aaaactttgc gtcttcgttt gcgtcgttgt caccgttttc ttccatgtga aaacaaatca   4860
aaagctgttg aacaagttaa aaacgctttt aacaaattgc aagaaaaagg tatctacaaa   4920
gctatgtcag aatttgatat ctttatcaac tacatcgaag cttacatgac tatgaaaatc   4980
cgtaactaac tagaattaat ctataagtta ctgacaaaac tgtcagtaac ttttttttgtg   5040
ggaaaaatgt atttttatga ccgtaaagaa tctgtcagta gaagtctgaa attcgtttaa   5100
aaatcgacta gaataggctt taacgacaag atgttttaaa gagtacgctc taaatgtatt   5160
tttgtatttt tgtttgatta cgaagtttaa atttaattga caaatgtttt aaaatgagta   5220
taataggact tgtaaccgat tttatttta taaaggagaa agaaagatga acaaactttt   5280
acttggaaca gcctttatag gggctagctt actgattggt gggggtgctc atgcagatca   5340
aatgtttatc gtttgtataa tcataatact ggtgagcact ctatacaact agtgggacac   5400
caaaagaatg ctaatgtaag tgcgggttgg acttatgaag gtgtcggttg gatcgcacca   5460
acaacaagtt caagcccagt ttaccgtgtg tacaatccaa atgcattatt acacaaaaag   5520
caagtatgaa gcccaaagtt tagtaaataa gggttggaaa tgggataata acggaaaggc   5580
ggtcttctat tctggaggtt ctcaagccgt atatgtcgct tataatccca atgcacaatc   5640
tggcgctcac aattacacgg aaagtagctt tgagcaaaat agcttattga atactggttg   5700
gaaatatggg gcagtagctt ggtacgggat tggagtaaaa aacgaaatgt taaacattgc   5760
tcaaattgtt agtggtaatt tttctagtat tgttggaact tggaaagata cttctggaaa   5820
tatgcttgaa attaatgcaa tgggaaatct tactttaata tggaaagggg caaagaatca   5880
aacctttgaa cttggcgcag gtcaacaatt taatggaact gcagatattg ccttaaaaaa   5940
tggagagatt tcccctggta gtccacttaa catttttgtt gtaccaacag aagttgcttt   6000
ccctaataat aaaaaaagtag acgattcaac tgggcaacaa cgaatttttg tgaattattc   6060
tggtacaagc cctcaaatgg cgaatagtat ggcagcggtg gcttttttta gagttattcc   6120
atgattatat taaagttaga attgaataaa atgtattatt aaaaagataa tattatatca   6180
cgacaaggcg acatctatca actttaccac tggtatggaa gtgaccatta ttacatcagg   6240
aaacgctaaa acggttgttt ttacacccgt aaaataaata ataaaataat gtgaaattac   6300
tgacagcatt ttgtcagtaa ttttttttat caaaatcaca caaaaatgtt cgttgacgaa   6360
```

-continued

```
caaaaaaaac tatgttataa taattcgtat gcgaactaaa aaagaagcga ttggccgact   6420

tttaaaagta gccagcaacc aaatgtctcg agaatttgat aattttgcag ctcaacttga   6480

tttgacaggt cagcaaatgt caattttaga ttttcttgga aatcaaagcg aagaaggttc   6540

aggaaaagaa attagtcaga cgatgattga attagaattt aatatccgac gttcaacaac   6600

gacggaaatt ttacagcgca tggaaaagcg gcttttaatt aatcgaagaa caagcctgac   6660

cgatgcccgc caaaaatcag ttgaattaac tgaagaaggg aaaagatatt tacctgaaat   6720

cagggcttat atccaagcac ataataaaaa agc                                6753
```

<210> SEQ ID NO 21
<211> LENGTH: 6904
<212> TYPE: DNA
<213> ORGANISM: Lactococcus lactis
<220> FEATURE:
<221> NAME/KEY: misc_feature
<223> OTHER INFORMATION: Thy15

<400> SEQUENCE: 21

```
attaacagcc ttttgagcag ctagctcatt attttgaaat aaatcataaa tttctttccc     60

actatctgat ttatgattgc tagcatattt gttgtataat cgaacgagtc cattttgaac    120

agatccatat agattgagtg aactataaaa tacatctata tcatagttga gtttgttcac    180

aatcatgaga ccaaattctc cagcatttcg tgtagaacca cgataaagct gtttatttag    240

caaaatggca cctccgacac ctgtacctaa agtcatgcaa ataaaatttt ggctttcttg    300

tccattccct agccaaagtt cagctagacc tgcacaattg gcatcatttt caacataaac    360

cggaagattt aaatgttttt gtagttctgt ccccaatgga tagccataaa gatcagttag    420

agctcctgcc agtaataatg ttcccttttt gtcagaagtt ccgggaacac ttacaccaat    480

tgcagatact gaatgatgag cttttaactg atgaatattt gtgagcaagc tatccataat    540

tttttctttt tttaatgggg ttggaacttg taaatgttgt atgatcgttc catcactagt    600

tacaagacca aattttataa atgtaccacc gatatcaatt cctattgaat aatgcatctt    660

ttattacctc tttctctaat ttgttttagt atagcaaaat caaaaaaatta attatggtat   720

gcattataga tatgttgtat aattttcaca aaaacggaga aaactatgaa aacaatagaa    780

cagctcatga tagattcagc agatttaatg tcagatttta ttcaattgac aatttttata    840

ttccgcaagg aggattttca actttttat aggagtgatg aagaagagca agctttttca     900

aggtaatgac tccaacttat tgatagtgtt ttatgttcag ataatgcccg atgactttgt    960

catgcagctc caccgatttt gagaacgaca gcgacttccg tcccagccgt gccaggtgct   1020

gcctcagatt caggttatgc cgctcaattc gctgcgtata tcgcttgctg attacgtgca   1080

gctttccctt caggcgggat tcatacagcg gccagccatc cgtcatccat atcaccacgt   1140

caaagggtga cagcaggctc ataagacgcc ccagcgtcgc catagtgcgt tcaccgaata   1200

cgtgcgcaac aaccgtcttc cggagactgt catacgcgta aaacagccag cgctggcgcg   1260

atttagcccc gacatagccc cactgttcgt ccatttccgc gcagacgatg acgtcactgc   1320

ccggctgtat gcgcgaggtt accgactgcg gcctgagttt tttaagtgac gtaaaatcgt   1380

gttgaggcca acgcccataa tgcgggctgt tgcccggcat ccaacgccat tcatggccat   1440

atcaatgatt ttctggtgcg taccgggttg agaagcggtg taagtgaact gcagttgcca   1500

tgttttacgg cagtgagagc agagatagcg ctgatgtccg gcggtgcttt tgccgttacg   1560

caccaccccg tcagtagctg aacaggaggg acagctgata gaaacagaag ccactggagc   1620
```

-continued

```
acctcaaaaa caccatcata cactaaatca gtaagttggc agcatcaccc tttttcaaaa   1680
gaaatcatcg ctcatttatc tcagttgccc ttgaaggaag aggtgaattt attttatatg   1740
cctaagataa aaggatatat tacttatttt tctgtatttg gtaaagagga gtatcttcta   1800
cttattttta aaggacaaga aaaacttgca aataatcctt tccccgttga agtaaaacaa   1860
ttattaaaaa gtggtatttt actctatcaa atgatttttc aagaaaaatt agattatgaa   1920
gaattatttg agaaaaatca gcatattatt tctccattgc ttgctgctaa accaattgaa   1980
tggaatgatt ccaatacgtg aggaaagtaa attcccataa aacatatctt tttgaaaaat   2040
atttggggga atgtgttatt cgtggagatg ttgcagagtt aaaaaaagct tttcaaatt    2100
atatgaataa aggaactgct ggaaaattat ctaataattc aatgcgacat aagaaaaaca   2160
ttttgatttc agtcatcact atgactactc gttcggctat acagggagga ttacctgaag   2220
aagaagcttt tttgatgagt gatttatata ttcaagagct tgaagaatta acggaattag   2280
aagaaattag aacgcttgcc tataatgtga tgatcgattt tgcagataaa gtgaaacagc   2340
atcgatattg tcaggtttct tataaaatat tatcttgtca aaagtatatt gttaatcatt   2400
tatacgaaaa actaagtgtg agtgaaattg cagaagagct acacatgaat atttcttatt   2460
tatcttcaca attcaaaaaa gagacagggc aaacaattac aaactttatt caggagaagc   2520
gaatagaaga agctagagaa ttaatccttt tctcagacta tcctttttca agaatttata   2580
ccttgttggt tttactgcca aagtcatttt ataaaaatat ttaaaaaata tactggaata   2640
actcccaaaa agtttcaaga tcagtatatt tatcatgcct ctacatcaat atatgattga   2700
aattaaaaaa agacctagaa tttcaaaatt gataaaatac atacctaaaa tattaattct   2760
gtactattac gggtggagta tctactgtat aatgagggta taaattatgg aagaagggag   2820
taaaactaaa tttattgatg gttttacgaa ttaattagga tattttttt aaaaaccaaa    2880
gaaaacgctt acaaacgtta aaggagtgaa tctaaagatg gacaaatttg aaaaatggct   2940
aaataagacc ttgatgccac ttgcctcaaa aatgaataaa aatcatttca tttcggcatt   3000
aagtgaagca tttatgagat gtatgccctt aacattaggg attgcattat tgacaattat   3060
aggatacttt ccagttcctg cctgggtaga tttcttaaac tctattggac tggctcagca   3120
tttttcagca gttattggtg cagttaccag tgcgctagca atttatgtaa cttataattt   3180
tgcttattct tatgtaaatc gtcatgaata taatggccat acggccggtt tattatcaat   3240
cgcaagtttg ttaatgctaa tgccacaaat tattactgtc cctgtagtaa aaaacattcc   3300
aaccgaattt ccgaaatccg cggtagttga cagtgtgtca aatgttgaag catttcaaac   3360
ggtatacacg ggtagcacag gattaattgt agcaatcata attggtttta ttgtttcatt   3420
agtctatata caattgagca aaagaaattt agttattaaa ttaccagctg gagttcctcc   3480
aatggttgta gattcactaa gtccagcaat tatttcaatg gtgattttct gtttgatgtt   3540
cgggattcgt gtgggattct cttatacgcc attccatgat attttcaatt tctcaacaca   3600
actaattcaa gcaccgttga ctggtgctgt ggcaaatcca tgggttctta tgggcatctt   3660
tacctttggt aatttcttat ggttctttgg tatccaccct aatttaattg ggggaatttt   3720
aaatccattg ttattaacaa tgtcatatgc taatattgat gcctatgctg ccggaaaacc   3780
tgtaccatac ttacaaatga tgattgtgtt tgctgtgggt gcgaacgcat ggggcggaag   3840
tggaaatact tatgggttag ttatttcaat gtttacggca aaatctgaac gctataaaca   3900
attattaaaa ttaggtgcaa ttcctagtat tttcaatatc agtgaaccat tactttttgg   3960
tcttccaatg atgttaaatc ctcttttctt tattcctttg gttttccaac cagcaatttt   4020
```

-continued

```
aggaactgta gcattgggct tggcaaagat attatatatt acaaatctga atccaatgac   4080
ggcacttctt ccttggacga caccagcacc tgtgagaatg gccatttcag gtggacttcc   4140
atttttgatt atttttgcaa tctgtttagt cttgaatgtt cttatttact acccattctt   4200
taaggtggcg tataataaag ctttagaaga agaaaaagca gctgttgaat tagagggttc   4260
agaaactgcc tgatggatat tttttataaa tctggtttga acaaattata ttgacatctc   4320
tttttctatc ctgataattc tgagaggtta ttttgggaaa tactagatta agtcatctta   4380
cctcttttat tagtttttttc ttataatcta atgataacat ttttataatt aatctataaa   4440
ccatatccct ctttggaatc aaaatttatt atctactcct ttgtagatat gttataatac   4500
aagtatcaga tctgggagac cacaacggtt tcccactaga aataattttg tttaacttta   4560
gaaaggagat atacgcatga aaaaaaagat tatctcagct attttaatgt ctacagtcat   4620
actttctgct gcagccccgt tgtcaggtgt ttacgcctca gctggtcaag gtactcaatc   4680
agaaaactca tgtactcact ttccaggtaa cttgccaaac atgcttcgtg atttgcgtga   4740
tgctttttca cgtgttaaaa cttttttttca aatgaaagat caacttgata acttgctttt   4800
gaaagaatca cttttggaag attttaaagg ttaccttggt tgtcaagctt tgtcagaaat   4860
gatccaattt taccttgaag aagttatgcc acaagctgaa aaccaagatc cagatatcaa   4920
agctcacgtt aactcattgg gtgaaaacct taaaactttg cgtcttcgtt tgcgtcgttg   4980
tcaccgtttt cttccatgtg aaaacaaatc aaaagctgtt gaacaagtta aaaacgcttt   5040
taacaaattg caagaaaaag gtatctacaa agctatgtca gaatttgata tctttatcaa   5100
ctacatcgaa gcttacatga ctatgaaaat ccgtaactaa ctagaattaa tctataagtt   5160
actgacaaaa ctgtcagtaa cttttttttgt gggaaaaatg tatttttatg accgtaaaga   5220
atctgtcagt agaagtctga aattcgttta aaaatcgact agaataggct ttaacgacaa   5280
gatgttttaa agagtacgct ctaaatgtat ttttgtattt ttgtttgatt acgaagttta   5340
aatttaattg acaaatgttt taaaatgagt ataataggac ttgtaaccga ttttattttt   5400
ataaaggaga aagaaagatg aacaaacttt tacttggaac agcctttata ggggctagct   5460
tactgattgg tgggggtgct catgcagatc aaatgtttat cgtttgtata atcataatac   5520
tggtgagcac tctatacaac tagtgggaca ccaaaagaat gctaatgtaa gtgcgggttg   5580
gacttatgaa ggtgtcggtt ggatcgcacc aacaacaagt tcaagcccag tttaccgtgt   5640
gtacaatcca aatgcattat tacacaaaaa gcaagtatga agcccaaagt ttagtaaata   5700
agggttggaa atgggataat aacggaaagg cggtcttcta ttctggaggt tctcaagccg   5760
tatatgtcgc ttataatccc aatgcacaat ctggcgctca caattacacg gaaagtagct   5820
ttgagcaaaa tagcttattg aatactggtt ggaaatatgg ggcagtagct tggtacggga   5880
ttggagtaaa aaacgaaatg ttaaacattg ctcaaattgt tagtggtaat ttttctagta   5940
ttgttggaac ttggaaagat acttctggaa atatgcttga aattaatgca atgggaaatc   6000
ttactttaat atggaaaggg gcaaagaatc aaacctttga acttggcgca ggtcaacaat   6060
ttaatggaac tgcagatatt gccttaaaaa atggagagat ttcccctggt agtccactta   6120
acatttttgt tgtaccaaca gaagttgctt tccctaataa taaaaaagta gacgattcaa   6180
ctgggcaaca acgaattttt gtgaattatt ctggtacaag ccctcaaatg gcgaatagta   6240
tggcagcggt ggcttttttt agagttattc catgattata ttaaagttag aattgaataa   6300
aatgtattat taaaaagata atattatatc acgacaaggc gacatctatc aactttacca   6360
ctggtatgga agtgaccatt attacatcag gaaacgctaa aacggttgtt tttacacccg   6420
```

-continued

```
taaaataaat aataaaataa tgtgaaatta ctgacagcat tttgtcagta atttttttta   6480

tcaaaatcac acaaaaatgt tcgttgacga acaaaaaaaa ctatgttata ataattcgta   6540

tgcgaactaa aaaagaagcg attggccgac ttttaaaagt agccagcaac caaatgtctc   6600

gagaatttga taattttgca gctcaacttg atttgacagg tcagcaaatg tcaattttag   6660

atttcttgg aaatcaaagc gaagaaggtt caggaaaaga aattagtcag acgatgattg   6720

aattagaatt taatatccga cgttcaacaa cgacggaaat tttacagcgc atggaaaagc   6780

ggcttttaat taatcgaaga acaagcctga ccgatgcccg ccaaaaatca gttgaattaa   6840

ctgaagaagg gaaaagatat ttacctgaaa tcagggctta tatccaagca cataataaaa   6900

aagc                                                                6904
```

<210> SEQ ID NO 22
<211> LENGTH: 6964
<212> TYPE: DNA
<213> ORGANISM: Lactococcus lactis
<220> FEATURE:
<221> NAME/KEY: misc_feature
<223> OTHER INFORMATION: Thy16

<400> SEQUENCE: 22

```
attaacagcc ttttgagcag ctagctcatt attttgaaat aaatcataaa tttctttccc     60

actatctgat ttatgattgc tagcatattt gttgtataat cgaacgagtc cattttgaac    120

agatccatat agattgagtg aactataaaa tacatctata tcatagttga gtttgttcac    180

aatcatgaga ccaaattctc cagcatttcg tgtagaacca cgataaagct gtttatttag    240

caaaatggca cctccgacac ctgtacctaa agtcatgcaa ataaaatttt ggctttcttg    300

tccattccct agccaaagtt cagctagacc tgcacaattg gcatcatttt caacataaac    360

cggaagattt aaatgttttt gtagttctgt ccccaatgga tagccataaa gatcagttag    420

agctcctgcc agtaataatg ttcccttttt gtcagaagtt ccgggaacac ttacaccaat    480

tgcagatact gaatgatgag cttttaactg atgaatattt gtgagcaagc tatccataat    540

tttttctttt tttaatgggg ttggaacttg taaatgttgt atgatcgttc catcactagt    600

tacaagacca aattttataa atgtaccacc gatatcaatt cctattgaat aatgcatctt    660

ttattacctc tttctctaat ttgttttagt atagcaaaat caaaaaatta attatggtat    720

gcattataga tatgttgtat aattttcaca aaaacggaga aaactatgaa aacaatagaa    780

cagctcatga tagattcagc agatttaatg tcagatttta ttcaattgac aatttttata    840

ttccgcaagg aggattttca actttttat aggagtgatg aagaagagca agctttttca    900

aggtaatgac tccaacttat tgatagtgtt ttatgttcag ataatgcccg atgactttgt    960

catgcagctc caccgatttt gagaacgaca gcgacttccg tcccagccgt gccaggtgct   1020

gcctcagatt caggttatgc cgctcaattc gctgcgtata tcgcttgctg attacgtgca   1080

gctttccctt caggcgggat tcatacagcg gccagccatc cgtcatccat atcaccacgt   1140

caaagggtga cagcaggctc ataagacgcc ccagcgtcgc catagtgcgt tcaccgaata   1200

cgtgcgcaac aaccgtcttc cggagactgt catacgcgta aaacagccag cgctggcgcg   1260

atttagcccc gacatagccc cactgttcgt ccatttccgc gcagacgatg acgtcactgc   1320

ccggctgtat gcgcgaggtt accgactgcg gcctgagttt tttaagtgac gtaaaatcgt   1380

gttgaggcca acgcccataa tgcgggctgt tgcccggcat ccaacgccat tcatggccat   1440

atcaatgatt ttctggtgcg taccgggttg agaagcggtg taagtgaact gcagttgcca   1500
```

-continued

```
tgttttacgg cagtgagagc agagatagcg ctgatgtccg gcggtgcttt tgccgttacg   1560
caccaccccg tcagtagctg aacaggaggg acagctgata gaaacagaag ccactggagc   1620
acctcaaaaa caccatcata cactaaatca gtaagttggc agcatcaccc tttttcaaaa   1680
gaaatcatcg ctcatttatc tcagttgccc ttgaaggaag aggtgaattt attttatatg   1740
cctaagataa aaggatatat tacttatttt tctgtatttg gtaaagagga gtatcttcta   1800
cttattttta aaggacaaga aaaacttgca aataatcctt tccccgttga agtaaaacaa   1860
ttattaaaaa gtggtatttt actctatcaa atgatttttc aagaaaaatt agattatgaa   1920
gaattatttg agaaaaatca gcatattatt tctccattgc ttgctgctaa accaattgaa   1980
tggaatgatt ccaatacgtg aggaaagtaa attcccataa aacatatctt tttgaaaaat   2040
atttggggga atgtgttatt cgtggagatg ttgcagagtt aaaaaaagct ttttcaaatt   2100
atatgaataa aggaactgct ggaaaattat ctaataattc aatgcgacat aagaaaaaca   2160
ttttgatttc agtcatcact atgactactc gttcggctat acagggagga ttacctgaag   2220
aagaagcttt tttgatgagt gatttatata ttcaagagct tgaagaatta acggaattag   2280
aagaaattag aacgcttgcc tataatgtga tgatcgattt tgcagataaa gtgaaacagc   2340
atcgatattg tcaggtttct tataaaatat tatcttgtca aaagtatatt gttaatcatt   2400
tatacgaaaa actaagtgtg agtgaaattg cagaagagct acacatgaat atttcttatt   2460
tatcttcaca attcaaaaaa gagacagggc aaacaattac aaactttatt caggagaagc   2520
gaatagaaga agctagagaa ttaatccttt tctcagacta tcctttttca agaatttata   2580
ccttgttggt tttactgcca aagtcatttt ataaaaatat ttaaaaaata tactggaata   2640
actcccaaaa agtttcaaga tcagtatatt tatcatgcct ctacatcaat atatgattga   2700
aattaaaaaa agacctagaa tttcaaaatt gataaaatac atacctaaaa tattaattct   2760
gtactattac gggtggagta tctactgtat aatgagggta taaattatgg aagaagggag   2820
taaaactaaa tttattgatg gttttacgaa ttaattagga tatttttttt aaaaaccaaa   2880
gaaaacgctt acaaacgtta aaggagtgaa tctaaagatg gacaaatttg aaaaatggct   2940
aaataagacc ttgatgccac ttgcctcaaa aatgaataaa aatcatttca tttcggcatt   3000
aagtgaagca tttatgagat gtatgccctt aacattaggg attgcattat tgacaattat   3060
aggatacttt ccagttcctg cctgggtaga tttcttaaac tctattggac tggctcagca   3120
tttttcagca gttattggtg cagttaccag tgcgctagca atttatgtaa cttataattt   3180
tgcttattct tatgtaaatc gtcatgaata taatggccat acggccggtt tattatcaat   3240
cgcaagtttg ttaatgctaa tgccacaaat tattactgtc cctgtagtaa aaaacattcc   3300
aaccgaattt ccgaaatccg cggtagttga cagtgtgtca aatgttgaag catttcaaac   3360
ggtatacacg ggtagcacag gattaattgt agcaatcata attggtttta ttgtttcatt   3420
agtctatata caattgagca aaagaaattt agttattaaa ttaccagctg gagttcctcc   3480
aatggttgta gattcactaa gtccagcaat tatttcaatg gtgattttct gtttgatgtt   3540
cgggattcgt gtgggattct cttatacgcc attccatgat attttcaatt tctcaacaca   3600
actaattcaa gcaccgttga ctggtgctgt ggcaaatcca tgggttctta tgggcatctt   3660
tacctttggt aatttcttat ggttctttgg tatccaccct aatttaattg ggggaatttt   3720
aaatccattg ttattaacaa tgtcatatgc taatattgat gcctatgctg ccggaaaacc   3780
tgtaccatac ttacaaatga tgattgtgtt tgctgtgggt gcgaacgcat ggggcggaag   3840
tggaaatact tatgggttag ttatttcaat gtttacggca aaatctgaac gctataaaca   3900
```

-continued

```
attattaaaa ttaggtgcaa ttcctagtat tttcaatatc agtgaaccat tactttttgg   3960
tcttccaatg atgttaaatc ctcttttctt tattcctttg gttttccaac cagcaatttt   4020
aggaactgta gcattgggct tggcaaagat attatatatt acaaatctga atccaatgac   4080
ggcacttctt ccttggacga caccagcacc tgtgagaatg gccatttcag gtggacttcc   4140
atttttgatt atttttgcaa tctgtttagt cttgaatgtt cttatttact acccattctt   4200
taaggtggcg tataataaag ctttagaaga agaaaaagca gctgttgaat tagagggttc   4260
agaaactgcc tgatggatat tttttataaa tctggtttga acaaattata ttgacatctc   4320
tttttctatc ctgataattc tgagaggtta ttttgggaaa tactattgaa ccatatcgag   4380
gtggtgtggt ataatgaagg gaattaaaaa agataggaaa atttcgatta agtcatctta   4440
cctcttttat tagtttttc ttataatcta atgataacat ttttataatt aatctataaa   4500
ccatatccct ctttggaatc aaaatttatt atctactcct ttgtagatat gttataatac   4560
aagtatcaga tctgggagac cacaacggtt tcccactaga aataattttg tttaacttta   4620
gaaaggagat atacgcatga aaaaaaagat tatctcagct attttaatgt ctacagtcat   4680
actttctgct gcagccccgt tgtcaggtgt ttacgcctca gctggtcaag gtactcaatc   4740
agaaaactca tgtactcact ttccaggtaa cttgccaaac atgcttcgtg atttgcgtga   4800
tgctttttca cgtgttaaaa cttttttca aatgaaagat caacttgata acttgctttt   4860
gaaagaatca cttttggaag attttaaagg ttaccttggt tgtcaagctt tgtcagaaat   4920
gatccaattt taccttgaag aagttatgcc acaagctgaa aaccaagatc cagatatcaa   4980
agctcacgtt aactcattgg gtgaaaacct taaaactttg cgtcttcgtt tgcgtcgttg   5040
tcaccgtttt cttccatgtg aaaacaaatc aaaagctgtt gaacaagtta aaaacgcttt   5100
taacaaattg caagaaaaag gtatctacaa agctatgtca gaatttgata tctttatcaa   5160
ctacatcgaa gcttacatga ctatgaaaat ccgtaactaa ctagaattaa tctataagtt   5220
actgacaaaa ctgtcagtaa ctttttttgt gggaaaaatg tatttttatg accgtaaaga   5280
atctgtcagt agaagtctga aattcgttta aaaatcgact agaataggct ttaacgacaa   5340
gatgttttaa agagtacgct ctaaatgtat ttttgtattt ttgtttgatt acgaagttta   5400
aatttaattg acaaatgttt taaaatgagt ataataggac ttgtaaccga ttttattttt   5460
ataaaggaga aagaaagatg aacaaacttt tacttggaac agcctttata ggggctagct   5520
tactgattgg tgggggtgct catgcagatc aaatgtttat cgtttgtata atcataatac   5580
tggtgagcac tctatacaac tagtgggaca ccaaaagaat gctaatgtaa gtgcgggttg   5640
gacttatgaa ggtgtcggtt ggatcgcacc aacaacaagt tcaagcccag tttaccgtgt   5700
gtacaatcca aatgcattat tacacaaaaa gcaagtatga agcccaaagt ttagtaaata   5760
agggttggaa atgggataat aacggaaagg cggtcttcta ttctggaggt tctcaagccg   5820
tatatgtcgc ttataatccc aatgcacaat ctggcgctca caattacacg gaaagtagct   5880
ttgagcaaaa tagcttattg aatactggtt ggaaatatgg ggcagtagct tggtacggga   5940
ttggagtaaa aaacgaaatg ttaaacattg ctcaaattgt tagtggtaat ttttctagta   6000
ttgttggaac ttggaaagat acttctggaa atatgcttga aattaatgca atgggaaatc   6060
ttactttaat atggaaaggg gcaaagaatc aaacctttga acttggcgca ggtcaacaat   6120
ttaatggaac tgcagatatt gccttaaaaa atggagagat ttcccctggt agtccactta   6180
acatttttgt tgtaccaaca gaagttgctt tccctaataa taaaaaagta gacgattcaa   6240
ctgggcaaca acgaattttt gtgaattatt ctggtacaag ccctcaaatg gcgaatagta   6300
```

-continued

```
tggcagcggt ggcttttttt agagttattc catgattata ttaaagttag aattgaataa   6360

aatgtattat taaaaagata atattatatc acgacaaggc gacatctatc aactttacca   6420

ctggtatgga agtgaccatt attacatcag gaaacgctaa aacggttgtt tttacacccg   6480

taaaataaat aataaaataa tgtgaaatta ctgacagcat tttgtcagta attttttta    6540

tcaaaatcac acaaaaatgt tcgttgacga acaaaaaaaa ctatgttata ataattcgta   6600

tgcgaactaa aaaagaagcg attggccgac ttttaaaagt agccagcaac caaatgtctc   6660

gagaatttga taattttgca gctcaacttg atttgacagg tcagcaaatg tcaattttag   6720

attttcttgg aaatcaaagc gaagaaggtt caggaaaaga aattagtcag acgatgattg   6780

aattagaatt taatatccga cgttcaacaa cgacggaaat tttacagcgc atggaaaagc   6840

ggctttaat taatcgaaga acaagcctga ccgatgcccg ccaaaaatca gttgaattaa    6900

ctgaagaagg gaaaagatat ttacctgaaa tcagggctta tatccaagca cataataaaa   6960

aagc                                                                6964
```

<210> SEQ ID NO 23
<211> LENGTH: 4998
<212> TYPE: DNA
<213> ORGANISM: Artificial Sequence
<220> FEATURE:
<223> OTHER INFORMATION: pOThy11

<400> SEQUENCE: 23

```
aatttcatgg attaagtcat cttacctctt ttattagttt tttcttataa tctaatgata     60

acatttttat aattaatcta taaaccatat ccctctttgg aatcaaaatt tattatctac    120

tcctttgtag atatgttata atacaagtat cagatctggg agaccacaac ggtttcccac    180

tagaaataat tttgtttaac tttagaaagg agatatacgc atgaaaaaaa agattatctc    240

agctatttta atgtctacag tcatactttc tgctgcagcc ccgttgtcag gtgtttacgc    300

ctcagctggt caaggtactc aatcagaaaa ctcatgtact cactttccag gtaacttgcc    360

aaacatgctt cgtgatttgc gtgatgcttt ttcacgtgtt aaaacttttt ttcaaatgaa    420

agatcaactt gataacttgc ttttgaaaga atcacttttg gaagatttta aaggttacct    480

tggttgtcaa gctttgtcag aaatgatcca attttacctt gaagaagtta tgccacaagc    540

tgaaaaccaa gatccagata tcaaagctca cgttaactca ttgggtgaaa accttaaaac    600

tttgcgtctt cgtttgcgtc gttgtcaccg ttttcttcca tgtgaaaaca aatcaaaagc    660

tgttgaacaa gttaaaaacg cttttaacaa attgcaagaa aaaggtatct acaaagctat    720

gtcagaattt gatatcttta tcaactacat cgaagcttac atgactatga aaatccgtaa    780

ctaactagaa ttaatctata agttactgac aaaactgtca gtaacttttt ttgtgggaaa    840

aatgtatttt tatgaccgta aagaatctgt cagtagaagt ctgaaattcg tttaaaaatc    900

gactagaata ggctttaacg acaagatgtt ttaaagagta cgctctaaat gtatttttgt    960

atttttgttt gattacgaag tttaaattta attgacaaat gttttaaaat gagtataata   1020

ggacttgtaa ccgattttat ttttataaag gagaaagaaa gatgaacaaa cttttacttg   1080

gaacagcctt tatagggggct agcttactga ttggtggggg tgctcatgca gatcaaatgt  1140

ttatcgtttg tataatcata atactggtga gcactctata caactagtgg gacaccaaaa   1200

gaatgctaat gtaagtgcgg gttggactta tgaaggtgtc ggttggatcg caccaacaac   1260

aagttcaagc ccagtttacc gtgtgtacaa tccaaatgca ttattacaca aaaagcaagt   1320

atgaagccca aagtttagta aataagggtt ggaaatggga taataacgga aaggcggtct   1380
```

-continued

```
tctattctgg aggttctcaa gccgtatatg tcgcttataa tcccaatgca caatctggcg   1440
ctcacaatta cacggaaagt agctttgagc aaaatagctt attgaatact ggttggaaat   1500
atggggcagt agcttggtac gggattggag taaaaaacga aatgttaaac attgctcaaa   1560
ttgttagtgg taatttttct agtattgttg gaacttggaa agatacttct ggaaatatgc   1620
ttgaaattaa tgcaatggga aatcttactt taatatggaa aggggcaaag aatcaaacct   1680
ttgaacttgg cgcaggtcaa caatttaatg gaactgcaga tattgcctta aaaaatggag   1740
agatttcccc tggtagtcca cttaacattt ttgttgtacc aacagaagtg aattcactgg   1800
ccgtcgtttt acaacgtcgt gactgggaaa accctggcgt tacccaactt aatcgccttg   1860
cagcacatcc ccctttcgcc agctggcgta atagcgaaga ggcccgcacc gatcgccctt   1920
cccaacagtt gcgcagcctg aatggcgaat ggcgcctgat gcggtatttt ctccttacgc   1980
atctgtgcgg tatttcacac cgcatatggt gcactagaac tagcgattct gaaatcacca   2040
tttaaaaaac tccaatcaaa taattttata aagttagtgt atcactttgt aatcataaaa   2100
acaacaataa agctacttaa atatagattt ataaaaaacg ttggcgaaaa cgttggcgat   2160
tcgttggcga ttgaaaaacc ccttaaaccc ttgagccagt tgggatagag cgtttttggc   2220
acaaaaattg gcactcggca cttaatgggg ggtcgtagta cggaagcaaa attcgcttcc   2280
tttcccccca ttttttttcca aattccaaat ttttttcaaa aattttccag cgctaccgct   2340
cggcaaaatt gcaagcaatt tttaaaatca aacccatgag ggaatttcat tccctcatac   2400
tcccttgagc ctcctccaac cgaaatagaa gggcgctgcg cttattattt cattcagtca   2460
tcggctttca taatctaaca gacaacatct tcgctgcaaa gccacgctac gctcaagggc   2520
ttttacgcta cgataacgcc tgttttaacg attatgccga taactaaacg aaataaacgc   2580
taaaacgtct cagaaacgat tttgagacgt tttaataaaa aatcgctagt ccgaggcctc   2640
gacccgattc acaaaaaata ggcacacgaa aaacaagtta agggatgcag tttatgcatc   2700
ccttaactta cttattaaat aatttatagc tattgaaaag agataagaat tgttcaaagc   2760
taatattgtt taaatcgtca attcctgcat gttttaagga attgttaaat tgatttttttg   2820
taaatatttt cttgtattct ttgttaaccc atttcataac gaaataatta tacttttgtt   2880
tatctttgtg tgatattctt gatttttttc tacttaatct gataagtgag ctattcactt   2940
taggtttagg atgaaaatat tctcttggaa ccatacttaa tatagaaata tcaacttctg   3000
ccattaaaag taatgccaat gagcgttttg tatttaataa tcttttagca aacccgtatt   3060
ccacgattaa ataaatctca ttagctatac tatcaaaaac aattttgcgt attatatccg   3120
tacttatgtt ataaggtata ttaccatata ttttatagga ttggttttta ggaaatttaa   3180
actgcaatat atccttgttt aaaacttgga aattatcgtg atcaacaagt ttattttctg   3240
tagttttgca taatttatgg tctatttcaa tggcagttac gaaattacac ctctttacta   3300
attcaagggt aaaatggcct tttcctgagc cgatttcaaa gatattatca tgttcattta   3360
atcttatatt tgtcattatt ttatctatat tatgttttga agtaataaag ttttgactgt   3420
gttttatatt tttctcgttc attataaccc tctttaattt ggttatatga attttgctta   3480
ttaacgattc attataacca cttatttttt gtttggttga taatgaactg tgctgattac   3540
aaaaatacta aaaatgccca tatttttttcc tccttataaa attagtataa ttatagcacg   3600
ggtcgagatc catgttcttt cctgcgttat cccctgattc tgtggataac cgtattaccg   3660
cctttgagtg agctgatacc gctcgccgca gccgaacgac cgagcgcagc gagtcagtga   3720
gcgaggaagc ggaagagcgc ccaatacgca aaccgcctct ccccgcgcgt tggccgattc   3780
```

-continued

```
attaatgcag ctggcacgac aggtttcccg actggaaagc gggcagtgag cgcaacgcaa   3840
ttaatgtgag ttagctcact cattaggcac cccaggcttt acactttatg cttccggctc   3900
gtatgttgtg tggaattgtg agcggataac aatttcacac aggaaacagc tatgaccatg   3960
attacgccaa gcttgcatgc ctgcaggtcg actctagagg atcctatata caattgagca   4020
aaagaaattt agttattaaa ttaccagctg gagttcctcc aatggttgta gattcactaa   4080
gtccagcaat tatttcaatg gtgattttct gtttgatgtt cgggattcgt gtgggattct   4140
cttatacgcc attccatgat attttcaatt tctcaacaca actaattcaa gcaccgttga   4200
ctggtgctgt ggcaaatcca tgggttctta tgggcatctt tacctttggt aatttcttat   4260
ggttctttgg tatccaccct aatttaattg gggaatttt aaatccattg ttattaacaa   4320
tgtcatatgc taatattgat gcctatgctg ccggaaaacc tgtaccatac ttacaaatga   4380
tgattgtgtt tgctgtgggt gcgaacgcat ggggcggaag tggaaatact tatgggttag   4440
ttatttcaat gtttacggca aaatctgaac gctataaaca attattaaaa ttaggtgcaa   4500
ttcctagtat tttcaatatc agtgaaccat tactttttgg tcttccaatg atgttaaatc   4560
ctcttttctt tattcctttg gttttccaac cagcaatttt aggaactgta gcattgggct   4620
tggcaaagat attatatatt acaaatctga atccaatgac ggcacttctt ccttggacga   4680
caccagcacc tgtgagaatg gccatttcag gtggacttcc atttttgatt atttttgcaa   4740
tctgtttagt cttgaatgtt cttatttact acccattctt taaggtggcg tataataaag   4800
ctttagaaga agaaaaagca gctgttgaat tagagggttc agaaactgcc tgatggatat   4860
tttttataaa tctggtttga acaaattata ttgacatctc tttttctatc ctgataattc   4920
tgagaggtta ttttgggaaa tactattgaa ccatatcgag gtgtgtggta taatgaaggg   4980
aattaaaaaa gataggaa                                                 4998
```

<210> SEQ ID NO 24
<211> LENGTH: 4784
<212> TYPE: DNA
<213> ORGANISM: Artificial Sequence
<220> FEATURE:
<223> OTHER INFORMATION: pOThy12

<400> SEQUENCE: 24

```
gggttcagaa actgcctgat ggatattttt tataaatctg gtttgaacaa attatattga     60
catctctttt tctatcctga taattctgag aggttattt gggaaatact attgaaccat    120
atcgaggtgt gtggtataat gaagggaatt aaaaaagata ggaaaatttc atgaaaaaaa    180
agattatctc agctatttta atgtctacag tcatactttc tgctgcagcc ccgttgtcag    240
gtgtttacgc ctcagctggt caaggtactc aatcagaaaa ctcatgtact cactttccag    300
gtaacttgcc aaacatgctt cgtgatttgc gtgatgcttt ttcacgtgtt aaaacttttt    360
ttcaaatgaa agatcaactt gataacttgc ttttgaaaga atcacttttg gaagatttta    420
aaggttacct tggttgtcaa gctttgtcag aaatgatcca attttacctt gaagaagtta    480
tgccacaagc tgaaaaccaa gatccagata tcaaagctca cgttaactca ttgggtgaaa    540
accttaaaac tttgcgtctt cgtttgcgtc gttgtcaccg ttttcttcca tgtgaaaaca    600
aatcaaaagc tgttgaacaa gttaaaaacg cttttaacaa attgcaagaa aaaggtatct    660
acaaagctat gtcagaattt gatatcttta tcaactacat cgaagcttac atgactatga    720
aaatccgtaa ctaactagaa ttaatctata agttactgac aaaactgtca gtaacttttt    780
ttgtgggaaa aatgtatttt tatgaccgta aagaatctgt cagtagaagt ctgaaattcg    840
```

-continued

```
tttaaaaatc gactagaata ggctttaacg acaagatgtt ttaaagagta cgctctaaat    900
gtatttttgt atttttgttt gattacgaag tttaaattta attgacaaat gttttaaaat    960
gagtataata ggacttgtaa ccgattttat ttttataaag gagaaagaaa gatgaacaaa   1020
cttttacttg gaacagcctt tataggggct agcttactga ttggtggggg tgctcatgca   1080
gatcaaatgt ttatcgtttg tataatcata atactggtga gcactctata caactagtgg   1140
gacaccaaaa gaatgctaat gtaagtgcgg gttggactta tgaaggtgtc ggttggatcg   1200
caccaacaac aagttcaagc ccagtttacc gtgtgtacaa tccaaatgca ttattacaca   1260
aaaagcaagt atgaagccca aagtttagta aataagggtt ggaaatggga taataacgga   1320
aaggcggtct tctattctgg aggttctcaa gccgtatatg tcgcttataa tcccaatgca   1380
caatctggcg ctcacaatta cacggaaagt agctttgagc aaaatagctt attgaatact   1440
ggttggaaat atggggcagt agcttggtac gggattggag taaaaaacga aatgttaaac   1500
attgctcaaa ttgttagtgg taatttttct agtattgttg gaacttggaa agatacttct   1560
ggaaatatgc ttgaaattaa tgcaatggga aatcttactt taatatggaa aggggcaaag   1620
aatcaaacct ttgaacttgg cgcaggtcaa caatttaatg gaactgcaga tattgcctta   1680
aaaaatggag agatttcccc tggtagtcca cttaacattt ttgttgtacc aacagaagtg   1740
aattcactgg ccgtcgtttt acaacgtcgt gactgggaaa accctggcgt tacccaactt   1800
aatcgccttg cagcacatcc ccctttcgcc agctggcgta atagcgaaga ggcccgcacc   1860
gatcgccctt cccaacagtt gcgcagcctg aatggcgaat ggcgcctgat gcggtatttt   1920
ctccttacgc atctgtgcgg tatttcacac cgcatatggt gcactagaac tagcgattct   1980
gaaatcacca tttaaaaaac tccaatcaaa taattttata aagttagtgt atcactttgt   2040
aatcataaaa acaacaataa agctacttaa atatagattt ataaaaaacg ttggcgaaaa   2100
cgttggcgat tcgttggcga ttgaaaaacc ccttaaaccc ttgagccagt tgggatagag   2160
cgtttttggc acaaaaattg gcactcggca cttaatgggg ggtcgtagta cggaagcaaa   2220
attcgcttcc tttcccccca ttttttttcca aattccaaat ttttttcaaa aatttttccag   2280
cgctaccgct cggcaaaatt gcaagcaatt tttaaaatca aacccatgag ggaatttcat   2340
tccctcatac tcccttgagc ctcctccaac cgaaatagaa gggcgctgcg cttattattt   2400
cattcagtca tcggctttca taatctaaca gacaacatct tcgctgcaaa gccacgctac   2460
gctcaagggc ttttacgcta cgataacgcc tgttttaacg attatgccga taactaaacg   2520
aaataaacgc taaaacgtct cagaaacgat tttgagacgt tttaataaaa aatcgctagt   2580
ccgaggcctc gacccgattc acaaaaaata ggcacacgaa aaacaagtta agggatgcag   2640
tttatgcatc ccttaactta cttattaaat aatttatagc tattgaaaag agataagaat   2700
tgttcaaagc taatattgtt taaatcgtca attcctgcat gttttaagga attgttaaat   2760
tgatttttttg taaatatttt cttgtattct ttgttaaccc atttcataac gaaataatta   2820
tacttttgtt tatctttgtg tgatattctt gattttttttc tacttaatct gataagtgag   2880
ctattcactt taggtttagg atgaaaatat tctcttggaa ccatacttaa tatagaaata   2940
tcaacttctg ccattaaaag taatgccaat gagcgttttg tatttaataa tcttttagca   3000
aacccgtatt ccacgattaa ataaatctca ttagctatac tatcaaaaac aattttgcgt   3060
attatatccg tacttatgtt ataaggtata ttaccatata ttttatagga ttggttttta   3120
ggaaatttaa actgcaatat atccttgttt aaaacttgga aattatcgtg atcaacaagt   3180
ttattttctg tagttttgca taatttatgg tctatttcaa tggcagttac gaaattacac   3240
```

-continued

```
ctctttacta attcaagggt aaaatggcct tttcctgagc cgatttcaaa gatattatca   3300

tgttcattta atcttatatt tgtcattatt ttatctatat tatgttttga agtaataaag   3360

ttttgactgt gttttatatt tttctcgttc attataaccc tctttaattt ggttatatga   3420

attttgctta ttaacgattc attataacca cttatttttt gtttggttga taatgaactg   3480

tgctgattac aaaaatacta aaaatgccca tattttttcc tccttataaa attagtataa   3540

ttatagcacg ggtcgagatc catgttcttt cctgcgttat cccctgattc tgtggataac   3600

cgtattaccg cctttgagtg agctgatacc gctcgccgca gccgaacgac cgagcgcagc   3660

gagtcagtga gcgaggaagc ggaagagcgc ccaatacgca aaccgcctct ccccgcgcgt   3720

tggccgattc attaatgcag ctggcacgac aggtttcccg actggaaagc gggcagtgag   3780

cgcaacgcaa ttaatgtgag ttagctcact cattaggcac cccaggcttt acactttatg   3840

cttccggctc gtatgttgtg tggaattgtg agcggataac aatttcacac aggaaacagc   3900

tatgaccatg attacgccaa gcttgcatgc ctgcaggtcg actctagagg atcctatata   3960

caattgagca aaagaaattt agttattaaa ttaccagctg gagttcctcc aatggttgta   4020

gattcactaa gtccagcaat tatttcaatg gtgattttct gtttgatgtt cgggattcgt   4080

gtgggattct cttatacgcc attccatgat attttcaatt tctcaacaca actaattcaa   4140

gcaccgttga ctggtgctgt ggcaaatcca tgggttctta tgggcatctt tacctttggt   4200

aatttcttat ggttctttgg tatccaccct aatttaattg gggaatttt aaatccattg    4260

ttattaacaa tgtcatatgc taatattgat gcctatgctg ccggaaaacc tgtaccatac   4320

ttacaaatga tgattgtgtt tgctgtgggt gcgaacgcat ggggcggaag tggaaatact   4380

tatgggttag ttatttcaat gtttacggca aaatctgaac gctataaaca attattaaaa   4440

ttaggtgcaa ttcctagtat tttcaatatc agtgaaccat tactttttgg tcttccaatg   4500

atgttaaatc ctcttttctt tattcctttg gttttccaac cagcaatttt aggaactgta   4560

gcattgggct tggcaaagat attatatatt acaaatctga atccaatgac ggcacttctt   4620

ccttggacga caccagcacc tgtgagaatg gccatttcag gtggacttcc atttttgatt   4680

atttttgcaa tctgtttagt cttgaatgtt cttatttact acccattctt taaggtggcg   4740

tataataaag ctttagaaga agaaaaagca gctgttgaat taga                    4784
```

<210> SEQ ID NO 25
<211> LENGTH: 4936
<212> TYPE: DNA
<213> ORGANISM: Artificial Sequence
<220> FEATURE:
<223> OTHER INFORMATION: pOThy15

<400> SEQUENCE: 25

```
gattaagtca tcttacctct tttattagtt ttttcttata atctaatgat aacattttta     60

taattaatct ataaaccata tccctctttg gaatcaaaat ttattatcta ctcctttgta    120

gatatgttat aatacaagta tcagatctgg gagaccacaa cggtttccca ctagaaataa    180

ttttgtttaa ctttagaaag gagatatacg catgaaaaaa aagattatct cagctatttt    240

aatgtctaca gtcatacttt ctgctgcagc cccgttgtca ggtgtttacg cctcagctgg    300

tcaaggtact caatcagaaa actcatgtac tcactttcca ggtaacttgc caaacatgct    360

tcgtgatttg cgtgatgctt tttcacgtgt taaaactttt tttcaaatga aagatcaact    420

tgataacttg cttttgaaag aatcactttt ggaagatttt aaaggttacc ttggttgtca    480

agctttgtca gaaatgatcc aattttacct tgaagaagtt atgccacaag ctgaaaacca    540
```

-continued

```
agatccagat atcaaagctc acgttaactc attgggtgaa aaccttaaaa ctttgcgtct    600
tcgtttgcgt cgttgtcacc gttttcttcc atgtgaaaac aaatcaaaag ctgttgaaca    660
agttaaaaac gcttttaaca aattgcaaga aaaaggtatc tacaaagcta tgtcagaatt    720
tgatatcttt atcaactaca tcgaagctta catgactatg aaaatccgta actaactaga    780
attaatctat aagttactga caaaactgtc agtaactttt tttgtgggaa aaatgtattt    840
ttatgaccgt aaagaatctg tcagtagaag tctgaaattc gtttaaaaat cgactagaat    900
aggctttaac gacaagatgt tttaaagagt acgctctaaa tgtatttttg tatttttgtt    960
tgattacgaa gtttaaattt aattgacaaa tgttttaaaa tgagtataat aggacttgta   1020
accgatttta tttttataaa ggagaaagaa agatgaacaa acttttactt ggaacagcct   1080
ttataggggc tagcttactg attggtgggg gtgctcatgc agatcaaatg tttatcgttt   1140
gtataatcat aatactggtg agcactctat acaactagtg ggacaccaaa agaatgctaa   1200
tgtaagtgcg ggttggactt atgaaggtgt cggttggatc gcaccaacaa caagttcaag   1260
cccagtttac cgtgtgtaca atccaaatgc attattacac aaaaagcaag tatgaagccc   1320
aaagtttagt aaataagggt tggaaatggg ataataacgg aaaggcggtc ttctattctg   1380
gaggttctca agccgtatat gtcgcttata atcccaatgc acaatctggc gctcacaatt   1440
acacggaaag tagctttgag caaaatagct tattgaatac tggttggaaa tatggggcag   1500
tagcttggta cgggattgga gtaaaaaacg aaatgttaaa cattgctcaa attgttagtg   1560
gtaatttttc tagtattgtt ggaacttgga aagatacttc tggaaatatg cttgaaatta   1620
atgcaatggg aaatcttact ttaatatgga aaggggcaaa gaatcaaacc tttgaacttg   1680
gcgcaggtca acaatttaat ggaactgcag atattgcctt aaaaaatgga gagatttccc   1740
ctggtagtcc acttaacatt tttgttgtac caacagaagt gaattcactg gccgtcgttt   1800
tacaacgtcg tgactgggaa aaccctggcg ttacccaact taatcgcctt gcagcacatc   1860
ccccttttcgc cagctggcgt aatagcgaag aggcccgcac cgatcgccct tcccaacagt   1920
tgcgcagcct gaatggcgaa tggcgcctga tgcggtattt tctccttacg catctgtgcg   1980
gtatttcaca ccgcatatgg tgcactagaa ctagcgattc tgaaatcacc atttaaaaaa   2040
ctccaatcaa ataattttat aaagttagtg tatcactttg taatcataaa aacaacaata   2100
aagctactta aatatagatt tataaaaaac gttggcgaaa acgttggcga ttcgttggcg   2160
attgaaaaac cccttaaacc cttgagccag ttgggataga gcgtttttgg cacaaaaatt   2220
ggcactcggc acttaatggg gggtcgtagt acggaagcaa aattcgcttc ctttcccccc   2280
atttttttcc aaattccaaa tttttttcaa aaattttcca gcgctaccgc tcggcaaaat   2340
tgcaagcaat ttttaaaatc aaacccatga gggaatttca ttccctcata ctcccttgag   2400
cctcctccaa ccgaaataga agggcgctgc gcttattatt tcattcagtc atcggctttc   2460
ataatctaac agacaacatc ttcgctgcaa agccacgcta cgctcaaggg cttttacgct   2520
acgataacgc ctgttttaac gattatgccg ataactaaac gaaataaacg ctaaaacgtc   2580
tcagaaacga ttttgagacg ttttaataaa aaatcgctag tccgaggcct cgacccgatt   2640
cacaaaaaat aggcacacga aaaacaagtt aagggatgca gtttatgcat cccttaactt   2700
acttattaaa taatttatag ctattgaaaa gagataagaa ttgttcaaag ctaatattgt   2760
ttaaatcgtc aattcctgca tgttttaagg aattgttaaa ttgatttttt gtaaatattt   2820
tcttgtattc tttgttaacc catttcataa cgaaataatt atacttttgt ttatctttgt   2880
gtgatattct tgattttttt ctacttaatc tgataagtga gctattcact ttaggtttag   2940
```

-continued

```
gatgaaaata ttctcttgga accatactta atatagaaat atcaacttct gccattaaaa   3000

gtaatgccaa tgagcgtttt gtatttaata atcttttagc aaacccgtat tccacgatta   3060

aataaatctc attagctata ctatcaaaaa caattttgcg tattatatcc gtacttatgt   3120

tataaggtat attaccatat attttatagg attggttttt aggaaattta aactgcaata   3180

tatccttgtt taaaacttgg aaattatcgt gatcaacaag tttattttct gtagttttgc   3240

ataatttatg gtctatttca atggcagtta cgaaattaca cctctttact aattcaaggg   3300

taaaatggcc ttttcctgag ccgatttcaa agatattatc atgttcattt aatcttatat   3360

ttgtcattat tttatctata ttatgttttg aagtaataaa gttttgactg tgttttatat   3420

ttttctcgtt cattataacc ctctttaatt tggttatatg aattttgctt attaacgatt   3480

cattataacc acttattttt tgtttggttg ataatgaact gtgctgatta caaaaatact   3540

aaaaatgccc atatttttc ctccttataa aattagtata attatagcac gggtcgagat   3600

ccatgttctt tcctgcgtta tcccctgatt ctgtggataa ccgtattacc gcctttgagt   3660

gagctgatac cgctcgccgc agccgaacga ccgagcgcag cgagtcagtg agcgaggaag   3720

cggaagagcg cccaatacgc aaaccgcctc tccccgcgcg ttggccgatt cattaatgca   3780

gctggcacga caggtttccc gactggaaag cgggcagtga gcgcaacgca attaatgtga   3840

gttagctcac tcattaggca ccccaggctt tacactttat gcttccggct cgtatgttgt   3900

gtggaattgt gagcggataa caatttcaca caggaaacag ctatgaccat gattacgcca   3960

agcttgcatg cctgcaggtc gactctagag gatcctatat acaattgagc aaaagaaatt   4020

tagttattaa attaccagct ggagttcctc caatggttgt agattcacta agtccagcaa   4080

ttatttcaat ggtgattttc tgtttgatgt tcgggattcg tgtgggattc tcttatacgc   4140

cattccatga tattttcaat ttctcaacac aactaattca agcaccgttg actggtgctg   4200

tggcaaatcc atgggttctt atgggcatct ttacctttgg taatttctta tggttctttg   4260

gtatccaccc taatttaatt gggggaattt taaatccatt gttattaaca atgtcatatg   4320

ctaatattga tgcctatgct gccggaaaac ctgtaccata cttacaaatg atgattgtgt   4380

ttgctgtggg tgcgaacgca tggggcggaa gtggaaatac ttatgggtta gttatttcaa   4440

tgtttacggc aaaatctgaa cgctataaac aattattaaa attaggtgca attcctagta   4500

ttttcaatat cagtgaacca ttactttttg gtcttccaat gatgttaaat cctcttttct   4560

ttattccttt ggttttccaa ccagcaattt taggaactgt agcattgggc ttggcaaaga   4620

tattatatat tacaaatctg aatccaatga cggcacttct tccttggacg acaccagcac   4680

ctgtgagaat ggccatttca ggtggacttc catttttgat tatttttgca atctgtttag   4740

tcttgaatgt tcttatttac tacccattct ttaaggtggc gtataataaa gctttagaag   4800

aagaaaaagc agctgttgaa ttagagggtt cagaaactgc ctgatggata ttttttataa   4860

atctggtttg aacaaattat attgacatct ctttttctat cctgataatt ctgagaggtt   4920

attttgggaa atacta                                                   4936
```

<210> SEQ ID NO 26
<211> LENGTH: 4995
<212> TYPE: DNA
<213> ORGANISM: Artificial Sequence
<220> FEATURE:
<223> OTHER INFORMATION: pOThy16

-continued

<400> SEQUENCE: 26

```
aatttcgatt aagtcatctt acctctttta ttagtttttt cttataatct aatgataaca     60
tttttataat taatctataa accatatccc tctttggaat caaaatttat tatctactcc    120
tttgtagata tgttataata caagtatcag atctgggaga ccacaacggt ttcccactag    180
aaataatttt gtttaacttt agaaaggaga tatacgcatg aaaaaaaaga ttatctcagc    240
tattttaatg tctacagtca tactttctgc tgcagccccg ttgtcaggtg tttacgcctc    300
agctggtcaa ggtactcaat cagaaaactc atgtactcac tttccaggta acttgccaaa    360
catgcttcgt gatttgcgtg atgctttttc acgtgttaaa actttttttc aaatgaaaga    420
tcaacttgat aacttgcttt tgaaagaatc acttttggaa gattttaaag gttaccttgg    480
ttgtcaagct ttgtcagaaa tgatccaatt ttaccttgaa gaagttatgc cacaagctga    540
aaaccaagat ccagatatca aagctcacgt taactcattg ggtgaaaacc ttaaaacttt    600
gcgtcttcgt ttgcgtcgtt gtcaccgttt tcttccatgt gaaaacaaat caaaagctgt    660
tgaacaagtt aaaaacgctt ttaacaaatt gcaagaaaaa ggtatctaca aagctatgtc    720
agaatttgat atctttatca actacatcga agcttacatg actatgaaaa tccgtaacta    780
actagaatta atctataagt tactgacaaa actgtcagta actttttttg tgggaaaaat    840
gtatttttat gaccgtaaag aatctgtcag tagaagtctg aaattcgttt aaaaatcgac    900
tagaataggc tttaacgaca agatgtttta aagagtacgc tctaaatgta tttttgtatt    960
tttgtttgat tacgaagttt aaatttaatt gacaaatgtt ttaaaatgag tataatagga   1020
cttgtaaccg attttatttt tataaaggag aaagaaagat gaacaaactt ttacttggaa   1080
cagcctttat aggggctagc ttactgattg gtgggggtgc tcatgcagat caaatgttta   1140
tcgtttgtat aatcataata ctggtgagca ctctatacaa ctagtgggac accaaaagaa   1200
tgctaatgta agtgcgggtt ggacttatga aggtgtcggt tggatcgcac caacaacaag   1260
ttcaagccca gtttaccgtg tgtacaatcc aaatgcatta ttacacaaaa agcaagtatg   1320
aagcccaaag tttagtaaat aagggttgga aatgggataa taacggaaag gcggtcttct   1380
attctggagg ttctcaagcc gtatatgtcg cttataatcc caatgcacaa tctggcgctc   1440
acaattacac ggaaagtagc tttgagcaaa atagcttatt gaatactggt tggaaatatg   1500
gggcagtagc ttggtacggg attggagtaa aaaacgaaat gttaaacatt gctcaaattg   1560
ttagtggtaa tttttctagt attgttggaa cttggaaaga tacttctgga aatatgcttg   1620
aaattaatgc aatgggaaat cttactttaa tatggaaagg ggcaaagaat caaacctttg   1680
aacttggcgc aggtcaacaa tttaatggaa ctgcagatat tgccttaaaa aatggagaga   1740
tttcccctgg tagtccactt aacatttttg ttgtaccaac agaagtgaat tcactggccg   1800
tcgttttaca acgtcgtgac tgggaaaacc ctggcgttac ccaacttaat cgccttgcag   1860
cacatccccc tttcgccagc tggcgtaata gcgaagaggc ccgcaccgat cgcccttccc   1920
aacagttgcg cagcctgaat ggcgaatggc gcctgatgcg gtattttctc cttacgcatc   1980
tgtgcggtat ttcacaccgc atatggtgca ctagaactag cgattctgaa atcaccattt   2040
aaaaaactcc aatcaaataa ttttataaag ttagtgtatc actttgtaat cataaaaaca   2100
acaataaagc tacttaaata tagatttata aaaaacgttg gcgaaaacgt tggcgattcg   2160
ttggcgattg aaaaacccct taaacccttg agccagttgg gatagagcgt tttggcaca    2220
aaaattggca ctcggcactt aatggggggt cgtagtacgg aagcaaaatt cgcttccttt   2280
ccccccattt ttttccaaat tccaaatttt tttcaaaaat tttccagcgc taccgctcgg   2340
```

-continued

```
caaaattgca agcaattttt aaaatcaaac ccatgaggga atttcattcc ctcatactcc   2400
cttgagcctc ctccaaccga aatagaaggg cgctgcgctt attatttcat tcagtcatcg   2460
gctttcataa tctaacagac aacatcttcg ctgcaaagcc acgctacgct caagggcttt   2520
tacgctacga taacgcctgt tttaacgatt atgccgataa ctaaacgaaa taaacgctaa   2580
aacgtctcag aaacgatttt gagacgtttt aataaaaaat cgctagtccg aggcctcgac   2640
ccgattcaca aaaaataggc acacgaaaaa caagttaagg gatgcagttt atgcatccct   2700
taacttactt attaaataat ttatagctat tgaaaagaga taagaattgt tcaaagctaa   2760
tattgtttaa atcgtcaatt cctgcatgtt ttaaggaatt gttaaattga ttttttgtaa   2820
atattttctt gtattctttg ttaacccatt tcataacgaa ataattatac ttttgtttat   2880
ctttgtgtga tattcttgat ttttttctac ttaatctgat aagtgagcta ttcactttag   2940
gtttaggatg aaaatattct cttggaacca tacttaatat agaaatatca acttctgcca   3000
ttaaaagtaa tgccaatgag cgttttgtat ttaataatct tttagcaaac ccgtattcca   3060
cgattaaata aatctcatta gctatactat caaaaacaat tttgcgtatt atatccgtac   3120
ttatgttata aggtatatta ccatatattt tataggattg gtttttagga aatttaaact   3180
gcaatatatc cttgtttaaa acttggaaat tatcgtgatc aacaagttta ttttctgtag   3240
ttttgcataa tttatggtct atttcaatgg cagttacgaa attacacctc tttactaatt   3300
caagggtaaa atggcctttt cctgagccga tttcaaagat attatcatgt tcatttaatc   3360
ttatatttgt cattatttta tctatattat gttttgaagt aataaagttt tgactgtgtt   3420
ttatattttt ctcgttcatt ataaccctct ttaatttggt tatatgaatt ttgcttatta   3480
acgattcatt ataaccactt atttttgtt tggttgataa tgaactgtgc tgattacaaa   3540
aatactaaaa atgcccatat tttttcctcc ttataaaatt agtataatta tagcacgggt   3600
cgagatccat gttctttcct gcgttatccc ctgattctgt ggataaccgt attaccgcct   3660
ttgagtgagc tgataccgct cgccgcagcc gaacgaccga gcgcagcgag tcagtgagcg   3720
aggaagcgga agagcgccca atacgcaaac cgcctctccc cgcgcgttgg ccgattcatt   3780
aatgcagctg gcacgacagg tttcccgact ggaaagcggg cagtgagcgc aacgcaatta   3840
atgtgagtta gctcactcat taggcacccc aggctttaca ctttatgctt ccggctcgta   3900
tgttgtgtgg aattgtgagc ggataacaat ttcacacagg aaacagctat gaccatgatt   3960
acgccaagct tgcatgcctg caggtcgact ctagaggatc ctatatacaa ttgagcaaaa   4020
gaaatttagt tattaaatta ccagctggag ttcctccaat ggttgtagat tcactaagtc   4080
cagcaattat ttcaatggtg attttctgtt tgatgttcgg gattcgtgtg ggattctctt   4140
atacgccatt ccatgatatt ttcaatttct caacacaact aattcaagca ccgttgactg   4200
gtgctgtggc aaatccatgg gttcttatgg gcatctttac ctttggtaat ttcttatggt   4260
tctttggtat ccaccctaat ttaattgggg gaattttaaa tccattgtta ttaacaatgt   4320
catatgctaa tattgatgcc tatgctgccg gaaaacctgt accatactta caaatgatga   4380
ttgtgtttgc tgtgggtgcg aacgcatggg gcggaagtgg aaatacttat gggttagtta   4440
tttcaatgtt tacggcaaaa tctgaacgct ataaacaatt attaaaatta ggtgcaattc   4500
ctagtatttt caatatcagt gaaccattac tttttggtct tccaatgatg ttaaatcctc   4560
ttttctttat tcctttggtt ttccaaccag caattttagg aactgtagca ttgggcttgg   4620
caaagatatt atatattaca aatctgaatc caatgacggc acttcttcct tggacgacac   4680
cagcacctgt gagaatggcc atttcaggtg gacttccatt tttgattatt tttgcaatct   4740
```

-continued

```
gtttagtctt gaatgttctt atttactacc cattctttaa ggtggcgtat aataaagctt   4800

tagaagaaga aaaagcagct gttgaattag agggttcaga aactgcctga tggatatttt   4860

ttataaatct ggtttgaaca aattatattg acatctcttt ttctatcctg ataattctga   4920

gaggttattt tgggaaatac tattgaacca tatcgaggtg tgtggtataa tgaagggaat   4980

taaaaaagat aggaa                                                    4995


<210> SEQ ID NO 27
<211> LENGTH: 39
<212> TYPE: DNA
<213> ORGANISM: Artificial Sequence
<220> FEATURE:
<223> OTHER INFORMATION: lactococcal P1 promoter expression unit

<400> SEQUENCE: 27

agataggaaa atttcatgac ttacgcagat caagttttt                            39


<210> SEQ ID NO 28
<211> LENGTH: 36
<212> TYPE: DNA
<213> ORGANISM: Artificial Sequence
<220> FEATURE:
<223> OTHER INFORMATION: lactococcal P1 promoter with no 5' ATG

<400> SEQUENCE: 28

agataggaaa atttcactta cgcagatcaa gttttt                               36


<210> SEQ ID NO 29
<211> LENGTH: 89
<212> TYPE: DNA
<213> ORGANISM: Artificial Sequence
<220> FEATURE:
<223> OTHER INFORMATION: thyA promoter not included

<400> SEQUENCE: 29

tctgagaggt tattttggga aatactattg aaccatatcg aggtgtgtgg tataatgaag     60

ggaattaaaa aagataggaa aatttcatg                                       89


<210> SEQ ID NO 30
<211> LENGTH: 20
<212> TYPE: DNA
<213> ORGANISM: Artificial Sequence
<220> FEATURE:
<223> OTHER INFORMATION: 3' SpeI restriction site

<400> SEQUENCE: 30

aaaatccgta actaactagt                                                 20


<210> SEQ ID NO 31
<211> LENGTH: 35
<212> TYPE: DNA
<213> ORGANISM: Artificial Sequence
<220> FEATURE:
<223> OTHER INFORMATION: stop codon of usp45-hIL-10 sequence

<400> SEQUENCE: 31

gatttagcaa tttaaattaa attaatctat aagtt                                35


<210> SEQ ID NO 32
<211> LENGTH: 26
<212> TYPE: DNA
<213> ORGANISM: Artificial Sequence
```

-continued

```
<220> FEATURE:
<223> OTHER INFORMATION: engineered XbaI restriction site

<400> SEQUENCE: 32

tctagaatta atctataagt tactga                                         26
```